United States Patent
Smith et al.

(10) Patent No.: US 9,695,198 B2
(45) Date of Patent: Jul. 4, 2017

(54) FACTOR IXA INHIBITORS

(71) Applicants: Cameron James Smith, Lawrenceville, NJ (US); Edward Sherer, Manville, NJ (US); Louis-Charles Campeau, Morris Plains, NJ (US); James Balkovec, Martinsville, NJ (US); William John Greenlee, Teaneck, NJ (US); Derun Li, Scotch Plains, NJ (US); Liangqin Guo, Edison, NJ (US); Tin-Yau Chan, Edison, NJ (US); Yi-Heng Chen, Whippany, NJ (US); Yili Chen, Hillsborough, NJ (US); Samuel Chackalamannil, Califon, NJ (US); John Qiang Tan, Westfield, NJ (US); Tomokazu Hirabayashi, Shizuoka Prefecture (JP); Mika Sekioka, Shizuoka Prefecture (JP); MERCK SHARP & DOHME CORP., Rahway, NJ (US); MOCHIDA PHARMACEUTICAL CO., LTD., Tokyo (JP)

(72) Inventors: Cameron James Smith, Lawrenceville, NJ (US); Edward Sherer, Manville, NJ (US); Louis-Charles Campeau, Morris Plains, NJ (US); James Balkovec, Martinsville, NJ (US); William John Greenlee, Teaneck, NJ (US); Derun Li, Scotch Plains, NJ (US); Liangqin Guo, Edison, NJ (US); Tin-Yau Chan, Edison, NJ (US); Yi-Heng Chen, Whippany, NJ (US); Yili Chen, Hillsborough, NJ (US); Samuel Chackalamannil, Califon, NJ (US); John Qiang Tan, Westfield, NJ (US); Tomokazu Hirabayashi, Shizuoka Prefecture (JP); Mika Sekioka, Shizuoka Prefecture (JP)

(73) Assignees: Merck Sharp & Dohme Corp., Rahway, NJ (US); Mochida Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 14/652,150

(22) PCT Filed: Dec. 16, 2013

(86) PCT No.: PCT/US2013/075231
§ 371 (c)(1),
(2) Date: Jun. 15, 2015

(87) PCT Pub. No.: WO2014/099694
PCT Pub. Date: Jun. 26, 2014

(65) Prior Publication Data
US 2015/0368269 A1 Dec. 24, 2015

Related U.S. Application Data

(60) Provisional application No. 61/739,242, filed on Dec. 19, 2012.

(51) Int. Cl.
*C07D 413/14* (2006.01)
*C07D 417/06* (2006.01)
(Continued)

(52) U.S. Cl.
CPC ......... *C07D 513/04* (2013.01); *C07D 413/06* (2013.01); *C07D 413/12* (2013.01);
(Continued)

(58) Field of Classification Search
CPC .. C07D 413/12; C07D 413/14; C07D 498/04; C07D 417/06
See application file for complete search history.

(56) References Cited

U.S. PATENT DOCUMENTS

2004/0220206 A1 11/2004 Smallheer et al.
2005/0228000 A1 10/2005 Smallheer et al.
(Continued)

FOREIGN PATENT DOCUMENTS

| WO | WO2011025565 A1 | 3/2011 |
| WO | WO2014099695 A1 | 6/2014 |
| WO | WO2014120346 A1 | 8/2014 |

OTHER PUBLICATIONS

Nishida, et al. Document No. 154:310655, retrieved from CAPLUS; Mar. 3, 2011.*
(Continued)

*Primary Examiner* — Shawquia Jackson
(74) *Attorney, Agent, or Firm* — Nicole M. Beeler; Catherine D. Fitch

(57) ABSTRACT

The present invention provides a compound of Formula (I)

(I)

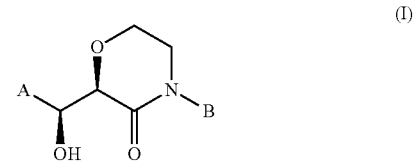

where A is a heterocycle ring system and B is a heterocycle ring system or aryl ring system, and pharmaceutical compositions comprising one or more said compounds, and methods for using said compounds for treating or preventing thromboses, embolisms, hypercoagulability or fibrotic changes.

5 Claims, No Drawings

(51) Int. Cl.
*C07D 498/04* (2006.01)
*C07D 513/04* (2006.01)
*C07D 413/12* (2006.01)
*C07D 471/04* (2006.01)
*C07D 413/06* (2006.01)

(52) U.S. Cl.
CPC ......... *C07D 413/14* (2013.01); *C07D 417/06* (2013.01); *C07D 471/04* (2013.01); *C07D 498/04* (2013.01)

(56) References Cited

U.S. PATENT DOCUMENTS

2006/0293336 A1    12/2006    Sutton et al.
2008/0279845 A1    11/2008    Conley et al.
2009/0181983 A1    7/2009    Corte
2011/0059958 A1    3/2011    Nishida et al.
2011/0065682 A1    3/2011    Clasby et al.

OTHER PUBLICATIONS

Chackalamannil, et al. Document No. 155:40985, retrieved from CAPLUS; Jun. 10, 2011.*
International Search Report and Written Opinion for PCT/US2013/075231 mailed on Apr. 21, 2014, 8 pages.

* cited by examiner

FACTOR IXA INHIBITORS

CROSS REFERENCE TO RELATED APPLICATIONS

This application is a U.S. National Phase application under 35 U.S.C. §371 of PCT Application No. PCT/US13/75231 filed Dec. 16, 2013, which claims priority from U.S. Provisional Application Ser. No. 61/739,242, filed Dec. 19, 2012.

BACKGROUND OF THE INVENTION

Factor IXa is a plasma serine protease involved in the regulation of blood coagulation. While blood coagulation is a necessary and important part of the regulation of an organism's homeostasis, abnormal blood coagulation can also have deleterious effects. For instance, thrombosis is the formation or presence of a blood clot inside a blood vessel or cavity of the heart. Such a blood clot can lodge in a blood vessel blocking circulation and inducing a heart attack or stroke. Thromboembolic disorders are the largest cause of mortality and disability in the industrialized world.

Blood clotting is a process of control of the blood stream essential for the survival of mammals. The process of clotting, and the subsequent dissolution of the clot after wound healing has taken place, commences after vascular damage, and can be divided into four phases. The first phase, vasoconstriction or vasocontraction, can cause a decrease in blood loss in the damaged area. In the next phase, platelet activation by thrombin, platelets attach to the site of the vessel wall damage and form a platelet aggregate. In the third phase, formation of clotting complexes leads to massive formation of thrombin, which converts soluble fibrinogen to fibrin by cleavage of two small peptides. In the fourth phase, after wound healing, the thrombus is dissolved by the action of the key enzyme of the endogenous fibrinolysis system, plasmin.

Two alternative pathways can lead to the formation of a fibrin clot, the intrinsic and the extrinsic pathway. These pathways are initiated by different mechanisms, but in the later phase they converge to give a common final path of the clotting cascade. In this final path of clotting, clotting factor X is activated. The activated factor X is responsible for the formation of thrombin from the inactive precursor prothrombin circulating in the blood. The formation of a thrombus on the bottom of a vessel wall abnormality without a wound is the result of the intrinsic pathway. Fibrin clot formation as a response to tissue damage or an injury is the result of the extrinsic pathway. Both pathways comprise a relatively large number of proteins, which are known as clotting factors. The intrinsic pathway requires the clotting factors V, VIII, IX, X, XI and XII and also prekallikrein, high molecular weight kininogen, calcium ions and phospholipids from platelets. Clotting factor IX can be activated by means of the intrinsic pathway and the extrinsic pathway. The activation of factor IXa is thus a central point of intersection between the two pathways of activation of clotting. Factor IXa has an important role in blood clotting. Defects in factor IXa lead to hemophilia B, while increased concentrations of factor IXa in the blood lead to a significantly increased risk of thrombosis formation (Weltermann A, et al., J Thromb Haemost. 2003; 1: 28-32). The regulation of factor IXa activity can reduce thrombus formation in animal models (Feuerstein G Z, et al., Thromb Haemost. 1999; 82: 1443-1445). Vijaykumar et al., *Bioorganic & Medicinal Chemistry Letters* (2006), 16 (10), 2796-2799, discloses hydroxy pyrazole based factor IXa inhibitors.

SUMMARY OF THE INVENTION

The invention includes compounds for inhibiting loss of blood platelets, inhibiting formation of blood platelet aggregates, inhibiting formation of fibrin, inhibiting thrombus formation, and inhibiting embolus formation in a mammal, comprising a compound of the invention in a pharmaceutically acceptable carrier. These compounds may optionally include anticoagulants, antiplatelet agents, and thrombolytic agents. The compounds can be added to blood, blood products, or mammalian organs in order to effect the desired inhibitions.

The invention also includes a compound for preventing or treating unstable angina, refractory angina, myocardial infarction, transient ischemic attacks, atrial fibrillation, thrombotic stroke, embolic stroke, deep vein thrombosis, disseminated intravascular coagulation, ocular build up of fibrin, and reocclusion or restenosis of recanalized vessels, in a mammal, comprising a compound of the invention in a pharmaceutically acceptable carrier. These compounds may optionally include anticoagulants, antiplatelet agents, and thrombolytic agents.

The invention also includes a method for reducing the thrombogenicity of a surface in a mammal by attaching to the surface, either covalently or noncovalently, a compound of the invention.

Compounds of the invention are Factor IXa inhibitors and may have therapeutic value in, for example, preventing coronary artery disease. The invention includes compounds of formula I:

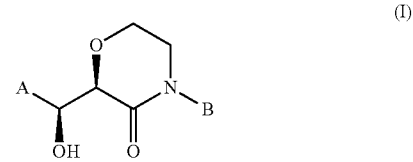

(I)

A is
1) a 9-10 membered bicyclic heterocycle having 2-3 heteroatoms independently selected from N, S and O, which 9-10 membered bicyclic heterocycle is unsubstituted or substituted with =O, —C(=NH)NH$_2$, or pyrazole, or
2) a 12-, 13-, or 14-membered tricyclic heterocycle having 3-5 heteroatoms selected from N, S and O, which 12-, 13-, or 14-membered heterocycle is unsubstituted or substituted with =O or NH$_2$;

B is
1) a 5-membered monocyclic heterocycle having 2 nitrogen atoms and 3 carbon atoms, where
one 5-membered monocyclic heterocycle nitrogen is substituted with
a) 6-membered monocyclic heterocyle having one or two nitrogen atoms or one oxygen atom,
b) C$_{1-6}$ alkyl,
c) C$_{3-8}$ carbocycle, or
d) aryl,
wherein heterocycle, alkyl, carbocycle and aryl are unsubstituted, mono-substituted, or independently di-substituted with CF$_3$, OCH$_3$, F, CN, —CHF$_2$, or =O, and one 5-membered monocyclic heterocycle carbon atom is unsubstituted or substituted with $C_{1-6}$ alkyl, 2) a 6-membered monocyclic heterocycle having 1 nitrogen atom and 5 carbon atoms, where three carbon atoms are unsubstituted, and one or two carbon atoms are independently unsubstituted or independently substituted with $CF_3$, —$C(CH_3)_2OH$, —$OCHF_2$, —$CH(CF_3)OH$, —$C(CF_3)(CH_3)OH$, F,

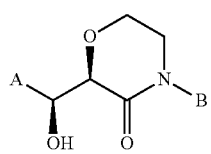

or 3) aryl, substituted with —$C_{1-6}$ alkyl.

In one embodiment of compounds of formula (I),

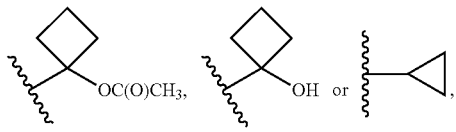

(I)

A has the formula (II)

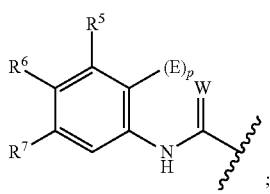

(II)

wherein
W is N or CH;
E is $S(O)_2$ or $C(O)$;
p is 0 or 1;
$R^5$ is H or, together with $R^6$ and the atoms to which they are attached, forms a 5- or 6-membered monocyclic heterocycle having 2 heteroatoms independently selected from N, S and O, which heterocycle is substituted at a carbon atom with $NH_2$;
$R^6$ is H, —$C(=NH)NH_2$, pyrazole, or, together with $R^5$ and the atoms to which they are attached, forms a 5- or 6-membered monocyclic heterocycle, having 2 heteroatoms independently selected from N, S and O, which heterocycle is substituted at a carbon atom with $NH_2$, or, provided $R^5$ and $R^6$ do not form a heterocycle, forms, together with $R^7$ and the atoms to which they are attached, a 5-membered monocyclic heterocycle, having 2 heteroatoms independently selected from N, S and O, or forms, together with $R^7$ and the atoms to which they are attached, a 6-membered monocyclic heterocycle having 1 N atom, which 5- or 6-membered heterocycle is substituted at a carbon atom with $NH_2$;
$R^7$ is H, —$C(=NH)NH_2$, or, provided $R^5$ and $R^6$ do not form a heterocycle, forms, together with $R^6$ and the atoms to which they are attached, a 5-membered monocyclic heterocycle, having 2 heteroatoms independently selected from N, S and O, or forms, together with $R^6$ and the atoms to which they are attached, a 6-membered monocyclic heterocycle having 1 N atom, which 5- or 6-membered heterocycle is substituted at a carbon atom with $NH_2$;
provided $R^5$, $R^6$ and $R^7$ are not simultaneously H; and
B is 1) a 5-membered monocyclic heterocycle having 2 nitrogen atoms and 3 carbon atoms, where
one 5-membered monocyclic heterocycle nitrogen is substituted with

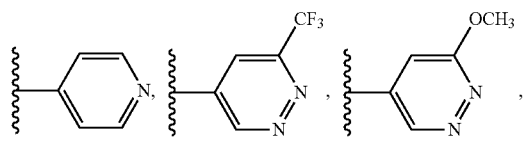

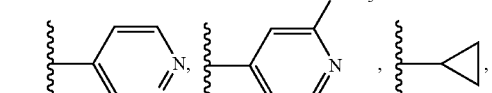

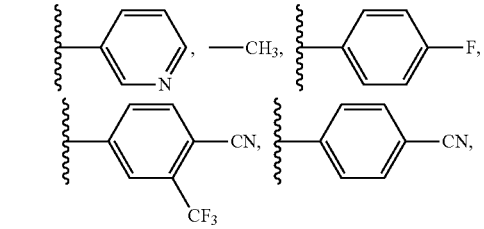

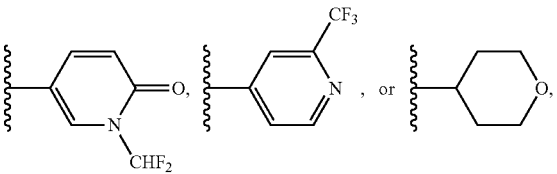

and one carbon atom in the 5-membered monocyclic heterocycle is unsubstituted or substituted with —$CH_3$, 2) a 6-membered monocyclic heterocycle having 1 nitrogen atom and 5 carbon atoms, where one or two carbon atoms are independently unsubstituted or independently substituted with $CF_3$, —$C(CH_3)_2OH$, —$OCHF_2$, —$CH(CF_3)OH$, —$C(CF_3)(CH_3)OH$, F,

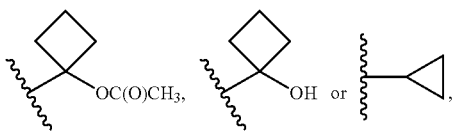

or 3) aryl, substituted with —$CH_3$.

In another embodiment of compounds of formula I,

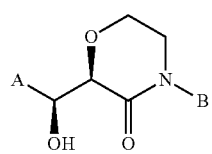

(I)

A is
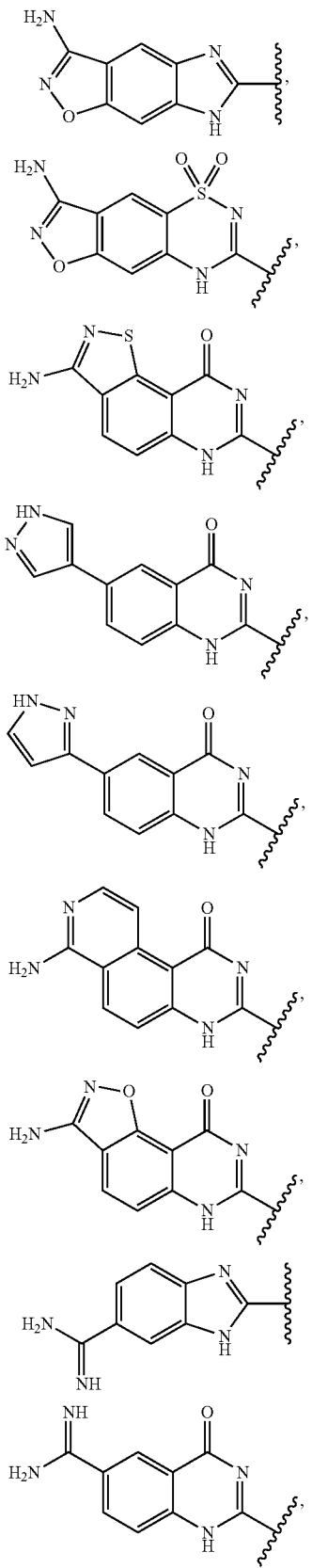
B is
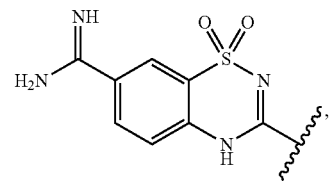
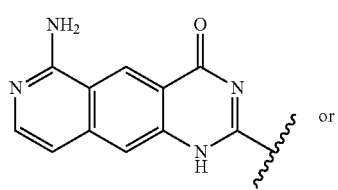 or
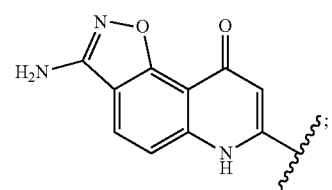
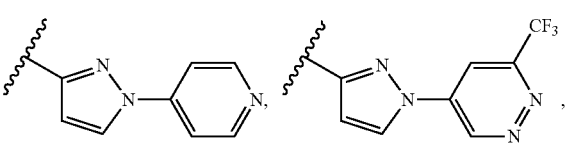
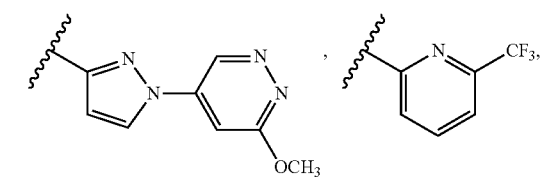
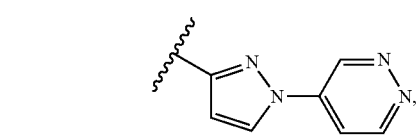
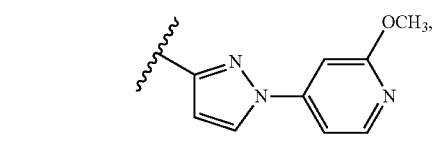
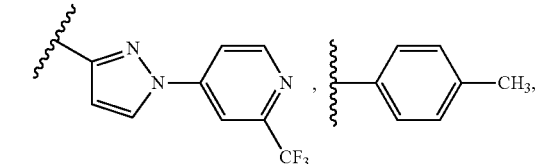
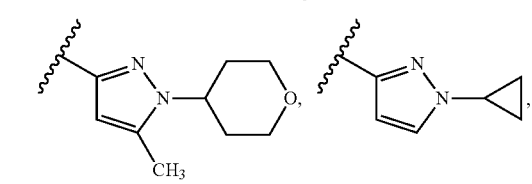

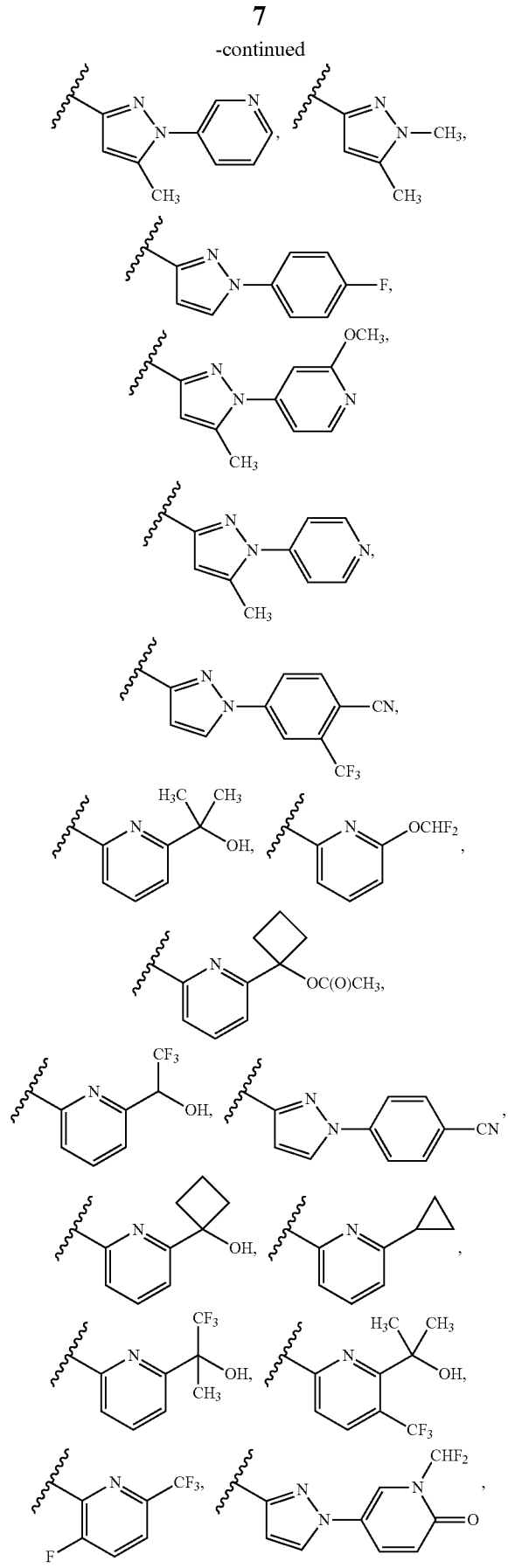

In another embodiment of the invention, the compound is
3-Amino-7-((S)-hydroxy((R)-3-oxo-4-(1-(pyridin-4-yl)-1H-pyrazol-3-yl)morpholin-2-yl)methyl)isoxazolo[5,4-f]quinazolin-9(6H)-one (EXAMPLE 1), (R)-2-((S)-(3-Amino-9-oxo-6,9-dihydroisothiazolo[5,4-f]quinazolin-7-yl)(hydroxy)methyl)-4-(1-(pyridin-4-yl)-1H-pyrazol-3-yl)morpholin-3-one (EXAMPLE 2), (R)-2-((S)-(3-Amino-9-oxo-6,9-dihydroisothiazolo[5,4-f]quinazolin-7-yl)(hydroxy)methyl)-4-(5-methyl-1-(pyridin-4-yl)-1H-pyrazol-3-yl)morpholin-3-one (EXAMPLE 3), (R)-2-((S)-(3-Amino-9-oxo-6,9-dihydroisothiazolo[5,4-f]quinazolin-7-yl)(hydroxy)methyl)-4-(5-methyl-1-(pyridin-3-yl)-1H-pyrazol-3-yl)morpholin-3-one (EXAMPLE 4), (R)-2-((S)-(3-Amino-9-oxo-6,9-dihydroisothiazolo[5,4-f]quinazolin-7-yl)(hydroxy)methyl)-4-(1-(2-methoxypyridin-4-yl)-1H-pyrazol-3-yl)morpholin-3-one (EXAMPLE 5), (R)-2-((S)-(3-Amino-9-oxo-6,9-dihydroisothiazolo[5,4-f]quinazolin-7-yl)(hydroxy)methyl)-4-(1-(2-methoxypyridin-4-yl)-5-methyl-1H-pyrazol-3-yl)morpholin-3-one (EXAMPLE 6), (R)-2-((S)-(3-Amino-9-oxo-6,9-dihydroisothiazolo[5,4-f]quinazolin-7-yl)(hydroxy)methyl)-4-(1-(2-(trifluoromethyl)pyridin-4-yl)-1H-pyrazol-3-yl)morpholin-3-one (EXAMPLE 7), (R)-2-((S)-(3-Amino-9-oxo-6,9-dihydroisothiazolo[5,4-f]quinazolin-7-yl)(hydroxy)methyl)-4-(5-methyl-1-(2-(trifluoromethyl)pyridin-4-yl)-1H-pyrazol-3-yl)morpholin-3-one (EXAMPLE 8), (R)-2-((S)-(3-Amino-9-oxo-6,9-dihydroisothiazolo[5,4-f]quinazolin-7-yl)(hydroxy)methyl)-4-(1-(pyridazin-4-yl)-1H-pyrazol-3-yl)morpholin-3-one (EXAMPLE 9), (R)-2-((S)-(3-Amino-9-oxo-6,9-dihydroisothiazolo[5,4-f]quinazolin-7-yl)(hydroxy)methyl)-4-(1-(1-(difluoromethyl)-6-oxo-1,6-dihydropyridin-3-yl)-1H-pyrazol-3-yl)morpholin-3-one (EXAMPLE 10), (R)-2-((S)-(3-Amino-9-oxo-6,9-dihydroisothiazolo[5,4-f]quinazolin-7-yl)(hydroxy)methyl)-4-(1-(4-fluorophenyl)-5-methyl-1H-pyrazol-3-yl)morpholin-3-one (EXAMPLE 11), 4-(3-((R)-2-((S)-(3-Amino-9-oxo-6,9-dihydroisothiazolo[5,4-f]quinazolin-7-yl)(hydroxy)methyl)-3-oxomorpholino)-1H-pyrazol-1-yl)benzonitrile (EXAMPLE 12), 4-(3-((R)-2-((S)-(3-Amino-9-oxo-6,9-dihydroisothiazolo[5,4-f]quinazolin-7-yl)(hydroxy)methyl)-3-oxomorpholino)-1H-pyrazol-1-yl)-2-(trifluoromethyl)benzonitrile (EXAMPLE 13), (R)-2-((S)-(3-Amino-9-oxo-6,9-dihydroisothiazolo[5,4-f]quinazolin-7-yl)(hydroxy)methyl)-4-(1,5-dimethyl-1H-pyrazol-3-yl)morpholin-3-one (EXAMPLE 14), (R)-2-((S)-(3-Amino-9-oxo-6,9-dihydroisothiazolo[5,4-f]quinazolin-7-yl)(hydroxy)methyl)-4-(1-cyclopropyl-1H-pyrazol-3-yl)morpholin-3-one (EXAMPLE 15),
(R)-2-((S)-(3-Amino-9-oxo-6,9-dihydroisothiazolo[5,4-f]quinazolin-7-yl)(hydroxy)methyl)-4-(5-methyl-1-(tetrahydro-2H-pyran-4-yl)-1H-pyrazol-3-yl)morpholin-3-one (EXAMPLE 16),
(R)-2-((S)-(3-Amino-9-oxo-6,9-dihydroisothiazolo[5,4-f]quinazolin-7-yl)(hydroxy)methyl)-4-(6-(trifluoromethyl)pyridin-2-yl)morpholin-3-one (EXAMPLE 17),
(R)-2-((S)-(3-Amino-9-oxo-6,9-dihydroisothiazolo[5,4-f]quinazolin-7-yl)(hydroxy)methyl)-4-(3-fluoro-6-(trifluoromethyl)pyridin-2-yl)morpholin-3-one (EXAMPLE 18),
(R)-2-((S)-(3-Amino-9-oxo-6,9-dihydroisothiazolo[5,4-f]quinazolin-7-yl)(hydroxy)methyl)-4-(6-(difluoromethoxy)pyridin-2-yl)morpholin-3-one (EXAMPLE 19),
(R)-2-((S)-(3-Amino-9-oxo-6,9-dihydroisothiazolo[5,4-f]quinazolin-7-yl)(hydroxy)methyl)-4-(6-cyclopropylpyridin-2-yl)morpholin-3-one (EXAMPLE 20),
(R)-2-((S)-(3-Amino-9-oxo-6,9-dihydroisothiazolo[5,4-f]quinazolin-7-yl)(hydroxy)methyl)-4-(6-(2-hydroxypropan-2-yl)pyridin-2-yl)morpholin-3-one (EXAMPLE 21),
(R)-2-((S)-(3-Amino-9-oxo-6,9-dihydroisothiazolo[5,4-f]quinazolin-7-yl)(hydroxy)methyl)-4-(6-(2-hydroxypropan-2-yl))-5-(trifluoromethyl)pyridin-2-yl)morpholin-3-one (EXAMPLE 22),
1-(6-((R)-2-((S)-(3-Amino-9-oxo-6,9-dihydroisothiazolo[5,4-f]quinazolin-7-yl)(hydroxy)methyl)-3-oxomorpholino)pyridin-2-yl)cyclobutyl acetate (EXAMPLE 23),
(R)-2-((S)-(3-Amino-9-oxo-6,9-dihydroisothiazolo[5,4-f]quinazolin-7-yl)(hydroxy)methyl)-4-(6-(1-hydroxycyclobutyl)pyridin-2-yl)morpholin-3-one (EXAMPLE 24),
(2R)-2-((S)-(3-Amino-9-oxo-6,9-dihydroisothiazolo[5,4-f]quinazolin-7-yl)(hydroxy)methyl)-4-(6-(2,2,2-trifluoro-1-hydroxyethyl)pyridin-2-yl)morpholin-3-one (EXAMPLE 25),
(2R)-2-((S)-(3-Amino-9-oxo-6,9-dihydroisothiazolo[5,4-f]quinazolin-7-yl)(hydroxy)methyl)-4-(6-(1,1,1-trifluoro-2-hydroxypropan-2-yl)pyridin-2-yl)morpholin-3-one (EXAMPLE 26),
3-Amino-7-((S)-hydroxy((R)-3-oxo-4-(1-(pyridin-4-yl)-1H-pyrazol-3-yl)morpholin-2-yl)methyl)isoxazolo[5,4-f]quinolin-9(6H)-one (EXAMPLE 27),
(R)-2-((S)-(6-Amino-4-oxo-1,4-dihydropyrido[3,4-g]quinazolin-2-yl)(hydroxy)methyl)-4-(1-(pyridin-4-yl)-1H-pyrazol-3-yl)morpholin-3-one (EXAMPLE 28),
2-((S)-Hydroxy((R)-3-oxo-4-(p-tolyl)morpholin-2-yl)methyl)-4-oxo-1,4-dihydroquinazoline-6-carboximidamide (EXAMPLE 29),
2-((S)-Hydroxy((R)-3-oxo-4-(p-tolyl)morpholin-2-yl)methyl)-1H-benzo[d]imidazole-6-carboximidamide (EXAMPLE 30),
3-((S)-Hydroxy((R)-3-oxo-4-(p-tolyl)morpholin-2-yl)methyl)-4H-benzo [e][1,2,4]thiadiazine-7-carboximidamide 1,1-dioxide (EXAMPLE 31),
(R)-2-((S)-(3-Amino-7H-imidazo[4',5':4,5]benzo[1,2-d]isoxazol-6-yl)(hydroxy)methyl)-4-(1-(6-(trifluoromethyl)pyridazin-4-yl)-1H-pyrazol-3-yl)morpholin-3-one (EXAMPLE 32),
(2R)-2-[(S)-(3-amino-7H-imidazo[4,5-f][1,2]benzisoxazol-6-yl)(hydroxy)methyl]-4-(1-pyridin-4-yl-1H-pyrazol-3-yl)morpholin-3-one,
(2R)-2-[(S)-(3-amino-7H-imidazo[4,5-f][1,2]benzisoxazol-6-yl)(hydroxy)methyl]-4-[1-(6-methoxypyridazin-4-yl)-1H-pyrazol-3-yl]morpholin-3-one,
(R)-2-((S)-(8-Amino-1,1-dioxido-4H-isoxazolo[4',5':4,5]benzo[1,2-e][1,2,4]thiadiazin-3-yl)(hydroxy)methyl)-4-(1-(pyridin-4-yl)-1H-pyrazol-3-yl)morpholin-3-one (EXAMPLE 35),
(2R)-2-[(S)-(8-amino-1,1-dioxido-4H-isoxazolo[5,4-g][1,2,4]benzothiadiazin-3-yl)(hydroxy)methyl]-4-[6-(trifluoromethyl)pyridin-2-yl]morpholin-3-one,
(R)-2-((S)-(7-Amino-1-oxo-1,4-dihydropyrido[4,3-f]quinazolin-3-yl)(hydroxy)methyl)-4-(1-(pyridin-4-yl)-1H-pyrazol-3-yl)morpholin-3-one (EXAMPLE 37),
(R)-2-((S)-hydroxy(4-oxo-6-(1H-pyrazol-4-yl)-1,4-dihydroquinazolin-2-yl)methyl)-4-(1-(pyridazin-4-yl)-1H-pyrazol-3-yl)morpholin-3-one (EXAMPLE 38),
2-{(S)-hydroxy[(2R)-3-oxo-4-(1-pyridazin-4-yl-1H-pyrazol-3-yl)morpholin-2-yl]methyl}-6-(1H-pyrazol-3-yl)quinazolin-4(1H)-one,
2-[(S)-hydroxy{(2R)-4-[1-(2-methoxypyridin-4-yl)-1H-pyrazol-3-yl]-3-oxomorpholin-2-yl}methyl]-6-(1H-pyrazol-4-yl)quinazolin-4(1H)-one,
3-amino-7-{(S)-hydroxy[(2R)-3-oxo-4-{1-[2-(trifluoromethyl)pyridin-4-yl]-1H-pyrazol-3-yl}morpholin-2-yl]methyl}isoxazolo[5,4-f]quinazolin-9(6H)-one,
(R)-2-((S)-(6-amino-4-oxo-1,4-dihydropyrido[3,4-g]quinazolin-2-yl)(hydroxy)methyl)-4-(1-(pyridin-4-yl)-1H-pyrazol-3-yl)morpholin-3-one,
2-((3-amino-9-oxo-6,9-dihydroisothiazolo[5,4-f]quinazolin-7-yl)(hydroxy)methyl)-4-(1-(pyridin-4-yl)-1H-pyrazol-3-yl)morpholin-3-one,
7-amino-3-{(S)-hydroxy[(2R)-3-oxo-4-(1-pyridin-4-yl-1H-pyrazol-3-yl)morpholin-2-yl]methyl}pyrido[4,3-f]quinazolin-1 (4H)-one, or
6-(aminomethyl)-2-[(S)-hydroxy{(2R)-4-[1-(2-methoxypyridin-4-yl)-1H-pyrazol-3-yl]-3-oxomorpholin-2-yl}methyl]quinazolin-4(1H)-one.

It will be understood that, as used herein, references to the compounds of structural Formula I are meant to also include the pharmaceutically acceptable salts, and also salts that are not pharmaceutically acceptable when they are used as precursors to the free compounds or their pharmaceutically acceptable salts or in other synthetic manipulations.

The compounds of the present invention may be administered in the form of a pharmaceutically acceptable salt. The term "pharmaceutically acceptable salt" refers to salts prepared from pharmaceutically acceptable non-toxic bases or acids including inorganic or organic bases and inorganic or organic acids. Salts of basic compounds encompassed within the term "pharmaceutically acceptable salt" refer to non-toxic salts of the compounds of this invention which are generally prepared by reacting the free base with a suitable organic or inorganic acid. Representative salts of basic compounds of the present invention include, but are not limited to, the following: acetate, ascorbate, adipate, alginate, aspirate, benzenesulfonate, benzoate, bicarbonate, bisulfate, bitartrate, borate, bromide, butyrate, camphorate, camphorsulfonate, camsylate, carbonate, chloride, clavulanate, citrate, cyclopentane propionate, diethylacetic, digluconate, dihydrochloride, dodecylsulfanate, edetate, edisylate, estolate, esylate, ethanesulfonate, formic, fumarate, gluceptate, glucoheptanoate, gluconate, glutamate, glycerophosphate, glycollylarsanilate, hemisulfate, heptanoate, hexanoate, hexylresorcinate, hydrabamine, hydrobromide, hydrochloride, 2-hydroxyethanesulfonate, hydroxynaphthoate, iodide, isonicotinic, isothionate, lactate, lactobionate, laurate, malate, maleate, mandelate, mesylate, methylbromide, methylnitrate, methylsulfate, methanesulfonate, mucate, 2-naphthalenesulfonate, napsylate, nicotinate, nitrate, N-methylglucamine ammonium salt, oleate, oxalate, pamoate (embonate), palmitate, pantothenate, pectinate, persulfate, phosphate/diphosphate, pimelic, phenylpropionic, polygalacturonate, propionate, salicylate, stearate, sulfate, subacetate, succinate, tannate, tartrate, teoclate, thiocyanate, tosylate, triethiodide, trifluoroacetate, undeconate, valerate and the like. Furthermore, where the compounds of the invention carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, cyclic amines, dicyclohexyl amines and basic ion-exchange resins, such as arginine, betaine, caffeine, choline, N,N-dibenzylethylenediamine, diethylamine, 2-diethylaminoethanol, 2-dimethylaminoethanol, ethanolamine, ethylamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, trometamine, and the like. Also, included are the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others.

These salts can be obtained by known methods, for example, by mixing a compound of the present invention with an equivalent amount and a solution containing a desired acid, base, or the like, and then collecting the desired salt by filtering the salt or distilling off the solvent. The compounds of the present invention and salts thereof may form solvates with a solvent such as water, ethanol, or glycerol. The compounds of the present invention may form an acid addition salt and a salt with a base at the same time according to the type of substituent of the side chain.

The present invention encompasses all stereoisomeric forms of the compounds of Formula I. Centers of asymmetry that are present in the compounds of Formula I can all independently of one another have (R) configuration or (S) configuration. When bonds to the chiral carbon are depicted as straight lines in the structural Formulas of the invention, it is understood that both the (R) and (S) configurations of the chiral carbon, and hence both enantiomers and mixtures thereof, are embraced within the Formula. Similarly, when a compound name is recited without a chiral designation for a chiral carbon, it is understood that both the (R) and (S) configurations of the chiral carbon, and hence individual enantiomers and mixtures thereof, are embraced by the name. The production of specific stereoisomers or mixtures thereof may be identified in the Examples where such stereoisomers or mixtures were obtained, but this in no way limits the inclusion of all stereoisomers and mixtures thereof from being within the scope of this invention.

The invention includes all possible enantiomers and diastereomers and mixtures of two or more stereoisomers, for example mixtures of enantiomers and/or diastereomers, in all ratios. Thus, enantiomers are a subject of the invention in enantiomerically pure form, both as levorotatory and as dextrorotatory antipodes, in the form of racemates and in the form of mixtures of the two enantiomers in all ratios. In the case of a cis/trans isomerism the invention includes both the cis form and the trans form as well as mixtures of these forms in all ratios. The preparation of individual stereoisomers can be carried out, if desired, by separation of a mixture by customary methods, for example by chromatography or crystallization, by the use of stereochemically uniform starting materials for the synthesis or by stereoselective synthesis. Optionally a derivatization can be carried out before a separation of stereoisomers. The separation of a mixture of stereoisomers can be carried out at an intermediate step during the synthesis of a compound of Formula I or it can be done on a final racemic product. Absolute stereochemistry may be determined by X-ray crystallography of crystalline products or crystalline intermediates which are derivatized, if necessary, with a reagent containing a stereogenic center of known configuration. Where compounds of this invention are capable of tautomerization, all individual tautomers as well as mixtures thereof are included in the scope of this invention. The present invention includes all such isomers, as well as salts, solvates (including hydrates) and solvated salts of such racemates, enantiomers, diastereomers and tautomers and mixtures thereof.

In the compounds of the invention, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the specifically and generically described compounds. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds can be prepared without undue experimentation by conventional techniques well known to those skilled in the art or by processes analogous to those described in the general process schemes and examples herein using appropriate isotopically-enriched reagents and/or intermediates.

Furthermore, compounds of the present invention may exist in amorphous form and/or one or more crystalline forms, and as such all amorphous and crystalline forms and mixtures thereof of the compounds of Formula I are intended to be included within the scope of the present invention. In addition, some of the compounds of the instant invention may form solvates with water (i.e., a hydrate) or common organic solvents. Such solvates and hydrates, particularly the pharmaceutically acceptable solvates and hydrates, of the instant compounds are likewise encompassed within the scope of this invention, along with unsolvated and anhydrous forms.

Reference to the compounds of this invention as those of a specific formula or embodiment, e.g., Formula I or any other generic structural formula or specific compound described or claimed herein, is intended to encompass the specific compound or compounds falling within the scope of the formula or embodiment, including salts thereof, particularly pharmaceutically acceptable salts, solvates of such compounds and solvated salt forms thereof, where such forms are possible unless specified otherwise.

Except where noted herein, "alkyl" is intended to include both branched- and straight-chain saturated aliphatic hydrocarbon groups having the specified number of carbon atoms. Commonly used abbreviations for alkyl groups are used throughout the specification, e.g. methyl may be represented by conventional abbreviations including "Me" or $CH_3$ or a symbol that is an extended bond as the terminal group, e.g.

ethyl may be represented by "Et" or $CH_2CH_3$, propyl may be represented by "Pr" or $CH_2CH_2CH_3$, butyl may be represented by "Bu" or $CH_2CH_2CH_2CH_3$, etc. "$C_{1-4}$ alkyl" (or "$C_1$-$C_4$ alkyl") for example, means linear or branched chain alkyl groups, including all isomers, having the specified number of carbon atoms. For example, the structures

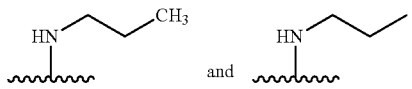

have equivalent meanings $C_{1-4}$ alkyl includes n-, iso-, sec- and t-butyl, n- and isopropyl, ethyl and methyl. If no number is specified, 1-4 carbon atoms are intended for linear or branched alkyl groups.

Also, in the case of a carboxylic acid (—COOH) or alcohol group being present in the compounds of the present invention, pharmaceutically acceptable esters of carboxylic acid derivatives, such as methyl, ethyl, or pivaloyloxymethyl, or acyl derivatives of alcohols, such as O-acetyl, O-pivaloyl, O-benzoyl, and O-aminoacyl, can be employed. Included are those esters and acyl groups known in the art for modifying the solubility or hydrolysis characteristics for use as sustained-release or prodrug formulations.

If the compounds of Formula I simultaneously contain acidic and basic groups in the molecule the invention also includes, in addition to the salt forms mentioned, inner salts or betaines (zwitterions). Salts can be obtained from the compounds of Formula I by customary methods which are known to the person skilled in the art, for example by combination with an organic or inorganic acid or base in a solvent or dispersant, or by anion exchange or cation exchange from other salts. The present invention also includes all salts of the compounds of Formula I which, owing to low physiological compatibility, are not directly suitable for use in pharmaceuticals but which can be used, for example, as intermediates for chemical reactions or for the preparation of physiologically acceptable salts.

Any pharmaceutically acceptable pro-drug modification of a compound of this invention which results in conversion in vivo to a compound within the scope of this invention is also within the scope of this invention. For example, esters can optionally be made by esterification of an available carboxylic acid group or by formation of an ester on an available hydroxy group in a compound. Similarly, labile amides can be made. Pharmaceutically acceptable esters or amides of the compounds of this invention may be prepared to act as pro-drugs which can be hydrolyzed back to an acid (or —COO-depending on the pH of the fluid or tissue where conversion takes place) or hydroxy form particularly in vivo and as such are encompassed within the scope of this invention. Examples of pharmaceutically acceptable pro-drug modifications include, but are not limited to, —$C_{1-6}$ alkyl esters and —$C_{1-6}$ alkyl substituted with phenyl esters.

Accordingly, the compounds within the generic structural formulas, embodiments and specific compounds described and claimed herein encompass salts, all possible stereoisomers and tautomers, physical forms (e.g., amorphous and crystalline forms), solvate and hydrate forms thereof and any combination of these forms, as well as the salts thereof, pro-drug forms thereof, and salts of pro-drug forms thereof, where such forms are possible unless specified otherwise.

When any variable occurs more than one time in any constituent or in formula I, its definition on each occurrence is independent of its definition at every other occurrence. Also, combinations of substituents and/or variables are permissible only if such combinations result in stable compounds.

Except where noted herein, "alkanol" is intended to include aliphatic alcohols having the specified number of carbon atoms, such as methanol, ethanol, propanol, etc., where the —OH group is attached at any aliphatic carbon, e.g., propan-1-ol, propan-2-ol, etc.

Except where noted herein, alkyl groups may be unsubstituted, or substituted with 1 to 3 substituents on any one or more carbon atoms, with halogen, $C_1$-$C_{20}$ alkyl, $CF_3$, $NH_2$, —$NH(C_1$-$C_6$ alkyl), —$N(C_1$-$C_6$ alkyl)$_2$, $NO_2$, oxo, CN, $N_3$, —OH, —$O(C_1$-$C_6$ alkyl), $C_3$-$C_{10}$ cycloalkyl, $C_2$-$C_6$ alkenyl, $C_2$-$C_6$ alkynyl, $(C_1$-$C_6$ alkyl)$S(O)_{0-2}$—, $HS(O)_{0-2}$—, $(C_1$-$C_6$ alkyl)$S(O)_{0-2}(C_1$-$C_6$ alkyl)-, $HS(O)_{0-2}(C_1$-$C_6$ alkyl)-, $(C_0$-$C_6$ alkyl)C(O)NH—, $H_2N$—C(NH)—, —$O(C_1$-$C_6$ alkyl)$CF_3$, HC(O)—, $(C_1$-$C_6$ alkyl)C(O)—, HOC(O)—, $(C_1$-$C_6$ alkyl) OC(O)—, $HO(C_1$-$C_6$ alkyl)-, $(C_1$-$C_6$ alkyl)$O(C_1$-$C_6$ alkyl)-, $(C_1$-$C_6$ alkyl)C(O)$_{1-2}(C_1$-$C_6$ alkyl)-, $HC(O)_{1-2}(C_1$-$C_6$ alkyl)-, $(C_1$-$C_6$ alkyl)C(O)$_{1-2}$—, HOC(O)NH—, $(C_1$-$C_6$ alkyl)OC(O)NH—, aryl, aralkyl, heterocycle, heterocyclylalkyl, halo-aryl, halo-aralkyl, halo-heterocycle, halo-heterocyclylalkyl, cyano-aryl, cyano-aralkyl, cyano-heterocycle and cyano-heterocyclylalkyl, where such substitution results in formation of a stable compound.

Except where noted, the term "halogen" means fluorine, chlorine, bromine or iodine.

Except where noted, the term "aryl" refers to a stable 6- to 10-membered mono- or bicyclic ring system such as phenyl, or naphthyl. The aryl ring can be unsubstituted or substituted with one or more of $C_{1-4}$ alkyl, hydroxyl, alkoxy, halogen, or amino.

Except where noted, the term "heterocycle" refers to a stable 4- to 7-membered mono- or bicyclic- or stable 7- to 12-membered bicyclic or stable 12- to 14-membered heteroatom-containing ring system unsubstituted or substituted with $C_{1-4}$ alkyl or halogen, any ring of which may be saturated or unsaturated, and which consists of carbon atoms and from one to four heteroatoms selected from the group consisting of N, O and S, and wherein the nitrogen and sulfur heteroatoms may optionally be oxidized, and the nitrogen heteroatom may optionally be quaternized, and including any bicyclic group in which any of the above-defined heterocycle is fused to a benzene ring. Especially useful are rings containing one oxygen or sulfur, one to four nitrogen atoms, or one oxygen or sulfur combined with one or two nitrogen atoms. The heterocycle may be attached at any heteroatom or carbon atom which results in the creation of a stable structure. Examples of such heterocycles include piperidinyl, piperazinyl, 2-oxopiperazinyl, 2-oxopiperidinyl, 2-oxopyrrolodinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, pyridyl, pyridyl N-oxide, pyrazinyl, pyrimidinyl, pyridazinyl, oxazolyl, oxazolidinyl, isoxazolyl, isoxazolidinyl, morpholinyl, thiazolyl, thiazolidinyl, isothiazolyl, quinuclidinyl, isothiazolidinyl, indolyl, quinolinyl, isoquinolinyl, benzimidazolyl, thiadiazoyl, benzopyranyl, benzothiazolyl, benzoxazolyl, furyl, tetrahydrofuryl, tetrahydropyranyl, tetrazole, thienyl, benzothienyl, thiamorpholinyl, thiamorpholinyl sulfoxide, thiamorpholinyl sulfone, and oxadiazolyl. Morpholino is the same as morpholinyl.

Except where noted herein, the term "heteroaryl" refers to a monocyclic unsaturated heterocycle having a specified number of atom members (e.g., 4, 5, 6 or 7-membered), including a specified number of heteroatoms (e.g., 1, 2, 3 or 4 heteroatoms independently selected from N, O or S), or a bicyclic unsaturated ring system having a specified number of atom members (e.g., 7, 8, 9, 10, 11 or 12-membered) including a specified number of heteroatoms (e.g., 1, 2, 3, 4, 5, 6, 7, 8, 9 or 10 heteroatoms independently selected from N, S or O) or a tricyclic unsaturated ring system having a specified number of atom members (e.g., 12-, 13- or 14-membered) including a specified number of heteroatoms (e.g., 1, 2, 3, 4, 5, 6, 7, 8, 9 or 10 heteroatoms independently selected from N, S or O) e.g., 5-membered rings containing one nitrogen (pyrrole), one oxygen (furan) or one sulfur (thiophene) atom, 5-membered rings containing one nitrogen and one sulfur (thiazole) atom, 5-membered rings containing one nitrogen and one oxygen (oxazole or isoxazole) atom, 5-membered rings containing two nitrogen (imidazole or pyrazole) atoms, five-membered aromatic rings containing three nitrogen atoms, five-membered aromatic rings containing one oxygen, one nitrogen or one sulfur atom, five-membered aromatic rings containing two heteroatoms independently selected from oxygen, nitrogen and sulfur, 6-membered rings containing one nitrogen (pyridine), or one oxygen (pyran) atom, 6-membered rings containing two nitrogen (pyrazine, pyrimidine, or pyridazine) atoms, 6-membered rings containing three nitrogen (triazine) atoms, a tetrazolyl ring; a thiazinyl ring; or coumarinyl. Examples of such ring systems are furanyl, thienyl, pyrrolyl, pyridinyl, pyrimidinyl, indolyl, imidazolyl, triazinyl, thiazolyl, isothiazolyl, pyridazinyl, pyrazolyl, oxazolyl, and isoxazolyl.

The term "saturated heterocycle" refers to a saturated monocyclic 5- to 8-membered ring having 1-4 heteroatoms selected from N, O and S, or a 7- to 12-membered saturated or partially saturated bicyclic ring system having 1-6 heteroatoms selected from N, O and S. Representative examples include piperidinyl, piperazinyl, azepanyl, pyrrolidinyl, pyrazolidinyl, imidazolidinyl, oxazolidinyl, isoxazolidinyl, morpholinyl, thiomorpholinyl, thiazolidinyl, isothiazolidinyl, and tetrahydrofuryl (or tetrahydrofuranyl).

Except where noted herein, the term "carbocycle" (and variations thereof such as "carbocyclic" or "carbocyclyl") as used herein, unless otherwise indicated, refers to a $C_3$ to $C_8$ monocyclic saturated or unsaturated ring, e.g., $C_{3-8}$ carbocycle. The carbocycle may be attached to the rest of the molecule at any carbon atom which results in a stable compound. Saturated carbocyclic rings are also referred to as "cycloalkyl" rings, e.g., cyclopropyl, cyclobutyl, etc.

Except where noted herein, aryl groups and carbocycle groups may be unsubstituted, or substituted on any one or more carbon atoms, with halogen, $C_1$-$C_{20}$ alkyl, $CF_3$, $NH_2$, —$NH(C_1$-$C_6$ alkyl), —$N(C_1$-$C_6$ alkyl)$_2$, $NO_2$, oxo, CN, $N_3$, —OH, —$O(C_1$-$C_6$ alkyl), $C_3$-$C_{10}$ cycloalkyl, $C_2$-$C_6$ alkenyl, $C_2$-$C_6$ alkynyl, $HS(O)_{0-2}$—, ($C_1$-$C_6$ alkyl)$S(O)_{0-2}$—, ($C_1$-$C_6$ alkyl)$S(O)_{0-2}(C_1$-$C_6$ alkyl)-, $HS(O)_{0-2}(C_1$-$C_6$ alkyl)-, ($C_1$-$C_6$ alkyl)$S(O)_{0-2}$—, ($C_1$-$C_6$ alkyl)C(O)NH—, HC(O)NH—, $H_2N$—C(NH)—, —$O(C_1$-$C_6$ alkyl)$CF_3$, ($C_1$-$C_6$ alkyl)C(O)—, HC(O)—, ($C_1$-$C_6$ alkyl)OC(O)—, HOC(O)—, ($C_1$-$C_6$ alkyl)O($C_1$-$C_6$ alkyl)-, HO($C_1$-$C_6$ alkyl)-, ($C_1$-$C_6$ alkyl)$C(O)_{1-2}(C_1$-$C_6$ alkyl)-, ($C_1$-$C_6$ alkyl)$C(O)_{1-2}$—, $HC(O)_{1-2}(C_1$-$C_6$ alkyl)-, ($C_1$-$C_6$ alkyl)OC(O)NH—, HOC(O)NH—, aryl, aralkyl, heterocycle, heterocyclylalkyl, halo-aryl, halo-aralkyl, halo-heterocycle, halo-heterocyclylalkyl, cyano-aryl, cyano-aralkyl, cyano-heterocycle and cyano-heterocyclylalkyl, where such substitution results in formation of a stable compound.

Except where noted herein, heterocycles may be unsubstituted, or substituted on any one or more carbon atoms, with halogen, $C_1$-$C_{20}$ alkyl, $CF_3$, $NH_2$, —$NH(C_1$-$C_6$ alkyl), —$N(C_1$-$C_6$ alkyl)$_2$, $NO_2$, oxo, CN, $N_3$, —OH, —$O(C_1$-$C_6$ alkyl), $C_3$-$C_{10}$ cycloalkyl, $C_2$-$C_6$ alkenyl, $C_2$-$C_6$ alkynyl, ($C_1$-$C_6$ alkyl)$S(O)_{0-2}$—, $HS(O)_{0-2}$, ($C_1$-$C_6$ alkyl)$S(O)_{0-2}(C_1$-$C_6$ alkyl)-, $HS(O)_{0-2}(C_1$-$C_6$ alkyl)-, ($C_1$-$C_6$ alkyl)$S(O)_{0-2}$—, ($C_1$-$C_6$ alkyl)C(O)NH—, HC(O)NH—, $H_2N$—C(NH)—, —$O(C_1$-$C_6$ alkyl)$CF_3$, HC(O)—, ($C_1$-$C_6$ alkyl)C(O)—, ($C_1$-$C_6$ alkyl)OC(O)—, HOC(O)—, ($C_1$-$C_6$ alkyl)O($C_1$-$C_6$ alkyl)-, HO($C_1$-$C_6$ alkyl)-, ($C_1$-$C_6$ alkyl)O—, ($C_1$-$C_6$ alkyl)$C(O)_{1-2}(C_1$-$C_6$ alkyl)-, $HC(O)_{1-2}(C_1$-$C_6$ alkyl)-, ($C_1$-$C_6$ alkyl)$C(O)_{1-2}$, ($C_1$-$C_6$ alkyl)OC(O)NH—, HOC(O)NH—, silyl groups (including trimethylsilyl, tetramethylsilyl, or supersilyl groups such as tri(trimethylsilyl)silyl or a silicon group connected to tert butyl groups), aryl, aralkyl, heterocycle, heterocyclylalkyl, halo-aryl, halo-aralkyl, halo-heterocycle, halo-heterocyclylalkyl, cyano-aryl, cyano-aralkyl, cyano-heterocycle or cyano-heterocyclylalkyl, or independently or additionally substituted with 1 substituent on any one or more nitrogen atoms, with $C_1$-$C_{20}$ alkyl, oxo, $C_3$-$C_{10}$ cycloalkyl, $C_2$-$C_6$ alkenyl, $C_2$-$C_6$ alkynyl, aryl, —C(O)$C_{1-6}$ alkyl, —C(O)NH$C_1$-$C_6$ alkyl, —C(O) $NH_2$, —$C_1$-$C_6$ alkylC(O)$NH_2$, —$C_1$-$C_6$ alkylOC(O)$NH_2$, or independently or additionally substituted with 1 substituent on any one or more sulfur atoms, with $C_1$-$C_{20}$ alkyl, oxo, $C_3$-$C_{10}$cycloalkyl, $C_2$-$C_6$ alkenyl, $C_2$-$C_6$ alkynyl, aryl, where such substitution results in formation of a stable compound.

Except where noted herein, structures containing substituent variables such as variable "R" below:

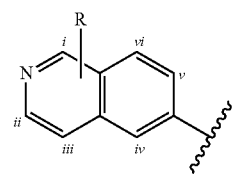

which are depicted as not being attached to any one particular bicyclic ring carbon atom, represent structures in which the variable can be optionally attached to any bicyclic ring carbon atom. For example, variable R shown in the above structure can be attached to any one of 6 bicyclic ring carbon atoms i, ii, iii, iv, v or vi.

The invention also includes derivatives of the compound of Formula I, acting as prodrugs. Prodrugs, following administration to the patient, are converted in the body by normal metabolic or chemical processes, such as through hydrolysis in the blood, to the compound of Formula I. Such prodrugs include those that demonstrate enhanced bioavailability, tissue specificity, and/or cellular delivery, to improve drug absorption of the compound of Formula I. The effect of such prodrugs may result from modification of physicochemical properties such as lipophilicity, molecular weight, charge, and other physicochemical properties that determine the permeation properties of the drug.

The preparation of pharmacologically acceptable salts from compounds of the Formula (I) capable of salt formation, including their stereoisomeric forms is carried out in a manner known per se. With basic reagents such as hydroxides, carbonates, hydrogencarbonates, alkoxides and ammonia or organic bases, for example, trimethyl- or triethylamine, ethanolamine, diethanolamine or triethanolamine, trometamol or alternatively basic amino acids, for example lysine, ornithine or arginine, the compounds of the Formula (I) form stable alkali metal, alkaline earth metal or optionally substituted ammonium salts. If the compounds of the Formula (I) have basic groups, stable acid addition salts can also be prepared using strong acids. For this, inorganic and organic acids such as hydrochloric, hydrobromic, sulfuric, hemisulfuric, phosphoric, methanesulfonic, benzenesulfonic, p-toluenesulfonic, 4-bromobenzenesulfonic, cyclohexylamidosulfonic, trifluoromethylsulfonic, 2-hydroxyethanesulfonic, acetic, oxalic, tartaric, succinic, glycerolphosphoric, lactic, malic, adipic, citric, fumaric, maleic, gluconic, glucuronic, palmitic or trifluoroacetic acid are suitable.

The invention also relates to medicaments containing at least one compound of the Formula (I) and/or of a pharmaceutically acceptable salt of the compound of the Formula (I) and/or an optionally stereoisomeric form of the compound of the Formula (I) or a pharmaceutically acceptable salt of the stereoisomeric form of the compound of Formula (I), together with a pharmaceutically suitable and pharmaceutically acceptable vehicle, additive and/or other active substances and auxiliaries.

Anticoagulant therapy is indicated for the treatment and prevention of a variety of thrombotic conditions, particularly coronary artery and cerebrovascular disease. Those experienced in this field are readily aware of the circumstances requiring anticoagulant therapy. The term "patient" used herein is taken to mean mammals such as primates, including humans, sheep, horses, cattle, pigs, dogs, cats, rats, and mice.

Factor IXa inhibition is useful not only in the anticoagulant therapy of individuals having thrombotic conditions, but is useful whenever inhibition of blood coagulation is required such as to prevent coagulation of stored whole blood and to prevent coagulation in other biological samples for testing or storage. Thus, the Factor IXa inhibitors can be added to or contacted with any medium containing or suspected of containing thrombin and in which it is desired that blood coagulation be inhibited, e.g., when contacting the mammal's blood with material selected from the group consisting of vascular grafts, stents, orthopedic prosthesis, cardiac prosthesis, and extracorporeal circulation systems.

Compounds of the invention may be useful for treating or preventing venous thromboembolism (e.g., obstruction or occlusion of a vein by a detached thrombus; obstruction or occlusion of a lung artery by a detached thrombus), cardiogenic thromboembolism (e.g., obstruction or occlusion of the heart by a detached thrombus), arterial thrombosis (e.g., formation of a thrombus within an artery that may cause infarction of tissue supplied by the artery), atherosclerosis (e.g., arteriosclerosis characterized by irregularly distributed lipid deposits) in mammals, and for lowering the propensity of devices that come into contact with blood to clot blood.

Examples of venous thromboembolism which may be treated or prevented with compounds of the invention include obstruction of a vein, obstruction of a lung artery (pulmonary embolism), deep vein thrombosis, thrombosis associated with cancer and cancer chemotherapy, thrombosis inherited with thrombophilic diseases such as Protein C deficiency, Protein S deficiency, antithrombin III deficiency, and Factor V Leiden, and thrombosis resulting from acquired thrombophilic disorders such as systemic lupus erythematosus (inflammatory connective tissue disease). Also with regard to venous thromboembolism, compounds of the invention may be useful for maintaining patency of indwelling catheters.

Examples of cardiogenic thromboembolism which may be treated or prevented with compounds of the invention include thromboembolic stroke (detached thrombus causing neurological affliction related to impaired cerebral blood supply), cardiogenic thromboembolism associated with atrial fibrillation (rapid, irregular twitching of upper heart chamber muscular fibrils), cardiogenic thromboembolism associated with prosthetic heart valves such as mechanical heart valves, and cardiogenic thromboembolism associated with heart disease.

Examples of arterial thrombosis include unstable angina (severe constrictive pain in chest of coronary origin), myocardial infarction (heart muscle cell death resulting from insufficient blood supply), ischemic heart disease (local anemia due to obstruction (such as by arterial narrowing) of blood supply), reocclusion during or after percutaneous transluminal coronary angioplasty, restenosis after percutaneous transluminal coronary angioplasty, occlusion of coronary artery bypass grafts, and occlusive cerebrovascular disease. Also with regard to arterial thrombosis, compounds of the invention may be useful for maintaining patency in arteriovenous cannulas.

Examples of atherosclerosis include arteriosclerosis.

Examples of devices that come into contact with blood include vascular grafts, stents, orthopedic prosthesis, cardiac prosthesis, and extracorporeal circulation systems The medicaments according to the invention can be administered by oral, inhalative, rectal or transdermal administration or by subcutaneous, intraarticular, intraperitoneal or intravenous injection. Oral administration is preferred. Coating of stents with compounds of the Formula (I) and other surfaces which come into contact with blood in the body is possible.

The invention also relates to a process for the production of a medicament, which comprises bringing at least one compound of the Formula (I) into a suitable administration form using a pharmaceutically suitable and pharmaceutically acceptable carrier and optionally further suitable active substances, additives or auxiliaries.

Suitable solid or galenical preparation forms are, for example, granules, powders, coated tablets, tablets, (micro) capsules, suppositories, syrups, juices, suspensions, emulsions, drops or injectable solutions and preparations having prolonged release of active substance, in whose preparation customary excipients such as vehicles, disintegrants, binders, coating agents, swelling agents, glidants or lubricants, flavorings, sweeteners and solubilizers are used. Frequently used auxiliaries which may be mentioned are magnesium carbonate, titanium dioxide, lactose, mannitol and other sugars, talc, lactose, gelatin, starch, cellulose and its derivatives, animal and plant oils such as cod liver oil, sunflower, peanut or sesame oil, polyethylene glycol and solvents such as, for example, sterile water and mono- or polyhydric alcohols such as glycerol.

The dosage regimen utilizing the Factor IXa inhibitors is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Oral dosages of the Factor IXa inhibitors, when used for the indicated effects, will range between about 0.01 mg per kg of body weight per day (mg/kg/day) to about 30 mg/kg/day, preferably 0.025-7.5 mg/kg/day, more preferably 0.1-2.5 mg/kg/day, and most preferably 0.1-0.5 mg/kg/day (unless specified otherwise, amounts of active ingredients are on free base basis). For example, an 80 kg patient would receive between about 0.8 mg/day and 2.4 g/day, preferably 2-600 mg/day, more preferably 8-200 mg/day, and most preferably 8-40 mg/kg/day. A suitably prepared medicament for once a day administration would thus contain between 0.8 mg and 2.4 g, preferably between 2 mg and 600 mg, more preferably between 8 mg and 200 mg, and most preferably 8 mg and 40 mg, e.g., 8 mg, 10 mg, 20 mg and 40 mg. Advantageously, the Factor IXa inhibitors may be administered in divided doses of two, three, or four times daily. For administration twice a day, a suitably prepared medicament would contain between 0.4 mg and 4 g, preferably between 1 mg and 300 mg, more preferably between 4 mg and 100 mg, and most preferably 4 mg and 20 mg, e.g., 4 mg, 5 mg, 10 mg and 20 mg.

Intravenously, the patient would receive the active ingredient in quantities sufficient to deliver between 0.025-7.5 mg/kg/day, preferably 0.1-2.5 mg/kg/day, and more preferably 0.1-0.5 mg/kg/day. Such quantities may be administered in a number of suitable ways, e.g. large volumes of low concentrations of active ingredient during one extended period of time or several times a day, low volumes of high concentrations of active ingredient during a short period of time, e.g. once a day. Typically, a conventional intravenous formulation may be prepared which contains a concentration of active ingredient of between about 0.01-1.0 mg/ml, e.g. 0.1 mg/ml, 0.3 mg/ml, and 0.6 mg/ml, and administered in amounts per day of between 0.01 ml/kg patient weight and 10.0 ml/kg patient weight, e.g. 0.1 ml/kg, 0.2 ml/kg, 0.5 ml/kg. In one example, an 80 kg patient, receiving 8 ml twice a day of an intravenous formulation having a concentration of active ingredient of 0.5 mg/ml, receives 8 mg of active ingredient per day. Glucuronic acid, L-lactic acid, acetic acid, citric acid or any pharmaceutically acceptable acid/conjugate base with reasonable buffering capacity in the pH range acceptable for intravenous administration may be used as buffers. The choice of appropriate buffer and pH of a formulation, depending on solubility of the drug to be administered, is readily made by a person having ordinary skill in the art.

The effectiveness of compounds of the present invention to inhibit the coagulation factors XIa, VIIa, IXa, Xa, plasma kallikrein or thrombin, can be determined using a relevant purified serine protease, respectively, and an appropriate synthetic substrate.

Methods for Making the Compounds of Present Invention
General Methods

The compounds of the present invention can be readily produced from known compounds or commercially available compounds by, for example, known processes described in published documents, and produced by production processes described below. The present invention is not limited to the production processes described below. The invention also includes processes for the preparation of compounds of the invention.

It should be noted that, when compounds of the present invention synthesized has a reactive group such as hydroxy group, amino group, carboxyl group, or thiol group as its substituent, such group may be adequately protected with a protective group in each reaction step and the protective group may be removed at an adequate stage. The process of such introduction and removal of the protective group may be adequately determined depending on the group to be protected and the type of the protective group, and such introduction and removal are conducted, for example, by the process described in the review section of Greene, T. W., et. al., "*Protective Groups in Organic Synthesis*", 2007, 4th Ed., Wiley, New York, or Kocienski, P., "*Protecting Groups*" 1994, Thieme.

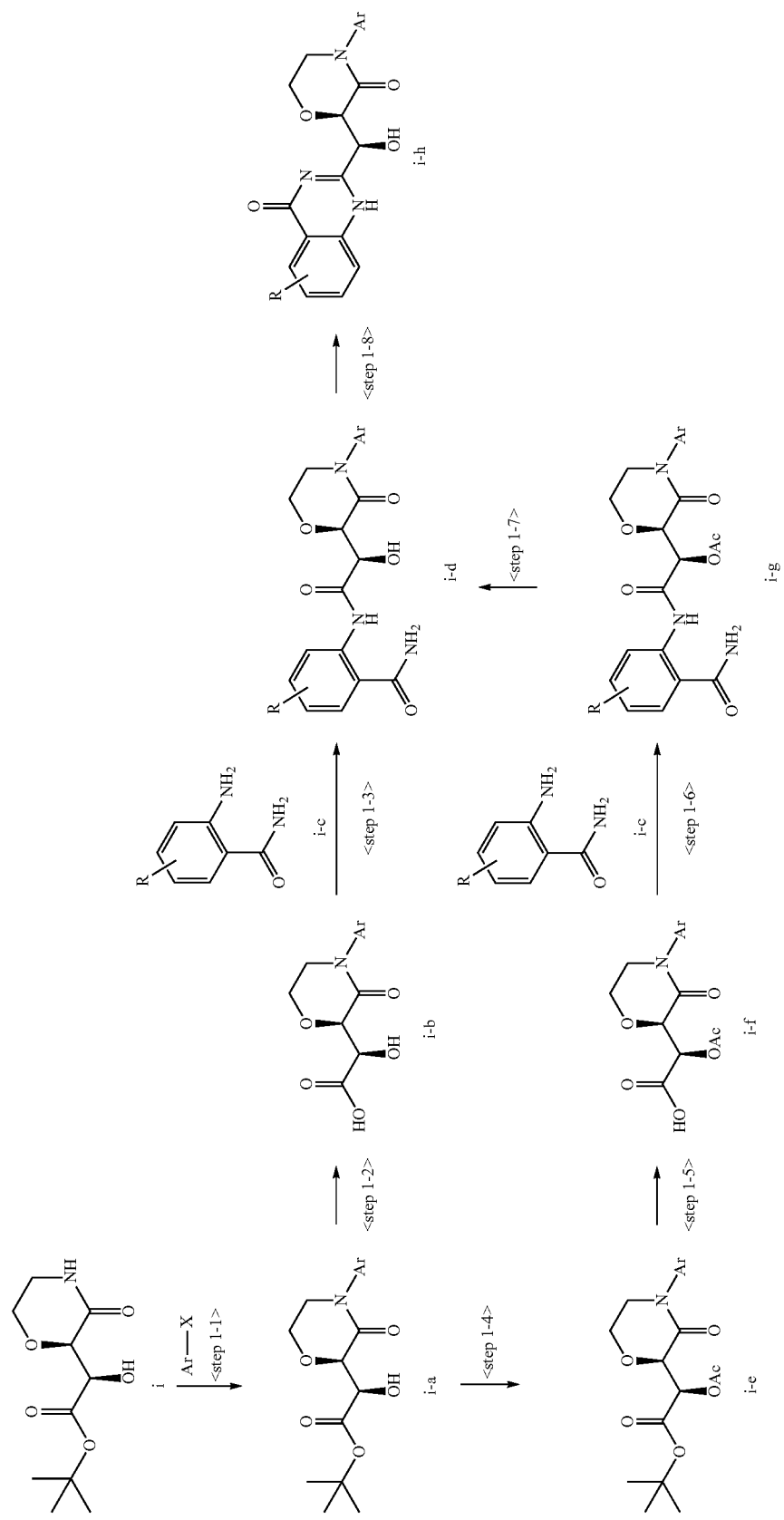
Scheme 1

<Step 1-1>

A compound represented by formula (i-a) can be produced by allowing a key intermediate compound represented by formula (i) to react with a compound represented by Ar—X (aryl halide or heteroaryl halide, wherein X represents halogen atom) by a process known as Goldberg reaction which are similar to that described in published documents, for example, *JACS*, 2002, 124, 7421 in the presence of a base such as potassium phosphate, cesium carbonate, potassium tert-butoxide, sodium hydride, lithium hydroxide, sodium hydroxide, potassium hydroxide, lithium carbonate, sodium carbonate, or potassium carbonate in the presence of 1,2-diamine ligand such as trans-1,2-cyclohexanediamine, trans-N,N'-dimethylcyclohexane-1,2-diamine, or ethylene diamine, and in the presence of catalytic amount of copper iodide using a solvent which is inactive to the reaction, such as an ethereal solvent, e.g., diethyl ether, tetrahydrofuran, 1,2-dimethoxyethane, 1,4-dioxane, polar solvents such as N,N-dimethylformamide, and dimethyl sulfoxide; or an aromatic hydrocarbon solvent, e.g., toluene or benzene or a mixed solvent thereof at a temperature in the range of room temperature to the solvent-reflux temperature.

<Step 1-2>

A compound represented by formula (i-b) can be produced from a compound represented by formula (i-a) by a well-known or similar process that described in published documents, for example, Jikken Kagaku Koza (Experimental Chemistry Series), 4th edition, 22, Organic synthesis IV, Acids, amino acids, and peptides, pp. 1-43, 1992, Maruzen Co., Ltd., in the presence of inorganic or organic acids such as hydrochloric, hydrobromic, sulfuric, hemisulfuric, phosphoric, methanesulfonic, benzenesulfonic, p-toluenesulfonic, 4-bromobenzenesulfonic, cyclohexylamidosulfonic, trifluoromethylsulfonic, 2-hydroxyethanesulfonic, acetic, oxalic, tartaric, succinic, glycerolphosphoric, lactic, malic, adipic, citric, fumaric, maleic, gluconic, glucuronic, palmitic or trifluoroacetic acid with water or without water and a solvent which is inactive to the reaction, such as methanol, ethanol, 2-propanol, N,N-dimethylformamide, dioxane, or tetrahydrofuran, or a mixed solvent thereof at a temperature in the range of 0° C. to the solvent-reflux temperature.

<Step 1-3>

A compound represented by formula (i-d) can be produced by allowing a compound represented by formula (i-b) to react with a compound represented by formula (i-c) by a process similar to that described in published documents, for example, Organic synthesis IV, Acids, amino acids, and peptides, pp. 191-309, 1992, Maruzen Co., Ltd., in the presence of a condensing agent such as 1,3-dicyclohexylcarbodiimide (DCC), 1-ethyl-3-(3'-dimethylaminopropyl)carbodiimide hydrochloride (WSC•HCl or EDC HCl), benzotriazol-1-yloxy tris(dimethylamino)phosphonium hexafluorophosphate (BOP reagent), bis(2-oxo-3-oxazolidinyl)phosphinic chloride (BOP-Cl), 2-chloro-1,3-dimethylimidazolinium hexafluorophosphate (CIP), or 4-(4,6-dimethoxy-1,3,5-triazin-2-yl)-4-methylmorpholinium chloride, in a solvent which is inactive to the reaction, such as a halogenated solvent, e.g., dichloromethane or chloroform, an ethereal solvent, e.g., diethyl ether or tetrahydrofuran, an aromatic hydrocarbon solvent, e.g., toluene or benzene, a polar solvent, e.g., N,N-dimethylformamide, or an alcoholic solvent, e.g., methanol, ethanol, or 2-propanol, in the presence or absence of a base such as triethylamine or pyridine at a temperature in the range of 0° C. to the solvent-reflux temperature. When a compound represented by formula (i-b) is converted to an acid halide, a compound represented by formula (i-c) (where R is e.g., pyrazole, =O or —C(=NH)NH$_2$) can be similarly produced by conducting a reaction by a process similar to that described in, for example, Organic synthesis IV, Acids, amino acids, and peptides, pp. 144-146, 1992, Maruzen Co., Ltd., in the presence of a base such as triethylamine or pyridine in a solvent which is inactive to the reaction, such as a halogenated solvent, e.g., dichloromethane or chloroform, an ethereal solvent, e.g., diethyl ether or tetrahydrofuran, an aromatic hydrocarbon solvent, e.g., toluene or benzene, or a polar solvent, e.g., N,N-dimethylformamide at a temperature in the range of 0° C. to the solvent-reflux temperature.

<Step 1-4>

A compound represented by formula (i-e) can be produced by allowing a compound represented by formula (i-a) to react with acetic anhydride or acetyl chloride by a process similar to that described in published documents, for example, Jikken Kagaku Koza (Experimental Chemistry Series), 4th edition, 22, Organic synthesis IV, Acids, amino acids, and peptides, pp. 191-309, 1992, Maruzen Co., Ltd.

<Step 1-5>

A compound represented by formula (i-f) can be produced by a similar process as that used in <Step 1-2> of (Reaction Scheme 2) using a compound represented by formula (i-e)

<Step 1-6>

A compound represented by formula (i-g) can be produced by a similar process as that used in <Step 1-3> of (Reaction Scheme 2) using a compound represented by formula (i-f) with a compound represented by formula (i-c).

<Step 1-7>

A compound represented by formula (i-d) can be produced by conducting a reaction using a compound represented by formula (i-g) by a process similar to that described in published documents, for example, *Can. J. Chem.*, 49, 493 (1971) or Greene, T. W., et. al., *Protective Groups in Organic Synthesis* (2007), 4th Ed., in the presence of ammonia or hydrazine, using a solvent which is inactive to the reaction, such as an alcoholic solvent, e.g., methanol, ethanol, or 2-propanol, a halogenated solvent, e.g., dichloromethane or chloroform, an ethereal solvent, e.g., diethyl ether, dioxane, or tetrahydrofuran, or a mixed solvent thereof at a temperature in the range of −78° C. to the room temperature.

<Step 1-8>

A compound represented by formula (i-h) can be produced by allowing a compound represented by formula (i-d) by a process similar to that described in published documents, for example, *European Journal of Medicinal Chemistry* 48, 231 (2012) or *Tetrahedron Asymmetry* 22, 300 (2011) in the presence of a base such as potassium tert-butoxide, sodium tert-butoxide, sodium methoxide, sodium hydride, lithium hydroxide, sodium hydroxide, potassium hydroxide, lithium carbonate, sodium carbonate, or potassium carbonate using a solvent which is inactive to the reaction, such as an alcoholic solvent, e.g., water, methanol, ethanol, 2-propanol, tert-butanol, or ethylene glycol, an ethereal solvent, e.g., diethyl ether, dioxane, or tetrahydrofuran, polar solvent, e.g., acetonitrile, N,N-dimethylformamide, or dimethyl sulfoxide, or a mixed solvent thereof at a temperature in the range of 0° C. to the solvent-reflux temperature.

Scheme 2
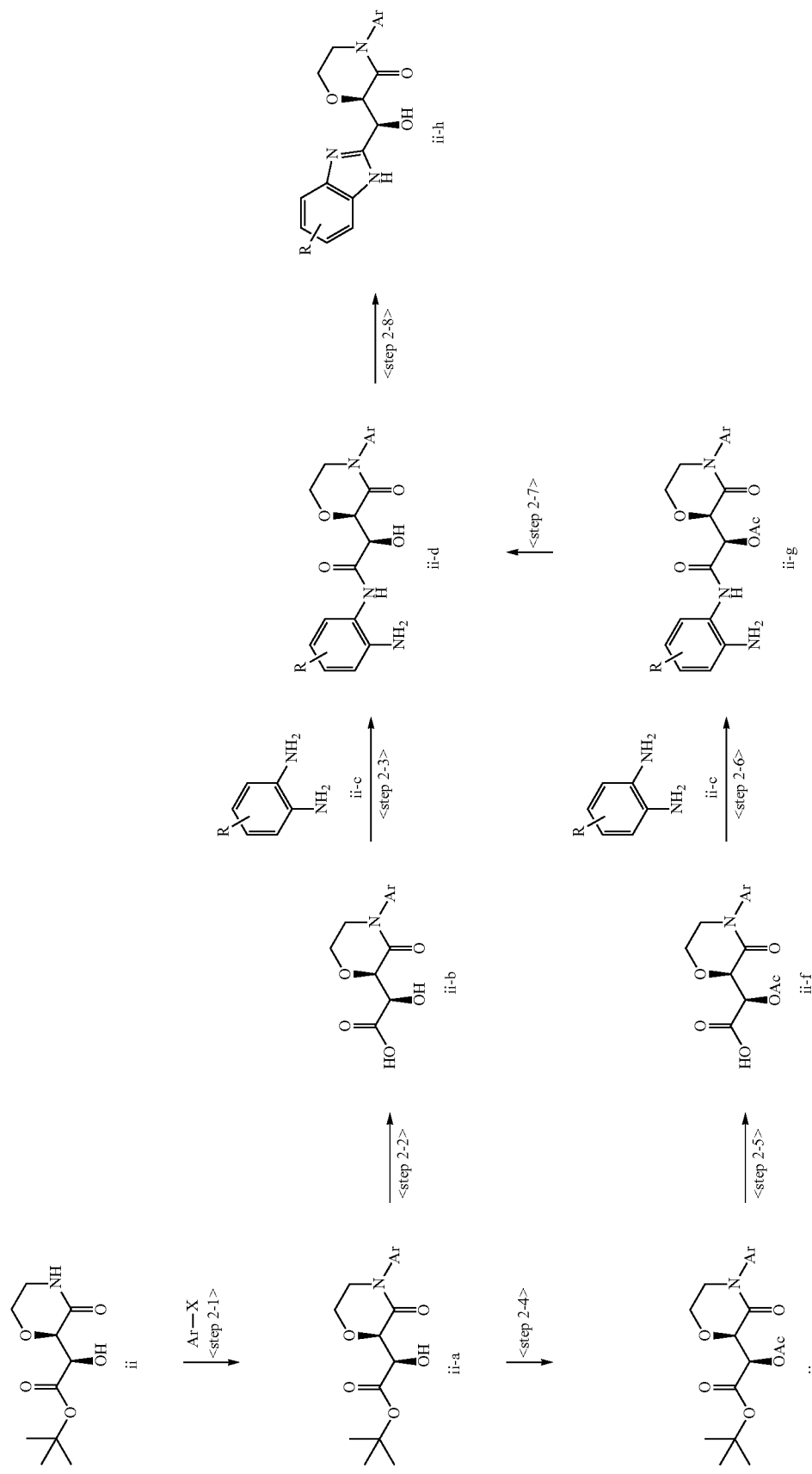

<Step 2-1>

A compound represented by formula (ii-a) can be produced by a similar process as that used in <Step 1-1> of (Reaction Scheme 1) using a compound represented by formula (ii) with a compound represented by Ar—X (aryl halide or heteroaryl halide, wherein X represents halogen atom).

<Step 2-2>

A compound represented by formula (ii-b) can be produced by a similar process as that used in <Step 1-2> of (Reaction Scheme 1) using a compound represented by formula (ii-a).

<Step 2-3>

A compound represented by formula (ii-d) can be produced by a similar process as that used in <Step 1-3> of (Reaction Scheme 1) by allowing a compound represented by formula (ii-b) to react with a compound represented by formula (ii-c) (R is, e.g., =O, —C(=NH)NH$_2$, or pyrazole).

<Step 2-4>

A compound represented by formula (ii-e) can be produced by a similar process as that used in <Step 1-4> of (Reaction Scheme 1) by allowing a compound represented by formula (ii-a) to react with acetic anhydride or acetyl chloride.

<Step 2-5>

A compound represented by formula (ii-f) can be produced by a similar process as that used in <Step 1-2> of (Reaction Scheme 1) using a compound represented by formula (ii-e)

<Step 2-6>

A compound represented by formula (ii-g) can be produced by a similar process as that used in <Step 1-3> of (Reaction Scheme 1) using a compound represented by formula (ii-f) with a compound represented by formula (ii-c).

<Step 2-7>

A compound represented by formula (ii-d) can be produced by a similar process as that used in <Step 1-7> of (Reaction Scheme 1) by conducting a reaction using a compound represented by formula (ii-g).

<Step 2-8>

A compound represented by formula (ii-h) can be produced by exposing a compound represented by formula (ii-d) to an acid such as acetic acid at a temperature in the range of 0° C. to the solvent-reflux temperature.

Scheme 3
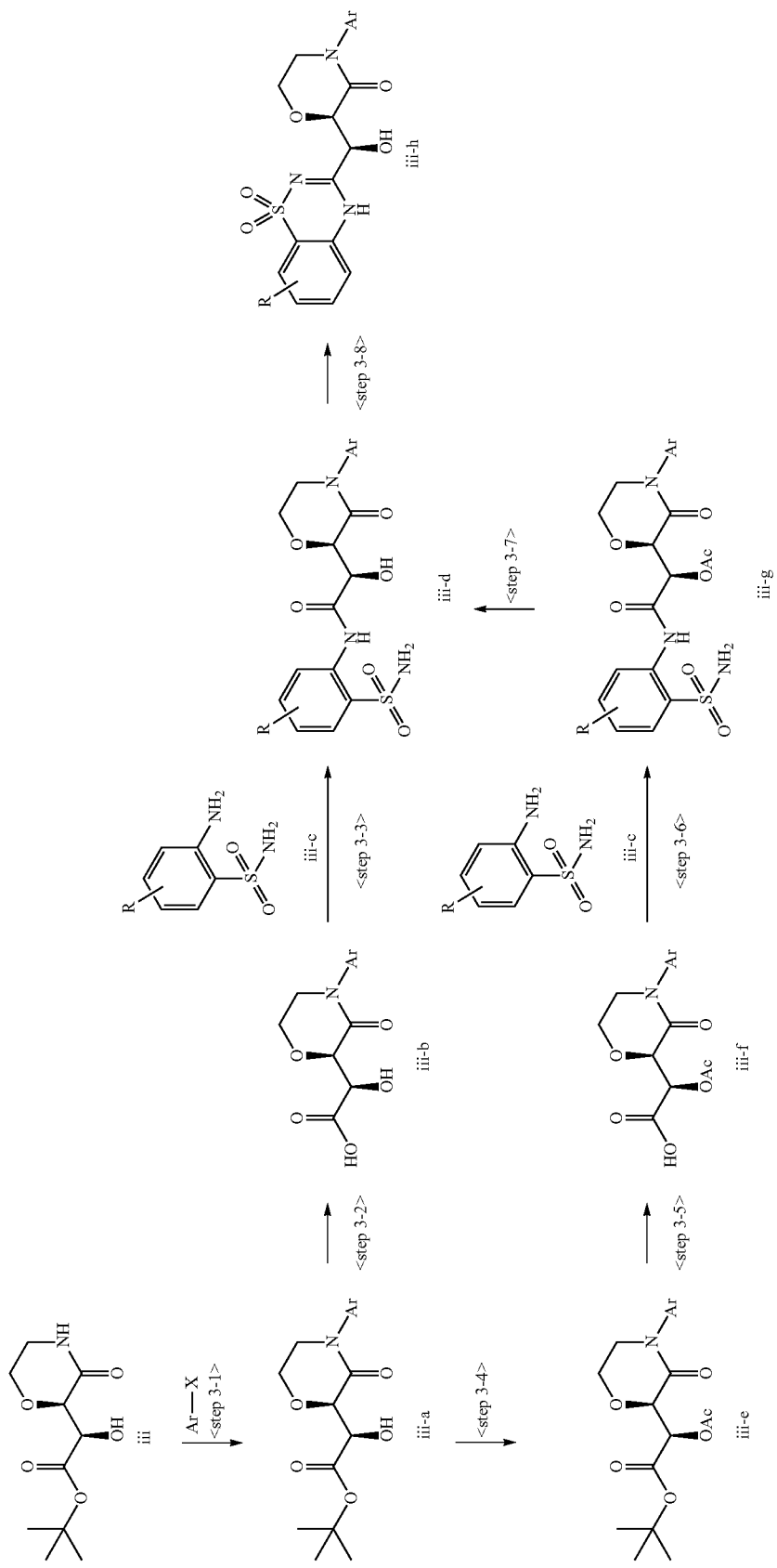

<Step 3-1>

A compound represented by formula (iii-a) can be produced by a similar process as that used in <Step 1-1> of (Reaction Scheme 1) using a compound represented by formula (iii) with a compound represented by Ar—X (aryl halide or heteroaryl halide, wherein X represents halogen atom).

<Step 3-2>

A compound represented by formula (iii-b) can be produced by a similar process as that used in <Step 1-2> of (Reaction Scheme 1) using a compound represented by formula (iii-a).

<Step 3-3>

A compound represented by formula (iii-d) can be produced by a similar process as that used in <Step 1-3> of (Reaction Scheme 1) by allowing a compound represented by formula (iii-b) to react with a compound represented by formula (iii-c)(R is e.g., =O, —C(=NH)NH₂, or pyrazole).

<Step 3-4>

A compound represented by formula (iii-e) can be produced by a similar process as that used in <Step 1-4> of (Reaction Scheme 1) by allowing a compound represented by formula (iii-a) to react with acetic anhydride or acetyl chloride.

<Step 3-5>

A compound represented by formula (iii-f) can be produced by a similar process as that used in <Step 1-2> of (Reaction Scheme 1) using a compound represented by formula (iii-e)

<Step 3-6>

A compound represented by formula (iii-g) can be produced by a similar process as that used in <Step 1-3> of (Reaction Scheme 1) using a compound represented by formula (iii-f) with a compound represented by formula (iii-c).

<Step 3-7>

A compound represented by formula (iii-d) can be produced by a similar process as that used in <Step 1-7> of (Reaction Scheme 1) by conducting a reaction using a compound represented by formula (iii-g).

<Step 3-8>

A compound represented by formula (iii-h) can be produced by exposing a compound represented by formula (iii-d) to an acid such as HCl in solvents such as 1,4-dioxane, or bases such as ammonium hydroxide at a temperature in the range of 0° C. to the solvent-reflux temperature.

Scheme 4

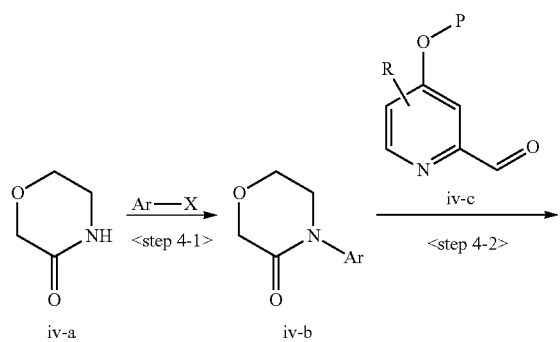

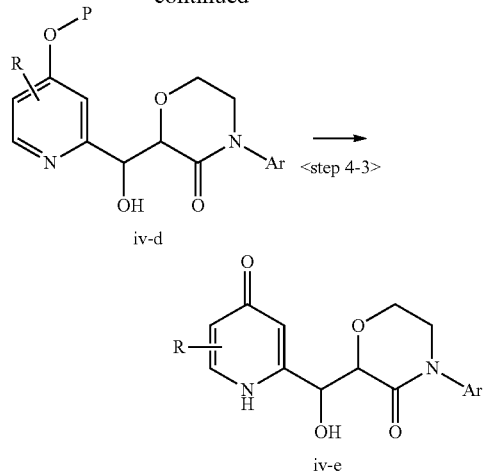

<Step 4-1>

A compound represented by formula (iv-b) can be produced by a similar process as that used in <Step 1-1> of (Reaction Scheme 1) using a compound represented by formula (iv-a) with a compound represented by Ar—X (aryl halide or heteroaryl halide, wherein X represents halogen atom).

<Step 4-2>

A compound represented by formula (iv-d) can be produced by allowing a compound represented by formula (iv-b) to react with a compound represented by formula (iv-c)(P is a protecting group; R is e.g., =O, —C(NH)NH₂, or pyrazole) by a process similar to that described in published documents, for example, *Journal of Medicinal Chemistry*, 31(1), pp. 230-243, 1988, in the presence of a base such as lithium hexamethyldisilazide, lithium diisopropylamide, sodium hydride, lithium hydroxide, sodium hydroxide, potassium hydroxide, lithium carbonate, sodium carbonate, or potassium carbonate using a solvent which is inactive to the reaction, such as tetrahydrofuran, N,N-dimethylformamide, dioxane, or a mixed solvent thereof at a temperature in the range of −78° C. to the solvent-reflux temperature.

<Step 4-3>

A compound represented by formula (iv-e) can be produced by allowing a compound represented by formula (iv-d) by a process similar to that described in published documents, for example, Greene, T. W., et. al., *Protective Groups in Organic Synthesis* (2007), 4th Ed., in the presence of DDQ (2,3-dichloro-5,6-dicyano-p-benzoquinone), CAN (ceric ammonium nitrate), AlCl₃, SnCl₄, BCl₃, BBr₃, TMSI, acetic acid, hydrochloric acid, trifluoromethane sulfonic acid, 10-camphorsulfonic, BF₃ Et₂O, or trifluoroacetic acid, using a solvent which is inactive to the reaction, such as an alcoholic solvent, e.g., water, methanol, ethanol, or 2-propanol, a halogenated solvent, e.g., dichloromethane or chloroform, an ethereal solvent, e.g., diethyl ether, dioxane, or tetrahydrofuran, an aromatic hydrocarbon solvent, e.g., toluene or benzene, polar solvent, e.g., acetonitrile, N,N-dimethylformamide, or dimethyl sulfoxide, acidic solvent, e.g., acetic acid, or trifluoroacetic acid, or a mixed solvent thereof at a temperature in the range of 0° C. to the solvent-reflux temperature.

The present invention will now be described in more detail using examples, but the present invention is not limited to the examples. Acronyms and abbreviations are as follows: acetic acid (AcOH); 1,1'-Bis(diphenylphosphino)ferrocene (dppf); 4-dimethylaminopyridine (DMAP); 1,2-dimethoxyethane (DME); dimethylsulfoxide (DMSO); dimethylformamide (DMF); ethanol (EtOH); ethyl acetate (EtOAc); lithium diisopropylamide (LDA); acetonitrile (MeCN); methanol (MeOH); N,N-diisopropylethylamine (Hünig's base) (DIEA/DIPEA); N,N-Dimethylacetamide (DMA); O-(7-Azabenzotriazol-1-yl)-N,N,N'N'-tetramethyluronium hexafluorophosphate (HATU); O-(Benzotriazole-1-yl)-1,1,3,3-tetramethyluronium hexafluorophosphate (HBTU); phenyl (Ph); tetrabutylammonium fluoride (TBAF); tetrahydrofuran (THF); trifluoroacetic acid (TFA); catalyst (cat.); anhydrous (anh.); concentrated (conc.); saturated (sat.); room temperature (RT). WSC·HCl·1-Ethyl-3-(3'-dimethylaminopropyl)carbodiimide•HCl. Celite is Celite® (Fluka) diatomite which is diatomaceous earth. Xantphos is 4,5-Bis(diphenylphosphino)-9,9-dimethylxanthene. The measurement of nuclear magnetic resonance (NMR) spectra was performed using a JEOL JNM-ECX300 FT-NMR (manufactured by JEOL Ltd.), a JEOL JNM-ECX400 FT-NMR (manufactured by JEOL Ltd.), or a Varian Unity INOVA AS500 or AS600 FT-NMR (manufactured by Varian). Liquid chromatography-mass spectrometry (LC-MS) was performed using a Waters FractionLynx MS system (manufactured by Waters Corporation) or a Waters Micromass ZQ Mass Spectrometer/Agilent 1100 system. A SunFire Column™ (4.6 mm×5 cm, 5 micron) (manufactured by Waters Corporation) was used as an analytical column. A Sunfire Column™ (19 mm×5 cm, 5 micron) (manufactured by Waters Corporation) was used as a preparative column. Methanol or MeCN and 0.05% aqueous acetic acid solution or 0.05% aqueous trifluoroacetic acid solution were used as the mobile phase. The analysis was performed under the following gradient conditions: Methanol or MeCN: 0.05% aqueous acetic acid solution or 0.05% aqueous trifluoroacetic acid solution=1:9 (0 min), 10:0 (5 min), and 10:0 (6 min). Liquid chromatography-mass spectrometry (UPLC-MS) was also performed using a ACQUITY UPLC+MS system (manufactured by Waters Corporation). A CAPCELL Pak® C18 MGIII-H (2.0 mm×5 cm, 3 micron) (manufactured by Shiseido Co., Ltd.) was used as an analytical column. Methanol and 0.05% aqueous trifluoroacetic acid solution were used as the mobile phase. The analysis was performed under the following gradient conditions: Methanol: 0.05% aqueous trifluoroacetic acid solution=5:95 (0 min), 95:5 (1 min), 95:5 (1.6 min), and 5:95 (2 min). The solvent systems are described as the followings: A indicates LCMS system and mobile phase is 0.05% aq. AcOH, B indicates LCMS system and mobile phase is 0.05% aq. TFA, C indicates UPLC-MS system and mobile phase is 0.05% aq. TFA.

EXAMPLE 1

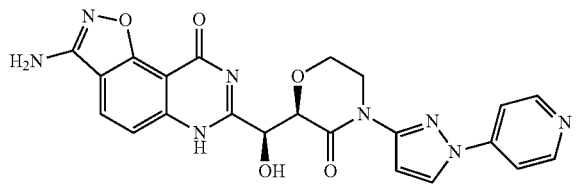 [SMILES: Nc1nsc2c1ccc1[nH]c([C@H](O)[C@H]3OCCN(c4ccn(-c5ccncc5)n4)C3=O)nc(=O)c12]

3-Amino-7-((S)-hydroxy((R)-3-oxo-4-(1-(pyridin-4-yl)-1H-pyrazol-3-yl)morpholin-2-yl)methyl)isoxazolo[5,4-f]quinazolin-9(6H)-one Step 1-1: 2-Amino-6-fluorobenzamide (Compound 1-1)

A solution of 2-amino-6-fluorobenzonitrile (10.0 g) in $H_2SO_4$ (75.0 mL) was stirred for 1.5 h at 65° C. Then the mixture was poured into ice and brought to pH=9 by 20% NaOH aqueous solution, followed by the extraction with ethyl acetate three times. The combined organic layer were washed with brine and dried over $Na_2SO_4$. It was filtered to remove insoluble matters and it was concentrated in vacuo to give compound 1-1 as a yellow solid.

Step 1-2: 6-Amino-2-fluoro-3-iodobenzamide (Compound 1-2)

To a suspension of $I_2$ (12.4 g) and $Ag_2SO_4$ (15.2 g) in EtOH (420 mL) was added compound 1-1 (7.50 g), and it was stirred for 1.5 h at room temperature. Then the reaction mixture was filtered with Celite® (Fluka) diatomite is diatomaceous earth. The filtrate was concentrated in vacuo to give a crude material of compound 1-2 as a pale brown solid, which was used in the next step without further purification.

Step 1-3: 6-Amino-3-cyano-2-fluorobenzamide (Compound 1-3)

A suspension of crude compound 1-2 (16.0 g) and CuCN (6.13 g) in pyridine (210 mL) was stirred for 20 h at 120° C. The reaction mixture was cooled to room temperature, and it was filtered with Celite® (Fluka) diatomite which is diatomaceous earth. The filtrate was concentrated in vacuo. The residue was purified by silica gel flash chromatography (eluent:Hexane:EtOAc=100:0~50:50) to give compound 1-3 as a yellow solid.

Step 1-4: 3,6-Diaminobenzo[d]isoxazole-7-carboxamide (Compound 1-4)

A suspension of compound 1-3 (2.30 g), acetohydroxamic acid (4.82 g) and $K_2CO_3$ (21.3 g) in DMF (60 mL)—water (30 mL) was stirred for 3 h at 60° C. The solvent was removed in vacuo. To the residue was added EtOAc and water, then the suspension was filtered to give a sticky solid. The sticky solid was triturated with EtOAc and MeOH to give compound 1-4 as a pale brown solid.

Step 1-5: 4-(3-Iodo-1H-pyrazol-1-yl)pyridine (Compound 1-5)

To a solution of 3-iodopyrazole (7.26 g) in DMSO (200 mL) was added NaH (1.80 g, 60% wt) at 0° C., and it was stirred for 15 min. To the reaction mixture was added mixture of 4-fluoropyridine (5.00 g) and NaH (1.80 g) in DMSO (175 mL) at room temperature. It was stirred for 2 h at 90° C. The reaction mixture was cooled to room temperature, and it was diluted with EtOAc and $H_2O$. The mixture was extracted with EtOAc (2 times), and the combined organic layer were washed with $H_2O$ and brine and dried over $Na_2SO_4$. It was filtered to remove insoluble matters and it was concentrated in vacuo. The residue was triturated with EtOAc to give compound 1-5 as a pale brown solid.

Step 1-6: (R)-tert-Butyl 2-hydroxy-2-((R)-3-oxo-4-(1-(pyridin-4-yl)-1H-pyrazol-3-yl)morpholin-2-yl)acetate (Compound 1-6)

To a suspension of CuI (90.6 mg) in DMSO (20 mL) was added trans-N,N'-Dimethylcyclohexane-1,2-diamine (0.15 mL) under Ar. The mixture was degassed under vacuum, filled with Ar, and it was stirred for 10 min. Then, to the reaction was added (R)-tert-butyl 2-hydroxy-2-((R)-3-oxo-morpholin-2-yl)acetate (1.10 g) and $K_3PO_4$ (2.02 g), and it was degassed. A solution of compound 1-5 (1.93 g) in DMSO (25 mL) was added to the reaction mixture, and it was stirred for 2 days at room temperature.

The reaction mixture was filtered with Celite® (Fluka) diatomite which is diatomaceous earth. The filtrate was diluted with EtOAc and $H_2O$. The mixture was extracted with EtOAc (2 times), and the combined organic layer was washed with $H_2O$ and brine and dried over $Na_2SO_4$. It was filtered to remove insoluble matters and it was concentrated in vacuo. The residue was purified by NH-silica gel flash chromatography (eluent:Hexane:EtOAc=100:0~10:90) to give compound 1-6 as a colorless solid.

Step 1-7: (R)-2-Hydroxy-2-((R)-3-oxo-4-(1-(pyridin-4-yl)-1H-pyrazol-3-yl)morpholin-2-yl)acetic acid hydrochloride (Compound 1-7)

A solution of compound 1-6 (0.40 g) in 4M HCl-dioxane (20 mL) was stirred for 15 h at room temperature. The organic solvent was evaporated under reduced pressure to afford the desired compound 1-7 as a colorless solid, which was used in the next step without further purification.

Step 1-8: 3-Amino-6-((R)-2-hydroxy-2-((R)-3-oxo-4-(1-(pyridin-4-yl)-1H-pyrazol-3-yl)morpholin-2-yl)acetamido)benzo[d]isoxazole-7-carboxamide (Compound 1-8)

To a suspension of compound 1-7 (0.35 g) and 1-4 (0.28 g) in DMF (14 mL) was added WSC-HCl (0.57 g) and HOAt (0.13 g). The solution was stirred for 17 h at room temperature. It was diluted with sat. $NaHCO_3$ aq. and extracted with EtOAc. The organic layer was washed with $H_2O$ and brine, dried over $Na_2SO_4$, filtered and concentrated. The residue was dissolved in MeOH, then the solution was precipitated by adding EtOAc. The precipitates were collected to give compound 1-8 as a beige solid.

Step 1-9: 3-Amino-7-((S)-hydroxy((R)-3-oxo-4-(1-(pyridin-4-yl)-1H-pyrazol-3-yl)morpholin-2-yl)methyl)isoxazolo[5,4-f]quinazolin-9(6H)-one (EXAMPLE 1)

A suspension of compound 1-8 (20 mg, 0.04 mmol) in 0.1 M NaOH-EtOH (5 mL) was stirred for 3 h at room temperature. To the reaction mixture was added water, then insoluble matter was collected to give EXAMPLE 1 as a pale beige solid.

EXAMPLE 2

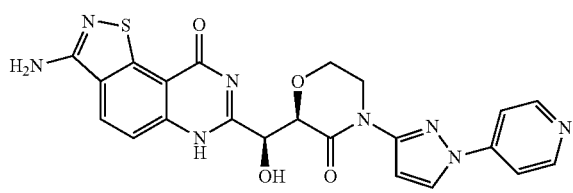

(R)-2-((S)-(3-Amino-9-oxo-6,9-dihydroisothiazolo[5,4-f]quinazolin-7-yl)(hydroxy)methyl)-4-(1-(pyridin-4-yl)-1H-pyrazol-3-yl)morpholin-3-one

Step 2-1: 3,6-Diaminobenzo[d]isothiazole-7-carboxamide (Compound 2-1)

Compound 1-3 (0.40 g), sulfur (0.14 g), 25% ammonium hydroxide (2.2 mL) and 2-methoxyethanol (6.7 mL) were all taken into a sealed tube. The reaction was heated to 135° C. for 15 h. The reaction was allowed to cool down to room temperature and diluted with water and extracted with EtOAc. The organic layer was dried over $Na_2SO_4$. Aqueous layer was concentrated in vacuo. And both crude mixture were purified by column chromatography on silica gel (Hexane:EtOAc=2:1 to EtOAc). The eluted mixture was purified again by column chromatography on silica gel using a gradient of 1-5% MeOH in $CH_2Cl_2$ to give compound 2-1 as a yellow solid.

Step 2-2: 6-Amino-3-(1,3-dioxoisoindolin-2-yl)benzo[d]isothiazole-7-carboxamide (Compound 2-2)

To a suspension of compound 2-1 (78 mg) in pyridine (3.7 mL), was added phthaloyl chloride (64.4 uL) under ice cooling and the reaction mixture was stirred at room temperature overnight. The reaction mixture was diluted with water and was extracted with EtOAc. The extract was washed with brine and dried over $Na_2SO_4$. It was filtrated to remove insoluble matters and it was concentrated in vacuo. The residue was triturated with diethyl ether to give compound 2-2 as a yellow solid.

Step 2-3: (R)-tert-Butyl 2-acetoxy-2-((R)-3-oxo-4-(1-(pyridin-4-yl)-1H-pyrazol-3-yl)morpholin-2-yl)acetate (Compound 2-3)

To a solution of compound 1-6 (8.6 g) and DMAP (0.28 g) in $CH_2Cl_2$ (115 mL) were added pyridine (3.7 mL) and acetic anhydride (4.3 mL) at 0° C. and stirred at room temperature overnight. The reaction mixture was quenched with water and was extracted with $CH_2Cl_2$. The extract was washed with sat.$NaHCO_3$ and brine, and dried over anhyd. $Na_2SO_4$. It was filtered to remove insoluble matters and concentrated in vacuo. Remaining impurities were azeotropically removed with toluene and EtOAc to give compound 2-3.

Step 2-4: (R)-2-Acetoxy-2-((R)-3-oxo-4-(1-(pyridin-4-yl)-1H-pyrazol-3-yl)morpholin-2-yl)acetic acid hydrochloride (Compound 2-4)

According to Step 1-7 in the synthetic method for EXAMPLE 1, compound 2-3 (9.4 g) was used instead of compound 1-6 to obtain compound 2-4 as a colorless solid.

Step 2-5: (R)-2-((7-Carbamoyl-3-(1,3-dioxoisoindolin-2-yl)benzo[d]isothiazol-6-yl)amino)-2-oxo-1-((R)-3-oxo-4-(1-(pyridin-4-yl)-1H-pyrazol-3-yl)morpholin-2-yl)ethyl acetate (Compound 2-5)

To a suspension of 2-4 (90 mg) in $CH_2Cl_2$ (2.3 mL) were added DMF (catalytic amount) and oxalyl chloride (58.4 uL) at 0° C. and stirred at room temperature for 30 min. The reaction mixture was concentrated and dissolved in $CH_2Cl_2$ (2.3 mL) again, and added dropwise to a solution of 2-2 (51 mg) and DMAP (5.5 mg) in pyridine (2.3 mL) at 0° C. The mixture was stirred at room temperature overnight. The reaction mixture was quenched with water and added sat-.NaHCO$_3$, extracted with CH$_2$Cl$_2$. The extract was washed with and brine, and dried with anhyd. Na$_2$SO$_4$. It was filtrated to remove insoluble matters and it was concentrated in vacuo. The residue was purified by silica gel flash chromatography (eluent:CH$_2$Cl$_2$:MeOH=99:1~96:4) to obtain compound 2-5 as a yellow solid.

Step 2-6: (R)-2-((S)-(3-Amino-9-oxo-6,9-dihydroisothiazolo[5,4-f]quinazolin-7-yl)(hydroxy)methyl)-4-(1-(pyridin-4-yl)-1H-pyrazol-3-yl)morpholin-3-one To a solution of compound 2-5 (16 mg) in CH$_2$Cl$_2$ (1 mL) and MeOH (1 mL) was added hydrazine hydrate (22.9 uL), and it was stirred at room temperature overnight.

The reaction mixture was diluted with water and CH$_2$Cl$_2$, and the precipitated solid was filtered and dried. The solid was dissolved in 0.1M EtOH solution of NaOH (3 mL) and stirred at room temperature for 2 h. The reaction mixture was diluted with water and was extracted with EtOAc. The extract was washed with brine and dried over Na$_2$SO$_4$. It was filtrated to remove insoluble matters and concentrated in vacuo to obtain EXAMPLE 2 as a pale yellow solid.

EXAMPLE 3

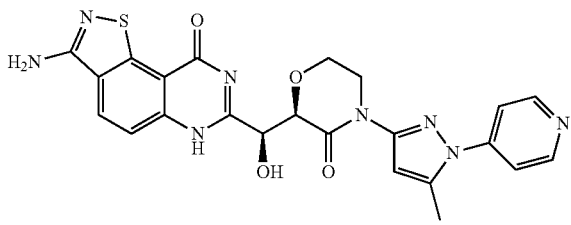 [SMILES: Cc1cc(N2CCO[C@H]([C@@H](O)c3nc(=O)c4c(ccc5c(N)nsc54)[nH]3)C2=O)nn1-c1ccncc1]

(R)-2-((S)-(3-Amino-9-oxo-6,9-dihydroisothiazolo[5,4-f]quinazolin-7-yl)(hydroxy)methyl)-4-(5-methyl-1-(pyridin-4-yl)-1H-pyrazol-3-yl)morpholin-3-one Step 3-1: 4-(3-Iodo-5-methyl-1H-pyrazol-1-yl)pyridine (Compound 3-1)

According to Step 1-5 in the synthetic method for EXAMPLE 1,3-iodo-5-methylpyrazole (3.5 g) was used instead of 3-iodopyrazole to obtain compound 3-1 as a pale yellow solid.

Step 3-2: (R)-tert-Butyl 2-hydroxy-2-((R)-4-(5-methyl-1-(pyridin-4-yl)-1H-pyrazol-3-yl)-3-oxomorpholin-2-yl)acetate (Compound 3-2)

According to Step 1-6 in the synthetic method for EXAMPLE 1, compound 3-1 (2.1 g) was used instead of compound 1-5 to obtain compound 3-2 as a solid.

Step 3-3: (R)-tert-Butyl 2-acetoxy-2-((R)-4-(5-methyl-1-(pyridin-4-yl)-1H-pyrazol-3-yl)-3-oxomorpholin-2-yl)acetate (Compound 3-3)

According to Step 2-3 in the synthetic method for EXAMPLE 2, compound 3-2 (0.60 g) was used instead of compound 1-6 to obtain compound 3-3 as a solid.

Step 3-4: (R)-2-Acetoxy-2-((R)-4-(5-methyl-1-(pyridin-4-yl)-1H-pyrazol-3-yl)-3-oxomorpholin-2-yl) acetic acid hydrochloride (Compound 3-4)

According to Step 1-7 in the synthetic method for EXAMPLE 1, compound 3-3 (0.46 g) was used instead of compound 1-6 to obtain compound 3-4 as a colorless solid.

Step 3-5: (1R)-2-((7-carbamoyl-3-(1,3-dioxoisoindolin-2-yl)benzo[d]isothiazol-6-yl)amino)-1-(4-(5-methyl-1-(pyridin-4-yl)-1H-pyrazol-3-yl)-3-oxomorpholin-2-yl)-2-oxoethyl acetate (Compound 3-5)

According to Step 2-5 in the synthetic method for EXAMPLE 2, compound 3-4 (0.11 g) was used instead of compound 2-4 to obtain compound 3-5 as a yellow solid.

Step 3-6: (R)-2-((S)-(3-Amino-9-oxo-6,9-dihydroisothiazolo[5,4-f]quinazolin-7-yl)(hydroxy)methyl)-4-(5-methyl-1-(pyridin-4-yl)-1H-pyrazol-3-yl)morpholin-3-one According to Step 2-6 in the synthetic method for EXAMPLE 2, compound 3-5 (22 mg) was used instead of compound 2-5 to obtain EXAMPLE 3 as a pale solid.

EXAMPLE 4

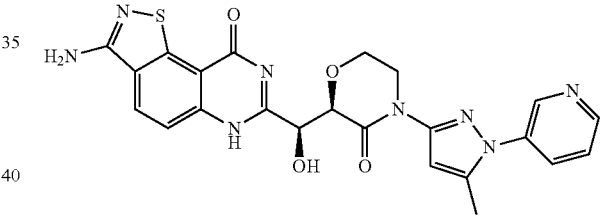

(R)-2-((S)-(3-Amino-9-oxo-6,9-dihydroisothiazolo[5,4-f]quinazolin-7-yl)(hydroxy)methyl)-4-(5-methyl-1-(pyridin-3-yl)-1H-pyrazol-3-yl)morpholin-3-one Step 4-1: 3-(3-Iodo-5-methyl-1H-pyrazol-1-yl)pyridine (Compound 4-1)

To a solution of 2,2'-bipyridyl (1.88 g) and Cu(OAc)$_2$ (2.18 g) in dichloroethane (30 mL) was added a suspension of 5-iodo-3-methylpyrazole (2.50 g), 3-pyridineboronic acid (2.75 g) and Na$_2$CO$_3$ (2.55 g) in dichloroethane (40 mL). The reaction mixture was stirred for 16 h at 70° C. under oxygen atmosphere. The reaction mixture was cooled to room temperature, then 8M NH$_3$-MeOH was added to the reaction. The mixture was filtered with Celite® (Fluka) diatomite which is diatomaceous earth, and the filtrate was concentrated in vacuo. The residue was purified by NH-silica gel flash chromatography (eluent:Hexane:EtOAc=95:5~85:15), then silica gel flash chromatography (eluent: Hexane:EtOAc=95:5~60:40) to give compound 4-1 as a yellow oil Step 4-2: (R)-tert-Butyl 2-hydroxy-2-((R)-4-(5-methyl-1-(pyridin-3-yl)-1H-pyrazol-3-yl)-3-oxomorpholin-2-yl)acetate (Compound 4-2)

According to Step 1-6 in the synthetic method for EXAMPLE 1, compound 4-1 (0.70 g) was used instead of compound 1-5 to obtain compound 4-2 as a colorless amorphous.

Step 4-3: (R)-tert-Butyl 2-acetoxy-2-((R)-4-(5-methyl-1-(pyridin-3-yl)-1H-pyrazol-3-yl)-3-oxomorpholin-2-yl)acetate (Compound 4-3)

According to Step 2-3 in the synthetic method for EXAMPLE 2, compound 4-2 (0.51 g) was used instead of compound 1-6 to obtain compound 4-3 as a colorless amorphous.

Step 4-4: (R)-2-Acetoxy-2-((R)-4-(5-methyl-1-(pyridin-3-yl)-1H-pyrazol-3-yl)-3-oxomorpholin-2-yl) acetic acid hydrochloride (Compound 4-4)

According to Step 1-7 in the synthetic method for EXAMPLE 1, compound 4-3 (0.51 g) was used instead of compound 1-6 to obtain compound 4-4 as a pale yellow solid.

Step 4-5: (R)-2-((7-Carbamoyl-3-(1,3-dioxoisoindolin-2-yl)benzo[d]isothiazol-6-yl)amino)-1-((R)-4-(5-methyl-1-(pyridin-3-yl)-1H-pyrazol-3-yl)-3-oxomorpholin-2-yl)-2-oxoethyl acetate (Compound 4-5)

According to Step 2-5 in the synthetic method for EXAMPLE 2, compound 4-4 (0.15 g) was used instead of compound 2-4 to obtain compound 4-5 as a yellow solid.

Step 4-6: (R)-2-((S)-(3-Amino-9-oxo-6,9-dihydroisothiazolo[5,4-f]quinazolin-7-yl)(hydroxy)methyl)-4-(5-methyl-1-(pyridin-3-yl)-1H-pyrazol-3-yl)morpholin-3-one According to Step 2-6 in the synthetic method for EXAMPLE 2, compound 4-5 (18 mg) was used instead of compound 2-5 to obtain EXAMPLE 4 as a pale yellow solid.

EXAMPLE 5

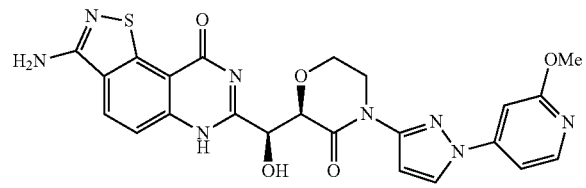 [SMILES: COc1cc(-n2ccc(N3CCO[C@H]([C@@H](O)c4nc(=O)c5c(ccc6c(N)nsc65)[nH]4)C3=O)n2)ccn1]

(R)-2-((S)-(3-Amino-9-oxo-6,9-dihydroisothiazolo[5,4-f]quinazolin-7-yl)(hydroxy)methyl)-4-(1-(2-methoxypyridin-4-yl)-1H-pyrazol-3-yl)morpholin-3-one Step 5-1: 4-(3-Iodo-1H-pyrazol-1-yl)-2-methoxypyridine (Compound 5-1)

According to Step 1-5 in the synthetic method for EXAMPLE 1, 4-bromo-2-methoxypyridine (2.3 g) was used instead of 4-fluoropyridine to obtain compound 5-1 as a colorless solid.

Step 5-2: (R)-tert-Butyl 2-hydroxy-2-((R)-4-(1-(2-methoxypyridin-4-yl)-1H-pyrazol-3-yl)-3-oxomorpholin-2-yl)acetate (compound 5-2)

According to Step 1-6 in the synthetic method for EXAMPLE 1, compound 5-1 (1.2 g) was used instead of compound 1-5 to obtain compound 5-2 as a colorless solid.

Step 5-3: (R)-tert-Butyl 2-acetoxy-2-((R)-4-(1-(2-methoxypyridin-4-yl)-1H-pyrazol-3-yl)-3-oxomorpholin-2-yl)acetate (Compound 5-3)

According to Step 2-3 in the synthetic method for EXAMPLE 2, compound 5-2 (0.53 g) was used instead of compound 1-6 to obtain compound 5-3 as a colorless solid.

Step 5-4: (R)-2-acetoxy-2-((R)-4-(1-(2-methoxypyridin-4-yl)-1H-pyrazol-3-yl)-3-oxomorpholin-2-yl)acetic acid hydrochloride (Compound 5-4)

According to Step 1-7 in the synthetic method for EXAMPLE 1, compound 5-3 (0.55 g) was used instead of compound 1-6 to obtain compound 5-4 as a colorless solid.

Step 5-5: (R)-2-((7-Carbamoyl-3-(1,3-dioxoisoindolin-2-yl)benzo[d]isothiazol-6-yl)amino)-1-((R)-4-(1-(2-methoxypyridin-4-yl)-1H-pyrazol-3-yl)-3-oxomorpholin-2-yl)-2-oxoethyl acetate (Compound 5-5)

According to Step 2-5 in the synthetic method for EXAMPLE 2, compound 5-4 (0.15 g) was used instead of compound 2-4 to obtain compound 5-5 as a pale yellow solid.

Step 5-6: (R)-2-((S)-(3-Amino-9-oxo-6,9-dihydroisothiazolo[5,4-f]quinazolin-7-yl)(hydroxy)methyl)-4-(1-(2-methoxypyridin-4-yl)-1H-pyrazol-3-yl)morpholin-3-one According to Step 2-6 in the synthetic method for EXAMPLE 2, compound 5-5 (56 mg) was used instead of compound 2-5 to obtain EXAMPLE 5 as a pale yellow solid.

EXAMPLE 6

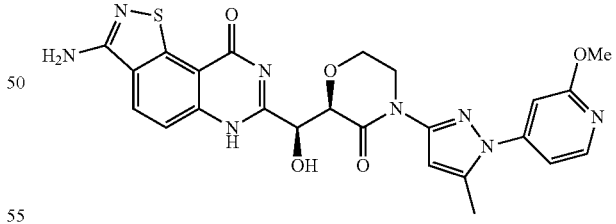

(R)-2-((S)-(3-Amino-9-oxo-6,9-dihydroisothiazolo[5,4-f]quinazolin-7-yl)(hydroxy)methyl)-4-(1-(2-methoxypyridin-4-yl)-5-methyl-1H-pyrazol-3-yl)morpholin-3-one Step 6-1: 4-(3-Iodo-5-methyl-1H-pyrazol-1-yl)-2-methoxypyridine (Compound 6-1)

According to Step 4-1 in the synthetic method for EXAMPLE 4, (2-methoxypyridin-4-yl)boronic acid (2.2 g)

was used instead of 3-pyridineboronic acid to obtain compound 6-1 as a colorless solid.

Step 6-2: (R)-tert-Butyl 2-hydroxy-2-((R)-4-(1-(2-methoxypyridin-4-yl)-5-methyl-1H-pyrazol-3-yl)-3-oxomorpholin-2-yl)acetate (Compound 6-2)

According to Step 1-6 in the synthetic method for EXAMPLE 1, compound 6-1 (0.40 g) was used instead of compound 1-5 to obtain compound 6-2 as a colorless solid.

Step 6-3: (R)-tert-Butyl 2-acetoxy-2-((R)-4-(1-(2-methoxypyridin-4-yl)-5-methyl-1H-pyrazol-3-yl)-3-oxomorpholin-2-yl)acetate (Compound 6-3)

According to Step 2-3 in the synthetic method for EXAMPLE 2, compound 6-2 (0.24 g) was used instead of compound 1-6 to obtain compound 6-3 as a colorless solid.

Step 6-4: (R)-2-Acetoxy-2-((R)-4-(1-(2-methoxypyridin-4-yl)-5-methyl-1H-pyrazol-3-yl)-3-oxomorpholin-2-yl)acetic acid hydrochloride (Compound 6-4)

According to Step 1-7 in the synthetic method for EXAMPLE 1, compound 6-3 (0.26 g) was used instead of compound 1-6 to obtain compound 6-4 as a colorless solid.

Step 6-5: (R)-2-((7-Carbamoyl-3-(1,3-dioxoisoindolin-2-yl)benzo[d]isothiazol-6-yl)amino)-1-((R)-4-(1-(2-methoxypyridin-4-yl)-5-methyl-1H-pyrazol-3-yl)-3-oxomorpholin-2-yl)-2-oxoethyl acetate (Compound 6-5)

According to Step 2-5 in the synthetic method for EXAMPLE 2, compound 6-4 (50 mg) was used instead of compound 2-4 to obtain compound 6-5 as a pale yellow solid.

Step 6-6: (R)-2-((S)-(3-Amino-9-oxo-6,9-dihydroisothiazolo[5,4-f]quinazolin-7-yl)(hydroxy)methyl)-4-(1-(2-methoxypyridin-4-yl)-5-methyl-1H-pyrazol-3-yl)morpholin-3-one According to Step 2-6 in the synthetic method for EXAMPLE 2, compound 6-5 (50 mg) was used instead of compound 2-5 to obtain EXAMPLE 6 as a pale yellow solid.

EXAMPLE 7

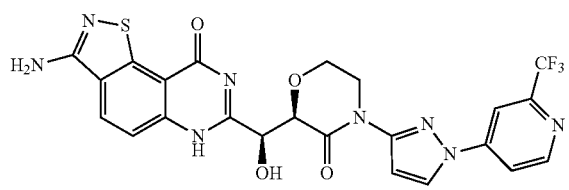 [SMILES: Nc1nsc2c1ccc1[nH]c([C@H](O)[C@H]3OCCN(c4ccn(-c5ccnc(C(F)(F)F)c5)n4)C3=O)nc(=O)c12]

(R)-2-((S)-(3-Amino-9-oxo-6,9-dihydroisothiazolo[5,4-f]quinazolin-7-yl)(hydroxy)methyl)-4-(1-(2-(trifluoromethyl)pyridin-4-yl)-1H-pyrazol-3-yl)morpholin-3-one Step 7-1: 4-(3-Iodo-1H-pyrazol-1-yl)-2-(trifluoromethyl)pyridine (Compound 7-1)

According to Step 1-5 in the synthetic method for EXAMPLE 1, 4-iodo-2-(trifluoromethyl)pyridine (2.1 g) was used instead of 4-fluoropyridine to obtain compound 7-1 as a colorless solid.

Step 7-2: (R)-tert-Butyl 2-hydroxy-2-((R)-3-oxo-4-(1-(2-(trifluoromethyl)pyridin-4-yl)-1H-pyrazol-3-yl)morpholin-2-yl)acetate (Compound 7-2)

According to Step 1-6 in the synthetic method for EXAMPLE 1, compound 7-1 (1.2 g) was used instead of compound 1-5 to obtain compound 7-2 as a colorless solid.

Step 7-3: (R)-tert-Butyl 2-acetoxy-2-((R)-3-oxo-4-(1-(2-(trifluoromethyl)pyridin-4-yl)-1H-pyrazol-3-yl)morpholin-2-yl)acetate (Compound 7-3)

According to Step 2-3 in the synthetic method for EXAMPLE 2, compound 7-2 (0.74 g) was used instead of compound 1-6 to obtain compound 7-3 as a colorless amorphous.

Step 7-4: (R)-2-Acetoxy-2-((R)-3-oxo-4-(1-(2-(trifluoromethyl)pyridin-4-yl)-1H-pyrazol-3-yl)morpholin-2-yl)acetic acid hydrochloride (Compound 7-4)

According to Step 1-7 in the synthetic method for EXAMPLE 1, compound 7-3 (0.78 g) was used instead of compound 1-6 to obtain compound 7-4 as a colorless solid.

Step 7-5: (R)-2-((7-Carbamoyl-3-(1,3-dioxoisoindolin-2-yl)benzo[d]isothiazol-6-yl)amino)-2-oxo-1-((R)-3-oxo-4-(1-(2-(trifluoromethyl)pyridin-4-yl)-1H-pyrazol-3-yl)morpholin-2-yl)ethyl acetate (Compound 7-5)

According to Step 2-5 in the synthetic method for EXAMPLE 2, compound 7-4 (0.20 g) was used instead of compound 2-4 to obtain compound 7-5 as a pale yellow solid.

Step 7-6: (R)-2-((S)-(3-Amino-9-oxo-6,9-dihydroisothiazolo[5,4-f]quinazolin-7-yl)(hydroxy)methyl)-4-(1-(2-(trifluoromethyl)pyridin-4-yl)-1H-pyrazol-3-yl)morpholin-3-one According to Step 2-6 in the synthetic method for EXAMPLE 2, compound 7-5 (64 mg) was used instead of compound 2-5 to obtain EXAMPLE 7 as a pale yellow solid.

EXAMPLE 8

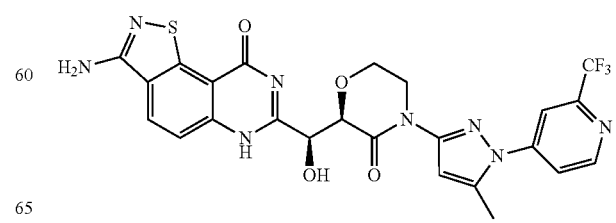

(R)-2-((S)-(3-Amino-9-oxo-6,9-dihydroisothiazolo[5,4-f]quinazolin-7-yl)(hydroxy)methyl)-4-(5-methyl-1-(2-(trifluoromethyl)pyridin-4-yl)-1H-pyrazol-3-yl)morpholin-3-one Step 8-1: 4-(3-Iodo-5-methyl-1H-pyrazol-1-yl)-2-(trifluoromethyl)pyridine (Compound 8-1)

According to Step 1-5 in the synthetic method for EXAMPLE 1, 4-iodo-2-(trifluoromethyl)pyridine (2.2 g) and 5-iodo-3-methylpyrazole (1.7 g) were used instead of 4-fluoropyridine and 3-iodopyrazole to obtain compound 8-1 as a colorless solid.

Step 8-2: (R)-tert-Butyl 2-hydroxy-2-((R)-4-(5-methyl-1-(2-(trifluoromethyl)pyridin-4-yl)-1H-pyrazol-3-yl)-3-oxomorpholin-2-yl)acetate (Compound 8-2)

According to Step 1-6 in the synthetic method for EXAMPLE 1, compound 8-1 (0.50 g) was used instead of compound 1-5 to obtain compound 8-2 as a colorless solid.

Step 8-3: (R)-tert-Butyl 2-acetoxy-2-((R)-4-(5-methyl-1-(2-(trifluoromethyl)pyridin-4-yl)-1H-pyrazol-3-yl)-3-oxomorpholin-2-yl)acetate (Compound 8-3)

According to Step 2-3 in the synthetic method for EXAMPLE 2, compound 8-2 (0.41 g) was used instead of compound 1-6 to obtain compound 8-3 as a colorless solid.

Step 8-4: (R)-2-Acetoxy-2-((R)-4-(5-methyl-1-(2-(trifluoromethyl)pyridin-4-yl)-1H-pyrazol-3-yl)-3-oxomorpholin-2-yl)acetic acid hydrochloride (Compound 8-4)

According to Step 1-7 in the synthetic method for EXAMPLE 1, compound 8-3 (0.41 g) was used instead of compound 1-6 to obtain compound 8-4 as a colorless solid.

Step 8-5: (R)-2-((7-Carbamoyl-3-(1,3-dioxoisoindolin-2-yl)benzo[d]isothiazol-6-yl)amino)-1-((R)-4-(5-methyl-1-(2-(trifluoromethyl)pyridin-4-yl)-1H-pyrazol-3-yl)-3-oxomorpholin-2-yl)-2-oxoethyl acetate (Compound 8-5)

According to Step 2-5 in the synthetic method for EXAMPLE 2, compound 8-4 (0.15 g) was used instead of compound 2-4 to obtain compound 8-5 as a pale yellow solid.

Step 8-6: (R)-2-((S)-(3-Amino-9-oxo-6,9-dihydroisothiazolo[5,4-f]quinazolin-7-yl)(hydroxy)methyl)-4-(5-methyl-1-(2-(trifluoromethyl)pyridin-4-yl)-1H-pyrazol-3-yl)morpholin-3-one According to Step 2-6 in the synthetic method for EXAMPLE 2, compound 8-5 (90 mg) was used instead of compound 2-5 to obtain EXAMPLE 8 as a pale yellow solid.

EXAMPLE 9

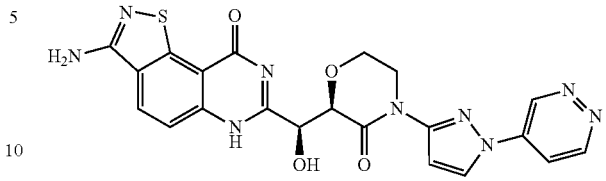

(R)-2-((S)-(3-Amino-9-oxo-6,9-dihydroisothiazolo[5,4-f]quinazolin-7-yl)(hydroxy)methyl)-4-(1-(pyridazin-4-yl)-1H-pyrazol-3-yl)morpholin-3-one Step 9-1: 4-(3-Iodo-1H-pyrazol-1-yl)pyridazine (Compound 9-1)

According to Step 1-5 in the synthetic method for EXAMPLE 1, 4-Bromopyridazine hydrobromide (1.4 g) was used instead of 4-fluoropyridine to obtain compound 9-1 as a brown solid.

Step 9-2: (R)-tert-Butyl 2-hydroxy-2-((R)-3-oxo-4-(1-(pyridazin-4-yl)-1H-pyrazol-3-yl)morpholin-2-yl)acetate (Compound 9-2)

According to Step 1-6 in the synthetic method for EXAMPLE 1, compound 9-1 (1.2 g) was used instead of compound 1-5 to obtain compound 9-2 as a yellow solid.

Step 9-3: (R)-tert-Butyl 2-acetoxy-2-((R)-3-oxo-4-(1-(pyridazin-4-yl)-1H-pyrazol-3-yl)morpholin-2-yl)acetate (compound 9-3)

According to Step 2-3 in the synthetic method for EXAMPLE 2, compound 9-2 (0.36 g) was used instead of compound 1-6 to obtain compound 9-3 as a yellow solid.

Step 9-4: (R)-2-Acetoxy-2-((R)-3-oxo-4-(1-(pyridazin-4-yl)-1H-pyrazol-3-yl)morpholin-2-yl)acetic acid hydrochloride (Compound 9-4)

According to Step 1-7 in the synthetic method for EXAMPLE 1, compound 9-3 (0.34 g) was used instead of compound 1-6 to obtain compound 9-4 as a yellow solid.

Step 9-5: (1R)-2-((7-Carbamoyl-3-(1,3-dioxoisoindolin-2-yl)benzo[d]isothiazol-6-yl)amino)-2-oxo-1-(3-oxo-4-(1-(pyridazin-4-yl)-1H-pyrazol-3-yl)morpholin-2-yl)ethyl acetate (Compound 9-5)

According to Step 2-5 in the synthetic method for EXAMPLE 2, compound 9-4 (0.18 g) was used instead of compound 2-4 to obtain compound 9-5 as a yellow solid.

Step 9-6: (R)-2-((S)-(3-Amino-9-oxo-6,9-dihydroisothiazolo[5,4-f]quinazolin-7-yl)(hydroxy)methyl)-4-(1-(pyridazin-4-yl)-1H-pyrazol-3-yl)morpholin-3-one To a solution of 9-5 (46 mg) in $CH_2Cl_2$ (1 mL) and MeOH (1 mL), hydrazine hydrate (65.6 uL) was added and stirred at room temperature for 6 h. The reaction mixture was diluted with water and the precipitated solid was filtered and dried. The solid (28 mg) was suspended in acetonitrile (3 mL) and DMF (3 mL), and K$_2$CO$_3$ (37 mg) was added. The mixture was stirred at 40° C. for 2 days. The reaction mixture was cooled to room temperature and poured into sat.NH$_4$Cl, and diluted with EtOAc. The precipitated solid was filtered, and triturated with MeOH to obtain EXAMPLE 9 as a pale yellow solid.

EXAMPLE 10

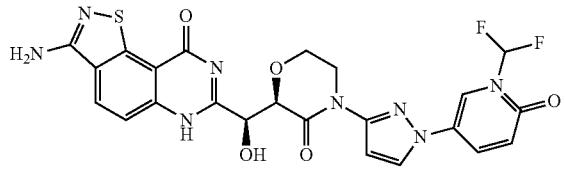

(R)-2-((S)-(3-Amino-9-oxo-6,9-dihydroisothiazolo[5,4-f]quinazolin-7-yl)(hydroxy)methyl)-4-(1-(1-(difluoromethyl)-6-oxo-1,6-dihydropyridin-3-yl)-1H-pyrazol-3-yl)morpholin-3-one Step 10-1: 5-(3-Amino-1H-pyrazol-1-yl)-1-(difluoromethyl)pyridin-2(1H)-one (Compound 10-1)

According to Step 1-6 in the synthetic method for EXAMPLE 1,5-bromo-1-difluoromethyl-1H-pyridin-2-one (5.2 g) and 3-aminopyrazole (1.9 g) were used instead of compound 1-5 and (R)-tert-butyl 2-hydroxy-2-((R)-3-oxomorpholin-2-yl)acetate to obtain compound 10-1 as a yellow solid.

Step 10-2: 1-(Difluoromethyl)-5-(3-iodo-1H-pyrazol-1-yl)pyridin-2(1H)-one (Compound 10-2)

To a solution of compound 10-1 (1.15 g) in MeCN (30 mL) was added concentrated H$_2$SO$_4$ (0.68 mL) and NaNO$_2$ (0.70 g) in water (3 mL) at 0° C. After stirring for 10 min at 0° C., KI (3.38 g) in water (4 mL) was added to the reaction at the same temperature. The reaction mixture was stirred for 1 h at room temperature and for 20 min at 40° C. It was diluted with water and extracted with EtOAc. The organic layer was washed with sat. Na$_2$S$_2$O$_3$ aq., sat. NaHCO$_3$ aq. and brine, dried over Na$_2$SO$_4$, filtered and concentrated. The residue was purified by silica gel flash chromatography (eluent:Hexane:EtOAc=90:10~50:50) to give compound 10-2 as a colorless solid.

Step 10-3: (R)-tert-Butyl 2-((R)-4-(1-(1-(difluoromethyl)-6-oxo-1,6-dihydropyridin-3-yl)-1H-pyrazol-3-yl)-3-oxomorpholin-2-yl)-2-hydroxyacetate (Compound 10-3)

According to Step 1-6 in the synthetic method for EXAMPLE 1, compound 10-2 (0.59 g) was used instead of compound 1-5 to obtain compound 10-3 as a pale yellow solid.

Step 10-4: (R)-tert-Butyl 2-acetoxy-2-((R)-4-(1-(1-(difluoromethyl)-6-oxo-1,6-dihydropyridin-3-yl)-1H-pyrazol-3-yl)-3-oxomorpholin-2-yl)acetate (Compound 10-4)

According to Step 2-3 in the synthetic method for EXAMPLE 2, compound 10-3 (0.57 g) was used instead of compound 1-6 to obtain compound 10-4 as a colorless amorphous.

Step 10-5: (R)-2-Acetoxy-2-((R)-4-(1-(1-(difluoromethyl)-6-oxo-1,6-dihydropyridin-3-yl)-1H-pyrazol-3-yl)-3-oxomorpholin-2-yl)acetic acid (Compound 10-5)

According to Step 1-7 in the synthetic method for EXAMPLE 1, compound 10-4 (0.48 g) was used instead of compound 1-6 to obtain compound 10-5.

Step 10-6: (R)-2-((7-Carbamoyl-3-(1,3-dioxoisoindolin-2-yl)benzo[d]isothiazol-6-yl)amino)-1-((R)-4-(1-(1-(difluoromethyl)-6-oxo-1,6-dihydropyridin-3-yl)-1H-pyrazol-3-yl)-3-oxomorpholin-2-yl)-2-oxoethyl acetate (Compound 10-6)

According to Step 2-5 in the synthetic method for EXAMPLE 2, compound 10-5 (0.24 g) was used instead of compound 2-4 to obtain compound 10-6 as a pale yellow solid.

Step 10-7: (R)-2-((S)-(3-Amino-9-oxo-6,9-dihydroisothiazolo[5,4-f]quinazolin-7-yl)(hydroxy)methyl)-4-(1-(1-(difluoromethyl)-6-oxo-1,6-dihydropyridin-3-yl)-1H-pyrazol-3-yl)morpholin-3-one According to Step 9-6 in the synthetic method for EXAMPLE 9, compound 10-6 (92 mg) was used instead of compound 9-5 to obtain EXAMPLE 10 as a colorless solid.

EXAMPLE 11

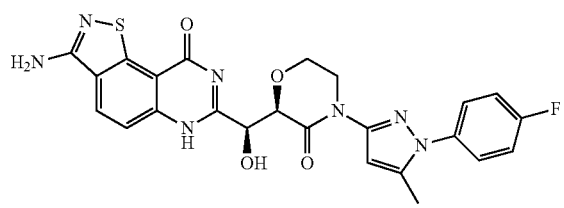 [SMILES: Cc1cc(N2CCO[C@H]([C@@H](O)c3nc(=O)c4c(ccc5c(N)nsc54)[nH]3)C2=O)nn1-c1ccc(F)cc1]

(R)-2-((S)-(3-Amino-9-oxo-6,9-dihydroisothiazolo[5,4-f]quinazolin-7-yl)(hydroxy)methyl)-4-(1-(4-fluorophenyl)-5-methyl-1H-pyrazol-3-yl)morpholin-3-one Step 11-1: 1-(4-Fluorophenyl)-3-iodo-5-methyl-1H-pyrazole (Compound 11-1)

According to Step 4-1 in the synthetic method for EXAMPLE 4, 4-fluorobenzeneboronic acid (3.2 g) was used instead of 3-pyridineboronic acid to obtain compound 11-1 as a yellow oil.

Step 11-2: (R)-tert-Butyl 2-((R)-4-(1-(4-fluorophenyl)-5-methyl-1H-pyrazol-3-yl)-3-oxomorpholin-2-yl)-2-hydroxyacetate (Compound 11-2)

According to Step 1-6 in the synthetic method for EXAMPLE 1, compound 11-1 (0.48 g) was used instead of compound 1-5 to obtain compound 11-2 as a colorless solid.

Step 11-3: (R)-tert-Butyl 2-acetoxy-2-((R)-4-(1-(4-fluorophenyl)-5-methyl-1H-pyrazol-3-yl)-3-oxomorpholin-2-yl)acetate (compound 11-3)

According to Step 2-3 in the synthetic method for EXAMPLE 2, compound 11-2 (0.21 g) was used instead of compound 1-6 to obtain compound 11-3 as a colorless solid.

Step 11-4: (R)-2-Acetoxy-2-((R)-4-(1-(4-fluorophenyl)-5-methyl-1H-pyrazol-3-yl)-3-oxomorpholin-2-yl)acetic acid (Compound 11-4)

According to Step 1-7 in the synthetic method for EXAMPLE 1, compound 11-3 (0.22 g) was used instead of compound 1-6 to obtain compound 11-4 as a colorless solid.

Step 11-5: (R)-2-((7-Carbamoyl-3-(1,3-dioxoisoindolin-2-yl)benzo[d]isothiazol-6-yl)amino)-1-((R)-4-(1-(4-fluorophenyl)-5-methyl-1H-pyrazol-3-yl)-3-oxomorpholin-2-yl)-2-oxoethyl acetate (Compound 11-5)

According to Step 2-5 in the synthetic method for EXAMPLE 2, compound 11-4 (0.10 g) was used instead of compound 2-4 to obtain compound 11-5 as a pale yellow solid.

Step 11-6: (R)-2-((S)-(3-Amino-9-oxo-6,9-dihydroisothiazolo[5,4-f]quinazolin-7-yl)(hydroxy)methyl)-4-(1-(4-fluorophenyl)-5-methyl-1H-pyrazol-3-yl)morpholin-3-one According to Step 2-6 in the synthetic method for EXAMPLE 2, compound 11-5 (24 mg) was used instead of compound 2-5 to obtain EXAMPLE 11 as a red solid.

EXAMPLE 12

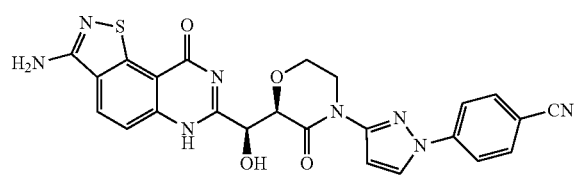 [SMILES: N#Cc1ccc(-n2ccc(N3CCO[C@H]([C@@H](O)c4nc(=O)c5c(ccc6c(N)nsc65)[nH]4)C3=O)n2)cc1]

4-(3-((R)-2-((S)-(3-Amino-9-oxo-6,9-dihydroisothiazolo[5,4-f]quinazolin-7-yl)(hydroxy)methyl)-3-oxomorpholino)-1H-pyrazol-1-yl)benzonitrile Step 12-1: 4-(3-iodo-1H-pyrazol-1-yl)benzonitrile (Compound 12-1)

According to Step 1-5 in the synthetic method for EXAMPLE 1, 4-fluorobenzonitrile (0.19 g) was used instead of 4-fluoropyridine to obtain compound 12-1 as a colorless solid.

Step 12-2: (R)-tert-Butyl 2-((R)-4-(1-(4-cyanophenyl)-1H-pyrazol-3-yl)-3-oxomorpholin-2-yl)-2-hydroxyacetate (Compound 12-2)

According to Step 1-6 in the synthetic method for EXAMPLE 1, compound 12-1 (0.55 g) was used instead of compound 1-5 to obtain compound 12-2 as a colorless solid.

Step 12-3: (R)-tert-Butyl 2-acetoxy-2-((R)-4-(1-(4-cyanophenyl)-1H-pyrazol-3-yl)-3-oxomorpholin-2-yl)acetate (Compound 12-3)

According to Step 2-3 in the synthetic method for EXAMPLE 2, compound 12-2 (0.14 g) was used instead of compound 1-6 to obtain compound 12-3.

Step 12-4: (R)-2-Acetoxy-2-((R)-4-(1-(4-cyanophenyl)-1H-pyrazol-3-yl)-3-oxomorpholin-2-yl)acetic acid (Compound 12-4)

According to Step 1-7 in the synthetic method for EXAMPLE 1, compound 12-3 (0.15 g) was used instead of compound 1-6 to obtain compound 12-4.

Step 12-5: (R)-2-((7-Carbamoyl-3-(1,3-dioxoisoindolin-2-yl)benzo[d]isothiazol-6-yl)amino)-1-((R)-4-(1-(4-cyanophenyl)-1H-pyrazol-3-yl)-3-oxomorpholin-2-yl)-2-oxoethyl acetate (Compound 12-5)

According to Step 2-5 in the synthetic method for EXAMPLE 2, compound 12-4 (0.12 g) was used instead of compound 2-4 to obtain compound 12-5 as a yellow solid.

Step 12-6: 4-(3-((R)-2-((S)-(3-Amino-9-oxo-6,9-dihydroisothiazolo[5,4-f]quinazolin-7-yl)(hydroxy)methyl)-3-oxomorpholino)-1H-pyrazol-1-yl)benzonitrile According to Step 9-6 in the synthetic method for EXAMPLE 9, compound 12-5 (28 mg) was used instead of compound 9-5 to obtain EXAMPLE 12 as a pale yellow solid.

EXAMPLE 13

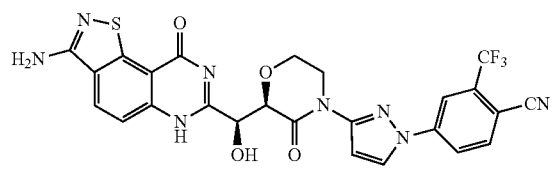 [SMILES: N#Cc1ccc(-n2ccc(N3CCO[C@H]([C@@H](O)c4nc(=O)c5c(ccc6c(N)nsc65)[nH]4)C3=O)n2)cc1C(F)(F)F]

4-(3-((R)-2-((S)-(3-Amino-9-oxo-6,9-dihydroisothiazolo[5,4-f]quinazolin-7-yl)(hydroxy)methyl)-3-oxomorpholino)-1H-pyrazol-1-yl)-2-(trifluoromethyl)benzonitrile Step 13-1: 4-(3-iodo-1H-pyrazol-1-yl)-2-(trifluoromethyl)benzonitrile (Compound 13-1)

According to Step 1-5 in the synthetic method for EXAMPLE 1, 4-fluoro-2-(trifluoromethyl)benzonitrile (2.4 g) was used instead of 4-fluoropyridine to obtain compound 13-1 as a pale yellow solid.

Step 13-2: (R)-tert-Butyl 2-((R)-4-(1-(4-cyano-3-(trifluoromethyl)phenyl)-1H-pyrazol-3-yl)-3-oxomorpholin-2-yl)-2-hydroxyacetate (Compound 13-2)

According to Step 1-6 in the synthetic method for EXAMPLE 1, compound 13-1 (2.0 g) was used instead of compound 1-5 to obtain compound 13-2 as a yellow solid.

Step 13-3: (R)-tert-Butyl 2-acetoxy-2-((R)-4-(1-(4-cyano-3-(trifluoromethyl)phenyl)-1H-pyrazol-3-yl)-3-oxomorpholin-2-yl)acetate (Compound 13-3)

According to Step 2-3 in the synthetic method for EXAMPLE 2, compound 13-2 (0.50 g) was used instead of compound 1-6 to obtain compound 13-3.

Step 13-4: (R)-2-Acetoxy-2-((R)-4-(1-(4-cyano-3-(trifluoromethyl)phenyl)-1H-pyrazol-3-yl)-3-oxomorpholin-2-yl)acetic acid (Compound 13-4)

According to Step 1-7 in the synthetic method for EXAMPLE 1, compound 13-3 (0.55 g) was used instead of compound 1-6 to obtain compound 13-4.

Step 13-5: (R)-2-((7-carbamoyl-3-(1,3-dioxoisoindolin-2-yl)benzo[d]isothiazol-6-yl)amino)-1-((R)-4-(1-(4-cyano-3-(trifluoromethyl)phenyl)-1H-pyrazol-3-yl)-3-oxomorpholin-2-yl)-2-oxoethyl acetate (Compound 13-5)

According to Step 2-5 in the synthetic method for EXAMPLE 2, compound 13-4 (0.15 g) was used instead of compound 2-4 to obtain compound 13-5 as a solid.

Step 13-6: 4-(3-((R)-2-((S)-(3-Amino-9-oxo-6,9-dihydroisothiazolo[5,4-f]quinazolin-7-yl)(hydroxy)methyl)-3-oxomorpholino)-1H-pyrazol-1-yl)-2-(trifluoromethyl)benzonitrile According to Step 2-6 in the synthetic method for EXAMPLE 2, compound 13-5 (56 mg) was used instead of compound 2-5 to obtain EXAMPLE 13 as a pale yellow solid.

EXAMPLE 14

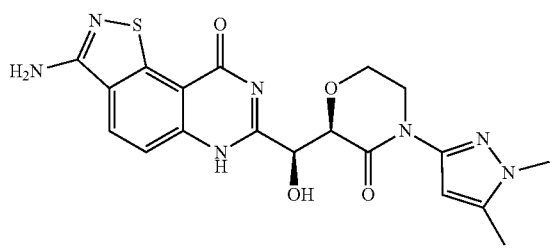 [SMILES: Cc1cc(N2CCO[C@H]([C@@H](O)c3nc(=O)c4c(ccc5c(N)nsc54)[nH]3)C2=O)nn1C]

(R)-2-((S)-(3-Amino-9-oxo-6,9-dihydroisothiazolo[5,4-f]quinazolin-7-yl)(hydroxy)methyl)-4-(1,5-dimethyl-1H-pyrazol-3-yl)morpholin-3-one Step 14-1: 3-Iodo-1,5-dimethyl-1H-pyrazole (Compound 14-1)

A solution of 3-methylpyrazole (5.0 g) in DMF (96 mL) was added 60% NaH (1.2 g), and it was stirred for 10 min at 0° C. Then the reaction mixture was added MeI (3.0 mL) at 0° C. and stirred for 1 h at room temperature. Then the reaction was quenched by the addition of H₂O, and the mixture was extracted with Et₂O. The combined organic extracts were dried over Na₂SO₄ and concentrated in vacuo. The crude mixture was purified by column chromatography on SiO₂ (hexane/EtOAc=100/0→80/20) to give compound 14-1 as yellow oil.

Step 14-2: (R)-tert-Butyl 2-((R)-4-(1,5-dimethyl-1H-pyrazol-3-yl)-3-oxomorpholin-2-yl)-2-hydroxyacetate (Compound 14-2)

According to Step 1-6 in the synthetic method for EXAMPLE 1, compound 14-1 (1.9 g) was used instead of compound 1-5 to obtain compound 14-2 as a colorless amorphous.

Step 14-3: (R)-tert-Butyl 2-acetoxy-2-((R)-4-(1,5-dimethyl-1H-pyrazol-3-yl)-3-oxomorpholin-2-yl)acetate (Compound 14-3)

According to Step 2-3 in the synthetic method for EXAMPLE 2, compound 14-2 (2.7 g) was used instead of compound 1-6 to obtain compound 14-3 as a colorless solid.

Step 14-4: (R)-2-Acetoxy-2-((R)-4-(1,5-dimethyl-1H-pyrazol-3-yl)-3-oxomorpholin-2-yl)acetic acid (Compound 14-4)

According to Step 1-7 in the synthetic method for EXAMPLE 1, compound 14-3 (2.7 g) was used instead of compound 1-6 to obtain compound 14-4 as a colorless solid.

Step 14-5: (R)-2-((7-carbamoyl-3-(1,3-dioxoisoindolin-2-yl)benzo[d]isothiazol-6-yl)amino)-1-((R)-4-(1,5-dimethyl-1H-pyrazol-3-yl)-3-oxomorpholin-2-yl)-2-oxoethyl acetate (Compound 14-5)

According to Step 2-5 in the synthetic method for EXAMPLE 2, compound 14-4 (0.50 g) was used instead of compound 2-4 to obtain compound 14-5 as a solid.

Step 14-6: (R)-2-((S)-(3-Amino-9-oxo-6,9-dihydroisothiazolo[5,4-f]quinazolin-7-yl)(hydroxy)methyl)-4-(1,5-dimethyl-1H-pyrazol-3-yl)morpholin-3-one According to Step 2-6 in the synthetic method for EXAMPLE 2, compound 14-5 (0.25 g) was used instead of compound 2-5 to obtain EXAMPLE 14 as a pale yellow solid.

EXAMPLE 15

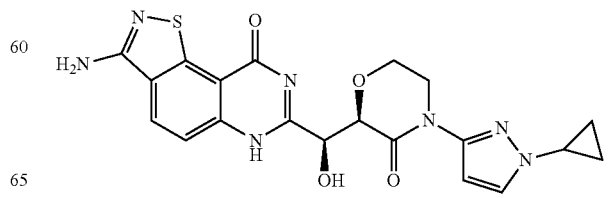

(R)-2-((S)-(3-Amino-9-oxo-6,9-dihydroisothiazolo[5,4-f]quinazolin-7-yl)(hydroxy)methyl)-4-(1-cyclopropyl-1H-pyrazol-3-yl)morpholin-3-one Step 15-1: 1-Cyclopropyl-3-iodo-1H-pyrazole (Compound 15-1)

According to Step 4-1 in the synthetic method for EXAMPLE 4, cyclopropylboronic acid (2.2 g) and 3-iodopyrazole (2.5 g) were used instead of 3-pyridineboronic acid and 5-iodo-3-methylpyrazole to obtain compound 15-1 as a pale yellow oil.

Step 15-2: (R)-tert-Butyl 2-((R)-4-(1-cyclopropyl-1H-pyrazol-3-yl)-3-oxomorpholin-2-yl)-2-hydroxyacetate (Compound 15-2)

According to Step 1-6 in the synthetic method for EXAMPLE 1, compound 15-1 (1.2 g) was used instead of compound 1-5 to obtain compound 15-2 as a colorless solid.

Step 15-3: (R)-tert-Butyl 2-acetoxy-2-((R)-4-(1-cyclopropyl-1H-pyrazol-3-yl)-3-oxomorpholin-2-yl)acetate (Compound 15-3)

According to Step 2-3 in the synthetic method for EXAMPLE 2, compound 15-2 (0.91 g) was used instead of compound 1-6 to obtain compound 15-3 as a colorless oil.

Step 15-4: (R)-2-Acetoxy-2-((R)-4-(1-cyclopropyl-1H-pyrazol-3-yl)-3-oxomorpholin-2-yl)acetic acid (Compound 15-4)

According to Step 1-7 in the synthetic method for EXAMPLE 1, compound 15-3 (0.95 g) was used instead of compound 1-6 to obtain compound 15-4.

Step 15-5: (R)-2-((7-Carbamoyl-3-(1,3-dioxoisoindolin-2-yl)benzo[d]isothiazol-6-yl)amino)-1-((R)-4-(1-cyclopropyl-1H-pyrazol-3-yl)-3-oxomorpholin-2-yl)-2-oxoethyl acetate (Compound 15-5)

According to Step 2-5 in the synthetic method for EXAMPLE 2, compound 15-4 (0.15 g) was used instead of compound 2-4 to obtain compound 15-5 as a yellow solid.

Step 15-6: (R)-2-((S)-(3-Amino-9-oxo-6,9-dihydroisothiazolo[5,4-f]quinazolin-7-yl)(hydroxy)methyl)-4-(1-cyclopropyl-1H-pyrazol-3-yl)morpholin-3-one According to Step 2-6 in the synthetic method for EXAMPLE 2, compound 15-5 (47 mg) was used instead of compound 2-5 to obtain EXAMPLE 15 as a pale yellow solid.

EXAMPLE 16

(R)-2-((S)-(3-Amino-9-oxo-6,9-dihydroisothiazolo[5,4-f]quinazolin-7-yl)(hydroxy)methyl)-4-(5-methyl-1-(tetrahydro-2H-pyran-4-yl)-1H-pyrazol-3-yl)morpholin-3-one Step 16-1: 3-Iodo-5-methyl-1-(tetrahydro-2H-pyran-4-yl)-1H-pyrazole (Compound 16-1)

According to Step 14-1 in the synthetic method for EXAMPLE 14, tetrahydro-2H-pyran-4-yl methanesulfonate (5.6 g) was used instead of iodomethane to obtain compound 16-1 as a colorless solid.

Step 16-2: (R)-tert-Butyl 2-hydroxy-2-((R)-4-(5-methyl-1-(tetrahydro-2H-pyran-4-yl)-1H-pyrazol-3-yl)-3-oxomorpholin-2-yl)acetate (Compound 16-2)

According to Step 1-6 in the synthetic method for EXAMPLE 1, compound 16-1 (1.8 g) was used instead of compound 1-5 to obtain compound 16-2 as a colorless solid.

Step 16-3: (R)-tert-Butyl 2-acetoxy-2-((R)-4-(5-methyl-1-(tetrahydro-2H-pyran-4-yl)-1H-pyrazol-3-yl)-3-oxomorpholin-2-yl)acetate (Compound 16-3)

According to Step 2-3 in the synthetic method for EXAMPLE 2, compound 16-2 (1.1 g) was used instead of compound 1-6 to obtain compound 16-3 as a colorless solid.

Step 16-4: (R)-2-Acetoxy-2-((R)-4-(5-methyl-1-(tetrahydro-2H-pyran-4-yl)-1H-pyrazol-3-yl)-3-oxomorpholin-2-yl)acetic acid (compound 16-4)

According to Step 1-7 in the synthetic method for EXAMPLE 1, compound 16-3 (1.2 g) was used instead of compound 1-6 to obtain compound 16-4 as a pale green amorphous.

Step 16-5: (R)-2-((7-Carbamoyl-3-(1,3-dioxoisoindolin-2-yl)benzo[d]isothiazol-6-yl)amino)-1-((R)-4-(5-methyl-1-(tetrahydro-2H-pyran-4-yl)-1H-pyrazol-3-yl)-3-oxomorpholin-2-yl)-2-oxoethyl acetate (Compound 16-5)

According to Step 2-5 in the synthetic method for EXAMPLE 2, compound 16-4 (0.16 g) was used instead of compound 2-4 to obtain compound 16-5 as a solid.

Step 16-6: (R)-2-((S)-(3-Amino-9-oxo-6,9-dihydroisothiazolo[5,4-f]quinazolin-7-yl)(hydroxy)methyl)-4-(5-methyl-1-(tetrahydro-2H-pyran-4-yl)-1H-pyrazol-3-yl)morpholin-3-one According to Step 2-6 in the synthetic method for EXAMPLE 2, compound 16-5 (0.14 g) was used instead of compound 2-5 to obtain EXAMPLE 16 as a pale yellow solid.

EXAMPLE 17

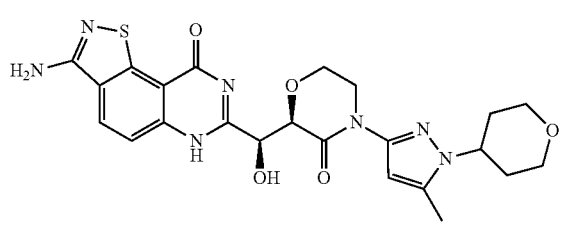 [SMILES: Cc1cc(N2CCO[C@H]([C@@H](O)c3nc(=O)c4c(ccc5c(N)nsc54)[nH]3)C2=O)nn1C1CCOCC1]

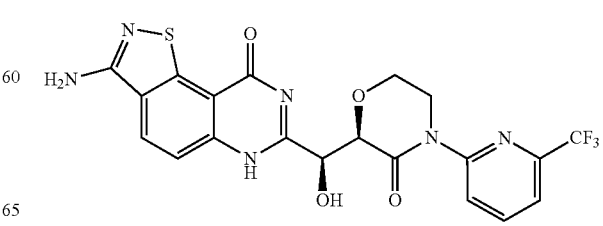

(R)-2-((S)-(3-Amino-9-oxo-6,9-dihydroisothiazolo[5,4-f]quinazolin-7-yl)(hydroxy)methyl)-4-(6-(trifluoromethyl)pyridin-2-yl)morpholin-3-one Step 17-1: (R)-tert-Butyl 2-hydroxy-2-((R)-3-oxo-4-(6-(trifluoromethyl)pyridin-2-yl)morpholin-2-yl)acetate (Compound 17-1)

According to Step 1-6 in the synthetic method for EXAMPLE 1,2-iodo-6-trifluoromethylpyridine (2.5 g) was used instead of compound 1-5 to obtain compound 17-1 as a colorless solid.

Step 17-2: (R)-tert-Butyl 2-acetoxy-2-((R)-3-oxo-4-(6-(trifluoromethyl)pyridin-2-yl)morpholin-2-yl)acetate (Compound 17-2)

According to Step 2-3 in the synthetic method for EXAMPLE 2, compound 17-1 (0.50 g) was used instead of compound 1-6 to obtain compound 17-2 as colorless oil.

Step 17-3: (R)-2-Acetoxy-2-((R)-3-oxo-4-(6-(trifluoromethyl)pyridin-2-yl)morpholin-2-yl)acetic acid (Compound 17-3)

According to Step 1-7 in the synthetic method for EXAMPLE 1, compound 17-2 (0.57 g) was used instead of compound 1-6 to obtain compound 17-3.

Step 17-4: (R)-2-((7-Carbamoyl-3-(1,3-dioxoisoindolin-2-yl)benzo[d]isothiazol-6-yl)amino)-2-oxo-1-((R)-3-oxo-4-(6-(trifluoromethyl)pyridin-2-yl)morpholin-2-yl)ethyl acetate (Compound 17-4)

According to Step 2-5 in the synthetic method for EXAMPLE 2, compound 17-3 (0.20 g) was used instead of compound 2-4 to obtain compound 17-4 as a solid.

Step 17-5: (R)-2-((S)-(3-Amino-9-oxo-6,9-dihydroisothiazolo[5,4-f]quinazolin-7-yl)(hydroxy)methyl)-4-(6-(trifluoromethyl)pyridin-2-yl)morpholin-3-one To a solution of 17-4 (77 mg) in $CH_2Cl_2$ (1 mL) and MeOH (1 mL), hydrazine hydrate (0.11 mL) was added and stirred at room temperature for 3.5 h. The reaction mixture was diluted with water and the precipitated solid was filtered and dried. The solid (33 mg) was suspended in acetonitrile (10 mL) and $K_2CO_3$ (44.7 mg) was added. The mixture was stirred at 40° C. for 23 h. The reaction mixture was cooled to room temperature and poured into sat.$NH_4Cl$, and extracted with EtOAc. The combined organic layer was washed with brine and dried over $Na_2SO_4$. It was filtered to remove insoluble matters and concentrated in vacuo. The residue was purified by N—H silica gel flash chromatography (eluent:$CH_2Cl_2$:MeOH=95:5~90:10) to obtain EXAMPLE 17 as a pale yellow solid.

EXAMPLE 18

(R)-2-((S)-(3-Amino-9-oxo-6,9-dihydroisothiazolo[5,4-f]quinazolin-7-yl)(hydroxy)methyl)-4-(3-fluoro-6-(trifluoromethyl)pyridin-2-yl)morpholin-3-one Step 18-1: (R)-tert-Butyl 2-((R)-4-(3-fluoro-6-(trifluoromethyl)pyridin-2-yl)-3-oxomorpholin-2-yl)-2-hydroxyacetate (Compound 18-1)

According to Step 1-6 in the synthetic method for EXAMPLE 1,2-bromo-3-fluoro-6-trifluoromethylpyridine (0.42 g) was used instead of compound 1-5 to obtain compound 18-1 as a colorless solid.

Step 18-2: (R)-tert-Butyl 2-acetoxy-2-((R)-4-(3-fluoro-6-(trifluoromethyl)pyridin-2-yl)-3-oxomorpholin-2-yl)acetate (Compound 18-2)

According to Step 2-3 in the synthetic method for EXAMPLE 2, compound 18-1 (0.12 g) was used instead of compound 1-6 to obtain compound 18-2 as a solid.

Step 18-3: (R)-2-Acetoxy-2-((R)-4-(3-fluoro-6-(trifluoromethyl)pyridin-2-yl)-3-oxomorpholin-2-yl)acetic acid (Compound 18-3)

According to Step 1-7 in the synthetic method for EXAMPLE 1, compound 18-2 (0.13 g) was used instead of compound 1-6 to obtain compound 18-3 as a solid.

Step 18-4: (R)-2-((7-Carbamoyl-3-(1,3-dioxoisoindolin-2-yl)benzo[d]isothiazol-6-yl)amino)-1-((R)-4-(3-fluoro-6-(trifluoromethyl)pyridin-2-yl)-3-oxomorpholin-2-yl)-2-oxoethyl acetate (Compound 18-4)

According to Step 2-5 in the synthetic method for EXAMPLE 2, compound 18-3 (0.11 g) was used instead of compound 2-4 to obtain compound 18-4 as a yellow solid.

Step 18-5: (R)-2-((S)-(3-Amino-9-oxo-6,9-dihydroisothiazolo[5,4-f]quinazolin-7-yl)(hydroxy)methyl)-4-(3-fluoro-6-(trifluoromethyl)pyridin-2-yl)morpholin-3-one According to Step 9-6 in the synthetic method for EXAMPLE 9, compound 18-4 (42 mg) was used instead of compound 9-5 to obtain EXAMPLE 18 as a yellow solid.

EXAMPLE 19

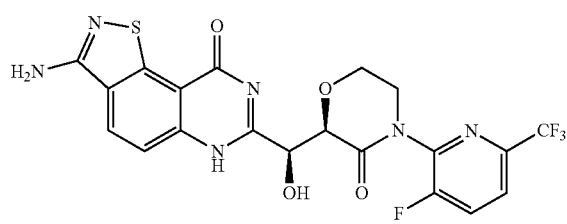 [SMILES: Nc1nsc2c1ccc1[nH]c([C@H](O)[C@H]3OCCN(c4nc(C(F)(F)F)ccc4F)C3=O)nc(=O)c12]

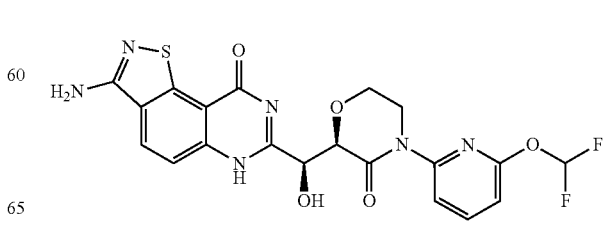

(R)-2-((S)-(3-Amino-9-oxo-6,9-dihydroisothiazolo[5,4-f]quinazolin-7-yl)(hydroxy)methyl)-4-(6-(difluoromethoxy)pyridin-2-yl)morpholin-3-one Step 19-1: (R)-tert-Butyl 2-((R)-4-(6-(difluoromethoxy)pyridin-2-yl)-3-oxomorpholin-2-yl)-2-hydroxyacetate (Compound 19-1)

According to Step 1-6 in the synthetic method for EXAMPLE 1, 2-bromo-6-(difluoromethoxy)pyridine (0.81 g) was used instead of compound 1-5 to obtain compound 19-1 as a colorless solid.

Step 19-2: (R)-tert-Butyl 2-acetoxy-2-((R)-4-(6-(difluoromethoxy)pyridin-2-yl)-3-oxomorpholin-2-yl)acetate (Compound 19-2)

According to Step 2-3 in the synthetic method for EXAMPLE 2, compound 19-1 (0.45 g) was used instead of compound 1-6 to obtain compound 19-2 as a colorless solid.

Step 19-3: (R)-2-Acetoxy-2-((R)-4-(6-(difluoromethoxy)pyridin-2-yl)-3-oxomorpholin-2-yl)acetic acid (Compound 19-3)

According to Step 1-7 in the synthetic method for EXAMPLE 1, compound 19-2 (0.50 g) was used instead of compound 1-6 to obtain compound 19-3 as a colorless solid.

Step 19-4: (R)-2-((7-Carbamoyl-3-(1,3-dioxoisoindolin-2-yl)benzo[d]isothiazol-6-yl)amino)-1-((R)-4-(6-(difluoromethoxy)pyridin-2-yl)-3-oxomorpholin-2-yl)-2-oxoethyl acetate (Compound 19-4)

According to Step 2-5 in the synthetic method for EXAMPLE 2, compound 19-3 (0.14 g) was used instead of compound 2-4 to obtain compound 19-4 as a pale yellow solid.

Step 19-5: (R)-2-((S)-(3-Amino-9-oxo-6,9-dihydroisothiazolo[5,4-f]quinazolin-7-yl)(hydroxy)methyl)-4-(6-(difluoromethoxy)pyridin-2-yl)morpholin-3-one According to Step 17-5 in the synthetic method for EXAMPLE 17, compound 19-4 (26 mg) was used instead of compound 17-4 to obtain EXAMPLE 19 as a colorless solid.

EXAMPLE 20

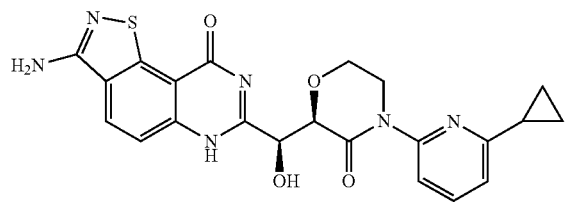 [SMILES: Nc1nsc2c1ccc1[nH]c([C@H](O)[C@H]3OCCN(c4cccc(C5CC5)n4)C3=O)nc(=O)c12]

(R)-2-((S)-(3-Amino-9-oxo-6,9-dihydroisothiazolo[5,4-f]quinazolin-7-yl)(hydroxy)methyl)-4-(6-cyclopropylpyridin-2-yl)morpholin-3-one Step 20-1: (R)-tert-Butyl 2-((R)-4-(6-cyclopropylpyridin-2-yl)-3-oxomorpholin-2-yl)-2-hydroxyacetate (Compound 20-1)

According to Step 1-6 in the synthetic method for EXAMPLE 1,2-bromo-6-cyclopropylpyridine (0.53 g) was used instead of compound 1-5 to obtain compound 20-1 as a colorless solid.

Step 20-2: (R)-tert-Butyl 2-acetoxy-2-((R)-4-(6-cyclopropylpyridin-2-yl)-3-oxomorpholin-2-yl)acetate (Compound 20-2)

According to Step 2-3 in the synthetic method for EXAMPLE 2, compound 20-1 (0.28 g) was used instead of compound 1-6 to obtain compound 20-2 as a colorless oil.

Step 20-3: (R)-2-Acetoxy-2-((R)-4-(6-cyclopropylpyridin-2-yl)-3-oxomorpholin-2-yl)acetic acid hydrochloride (Compound 20-3)

According to Step 1-7 in the synthetic method for EXAMPLE 1, compound 20-2 (0.20 g) was used instead of compound 1-6 to obtain compound 20-3 as a colorless solid.

Step 20-4: (R)-2-((7-Carbamoyl-3-(1,3-dioxoisoindolin-2-yl)benzo[d]isothiazol-6-yl)amino)-1-((R)-4-(6-cyclopropylpyridin-2-yl)-3-oxomorpholin-2-yl)-2-oxoethyl acetate (Compound 20-4)

According to Step 2-5 in the synthetic method for EXAMPLE 2, compound 20-3 (0.21 g) was used instead of compound 2-4 to obtain compound 20-4 as a yellow solid.

Step 20-5: (R)-2-((S)-(3-Amino-9-oxo-6,9-dihydroisothiazolo[5,4-f]quinazolin-7-yl)(hydroxy)methyl)-4-(6-cyclopropylpyridin-2-yl)morpholin-3-one According to Step 9-6 in the synthetic method for EXAMPLE 9, compound 20-4 (40 mg) was used instead of compound 9-5 to obtain EXAMPLE 20 as a colorless solid.

EXAMPLE 21

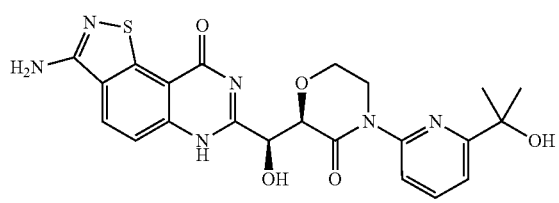 [SMILES: CC(C)(O)c1cccc(N2CCO[C@H]([C@@H](O)c3nc(=O)c4c(ccc5c(N)nsc54)[nH]3)C2=O)n1]

(R)-2-((S)-(3-Amino-9-oxo-6,9-dihydroisothiazolo[5,4-f]quinazolin-7-yl)(hydroxy)methyl)-4-(6-(2-hydroxypropan-2-yl)pyridin-2-yl)morpholin-3-one Step 21-1: 2-(6-Bromopyridin-2-yl)propan-2-ol (Compound 21-1)

Place a 1.6 M solution of n-BuLi in hexane (5.2 mL) in a dry 100 mL round bottomed flask fitted with a stir bar, septum and temperature probe. Cool in a dry-ice acetone bath to −76° C. Add THF (5 mL) to the solution, then add a solution of 2,6-dibromopyridine (2.0 g) in THF (10 mL) slowly via syringe maintaining the temperature under −60° C. Stir the solution for 30 min in the dry-ice bath, then add acetone (13.5 mL). Stir the solution in the dry-ice bath for 15 min then allow the reaction to warm to room temperature. After an h the reaction mixture was quenched with a 5% aqueous solution of NH$_4$Cl, and extracted with EtOAc. The combined organic layer was washed with brine and dried over Na$_2$SO$_4$. It was filtered and concentrated in vacuo. The residue was purified by silica gel column chromatography (Heptane:CH$_2$Cl$_2$=70:30 to 0:100) to obtain compound 21-1 as a orange solid.

Step 21-2: (R)-tert-Butyl 2-hydroxy-2-((R)-4-(6-(2-hydroxypropan-2-yl)pyridin-2-yl)-3-oxomorpholin-2-yl)acetate (Compound 21-2)

According to Step 1-6 in the synthetic method for EXAMPLE 1, compound 21-1 (0.85 g) was used instead of compound 1-5 to obtain compound 21-2 as a colorless solid.

Step 21-3: (R)-tert-Butyl 2-acetoxy-2-((R)-4-(6-(2-hydroxypropan-2-yl)pyridin-2-yl)-3-oxomorpholin-2-yl)acetate (Compound 21-3)

According to Step 2-3 in the synthetic method for EXAMPLE 2, compound 21-2 (0.45 g) was used instead of compound 1-6 to obtain compound 21-3 as a colorless solid.

Step 21-4: (R)(R)-2-Acetoxy-2-((R)-4-(6-(2-hydroxypropan-2-yl)pyridin-2-yl)-3-oxomorpholin-2-yl)acetic acid hydrochloride (Compound 21-4)

According to Step 1-7 in the synthetic method for EXAMPLE 1, compound 21-3 (0.50 g) was used instead of compound 1-6 to obtain compound 21-4 as a colorless solid.

Step 21-5: (R)-2-((7-Carbamoyl-3-(1,3-dioxoisoindolin-2-yl)benzo[d]isothiazol-6-yl)amino)-1-((R)-4-(6-(2-hydroxypropan-2-yl)pyridin-2-yl)-3-oxomorpholin-2-yl)-2-oxoethyl acetate (Compound 21-5)

According to Step 2-5 in the synthetic method for EXAMPLE 2, compound 21-4 (0.11 g) was used instead of compound 2-4 to obtain compound 21-5 as a solid.

Step 21-6: (R)-2-((S)-(3-Amino-9-oxo-6,9-dihydroisothiazolo[5,4-f]quinazolin-7-yl)(hydroxy)methyl)-4-(6-(2-hydroxypropan-2-yl)pyridin-2-yl)morpholin-3-one According to Step 17-5 in the synthetic method for EXAMPLE 17, compound 21-5 (33 mg) was used instead of compound 17-4 to obtain EXAMPLE 21 as a colorless solid.

EXAMPLE 22

(R)-2-((S)-(3-Amino-9-oxo-6,9-dihydroisothiazolo[5,4-f]quinazolin-7-yl)(hydroxy)methyl)-4-(6-(2-hydroxypropan-2-yl)-5-(trifluoromethyl)pyridin-2-yl)morpholin-3-one Step 22-1: 2-(6-Bromo-3-(trifluoromethyl)pyridin-2-yl)propan-2-ol (Compound 22-1)

According to Step 21-1 in the synthetic method for EXAMPLE 21, 2,6-dibromo-3-(trifluoromethyl)pyridine (1.4 g) was used instead of 2,6-dibromopyridine to obtain compound 22-1 as a yellow oil.

Step 22-2: (R)-tert-Butyl 2-hydroxy-2-((R)-4-(6-(2-hydroxypropan-2-yl)-5-(trifluoromethyl)pyridin-2-yl)-3-oxomorpholin-2-yl)acetate (Compound 22-2)

According to Step 1-6 in the synthetic method for EXAMPLE 1, compound 22-1 (0.75 g) was used instead of compound 1-5 to obtain compound 22-2 as a pale yellow solid.

Step 22-3: (R)-tert-Butyl 2-acetoxy-2-((R)-4-(6-(2-hydroxypropan-2-yl)-5-(trifluoromethyl)pyridin-2-yl)-3-oxomorpholin-2-yl)acetate (Compound 22-3)

According to Step 2-3 in the synthetic method for EXAMPLE 2, compound 22-2 (0.12 g) was used instead of compound 1-6 to obtain compound 22-3 as a pale yellow solid.

Step 22-4: (R)-2-Acetoxy-2-((R)-4-(6-(2-hydroxypropan-2-yl)-5-(trifluoromethyl)pyridin-2-yl)-3-oxomorpholin-2-yl)acetic acid hydrochloride (Compound 22-4)

According to Step 1-7 in the synthetic method for EXAMPLE 1, compound 22-3 (0.13 g) was used instead of compound 1-6 to obtain compound 22-4 as a colorless solid.

Step 22-5: (R)-2-((7-Carbamoyl-3-(1,3-dioxoisoindolin-2-yl)benzo[d]isothiazol-6-yl)amino)-1-((R)-4-(6-(2-hydroxypropan-2-yl)-5-(trifluoromethyl)pyridin-2-yl)-3-oxomorpholin-2-yl)-2-oxoethyl acetate (Compound 22-5)

According to Step 2-5 in the synthetic method for EXAMPLE 2, compound 22-4 (0.12 g) was used instead of compound 2-4 to obtain compound 22-5 as a yellow solid.

Step 22-6: (R)-2-((S)-(3-Amino-9-oxo-6,9-dihydroisothiazolo[5,4-f]quinazolin-7-yl)(hydroxy)methyl)-4-(6-(2-hydroxypropan-2-yl)-5-(trifluoromethyl)pyridin-2-yl)morpholin-3-one According to Step 17-5 in the synthetic method for EXAMPLE 17, compound 22-5 (34 mg) was used instead of compound 17-4 to obtain EXAMPLE 22 as a pale yellow solid.

EXAMPLE 23

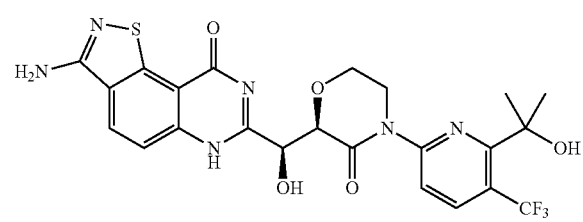 [SMILES: CC(C)(O)c1nc(N2CCO[C@H]([C@@H](O)c3nc(=O)c4c(ccc5c(N)nsc54)[nH]3)C2=O)ccc1C(F)(F)F]

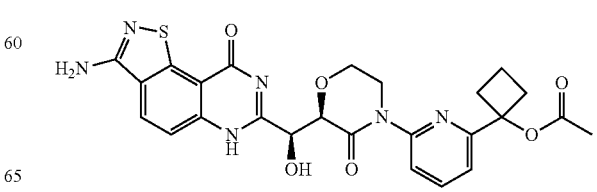

1-(6-((R)-2-((S)-(3-Amino-9-oxo-6,9-dihydroisothi-
azolo[5,4-f]quinazolin-7-yl)(hydroxy)methyl)-3-
oxomorpholino)pyridin-2-yl)cyclobutyl acetate Step 23-1: 1-(6-bromopyridin-2-yl)cyclobutanol (Compound 23-1)

According to Step 21-1 in the synthetic method for EXAMPLE 21, cyclobutanone (1.0 mL) was used instead of acetone to obtain compound 23-1 as a yellow oil.

Step 23-2: (R)-tert-Butyl 2-hydroxy-2-((R)-4-(6-(1-hydroxycyclobutyl)pyridin-2-yl)-3-oxomorpholin-2-yl)acetate (Compound 23-2)

According to Step 1-6 in the synthetic method for EXAMPLE 1, compound 23-1 (0.83 g) was used instead of compound 1-5 to obtain compound 23-2.

Step 23-3: (R)-tert-Butyl 2-acetoxy-2-((R)-4-(6-(1-acetoxycyclobutyl)pyridin-2-yl)-3-oxomorpholin-2-yl)acetate (Compound 23-3)

According to Step 2-3 in the synthetic method for EXAMPLE 2, compound 23-2 (0.45 g) was used instead of compound 1-6 to obtain compound 23-3 as a solid.

Step 23-4: (R)-2-Acetoxy-2-((R)-4-(6-(1-acetoxycyclobutyl)pyridin-2-yl)-3-oxomorpholin-2-yl)acetic acid (Compound 23-4)

According to Step 1-7 in the synthetic method for EXAMPLE 1, compound 22-3 (0.58 g) was used instead of compound 1-6 to obtain compound 23-4.

Step 23-5: 1-(6-((R)-2-((R)-1-Acetoxy-2-((7-carbamoyl-3-(1,3-dioxoisoindolin-2-yl)benzo[d]isothiazol-6-yl)amino)-2-oxoethyl)-3-oxomorpholino)pyridin-2-yl)cyclobutyl acetate (Compound 23-5)

According to Step 2-5 in the synthetic method for EXAMPLE 2, compound 23-4 (0.15 g) was used instead of compound 2-4 to obtain compound 23-5.

Step 23-6: 1-(6-((R)-2-((S)-(3-Amino-9-oxo-6,9-dihydroisothiazolo[5,4-f]quinazolin-7-yl)(hydroxy)methyl)-3-oxomorpholino)pyridin-2-yl)cyclobutyl acetate According to Step 9-5 in the synthetic method for EXAMPLE 9, compound 23-5 (61 mg) was used instead of compound 9-4 to obtain EXAMPLE 23 as a solid.

EXAMPLE 24

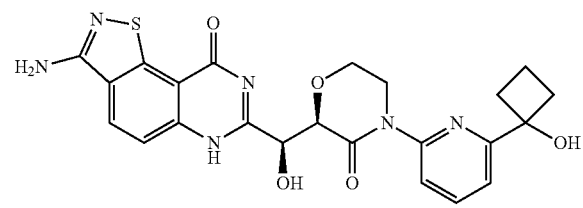 [SMILES: Nc1nsc2c1ccc1[nH]c([C@H](O)[C@H]3OCCN(c4cccc(C5(O)CCC5)n4)C3=O)nc(=O)c12]

(R)-2-((S)-(3-Amino-9-oxo-6,9-dihydroisothiazolo
[5,4-f]quinazolin-7-yl)(hydroxy)methyl)-4-(6-(1-
hydroxycyclobutyl)pyridin-2-yl)morpholin-3-one Step 24-1: (R)-tert-Butyl 2-acetoxy-2-((R)-4-(6-(1-hydroxycyclobutyl)pyridin-2-yl)-3-oxomorpholin-2-yl)acetate (Compound 24-1)

According to Step 2-3 in the synthetic method for EXAMPLE 2, compound 23-2 (0.38 g) was used instead of compound 1-6 to obtain compound 24-1.

Step 24-2: (R)-2-Acetoxy-2-((R)-4-(6-(1-hydroxycyclobutyl)pyridin-2-yl)-3-oxomorpholin-2-yl)acetic acid hydrochloride (Compound 24-2)

According to Step 1-7 in the synthetic method for EXAMPLE 1, compound 24-1 (0.43 g) was used instead of compound 1-6 to obtain compound 24-2 as a solid.

Step 24-3: (R)-2-((7-Carbamoyl-3-(1,3-dioxoisoindolin-2-yl)benzo[d]isothiazol-6-yl)amino)-1-((R)-4-(6-(1-hydroxycyclobutyl)pyridin-2-yl)-3-oxomorpholin-2-yl)-2-oxoethyl acetate (Compound 24-3)

According to Step 2-5 in the synthetic method for EXAMPLE 2, compound 24-2 (0.15 g) was used instead of compound 2-4 to obtain compound 24-3 as a solid.

Step 24-4: (R)-2-((S)-(3-amino-9-oxo-6,9-dihydroisothiazolo[5,4-f]quinazolin-7-yl)(hydroxy)methyl)-4-(6-(1-hydroxycyclobutyl)pyridin-2-yl)morpholin-3-one According to Step 9-6 in the synthetic method for EXAMPLE 9, compound 24-3 (47 mg) was used instead of compound 9-5 to obtain EXAMPLE 24 as a solid.

EXAMPLE 25

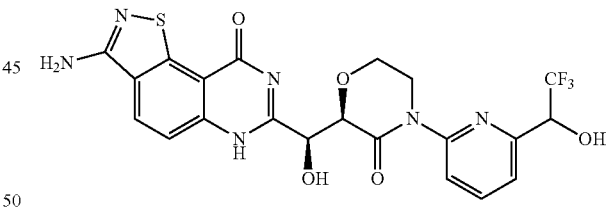

(2R)-2-((S)-(3-Amino-9-oxo-6,9-dihydroisothiazolo
[5,4-f]quinazolin-7-yl)(hydroxy)methyl)-4-(6-(2,2,2-
trifluoro-1-hydroxyethyl)pyridin-2-yl)morpholin-3-
one Step 25-1: 1-(6-Bromopyridin-2-yl)-2,2,2-trifluoroethanol (Compound 25-1)

To a solution of 6-bromopyridine-2-carbaldehyde (2.0 g) in THF (70 mL), were added trifluoromethyltrimethylsilane (1.9 mL) and 1 M solution of TBAF in THF (12.9 mL) at 0° C. and stirred at room temperature for 4 h. The reaction mixture was diluted with brined and extracted with EtOAc. The combined organic layer was dried over $Na_2SO_4$, filtered, and concentrated in vacuo. The residue was purified by silica gel column chromatography (Hexane: EtOAc=100:0 to 70:30) to obtain compound 25-1 as a colorless solid.

Step 25-2: (2R)-tert-Butyl 2-hydroxy-2-((2R)-3-oxo-4-(6-(2,2,2-trifluoro-1-hydroxyethyl)pyridin-2-yl)morpholin-2-yl)acetate (Compound 25-2)

According to Step 1-6 in the synthetic method for EXAMPLE 1, compound 25-1 (0.77 g) was used instead of compound 1-5 to obtain compound 25-2.

Step 25-3: (2R)-tert-butyl 2-acetoxy-2-((2R)-4-(6-(1-acetoxy-2,2,2-trifluoroethyl)pyridin-2-yl)-3-oxomorpholin-2-yl)acetate (Compound 25-3)

According to Step 2-3 in the synthetic method for EXAMPLE 2, compound 25-2 (0.19 g) was used instead of compound 1-6 to obtain compound 25-3 as a colorless solid.

Step 25-4: (2R)-2-acetoxy-2-((R)-4-(6-(1-acetoxy-2,2,2-trifluoroethyl)pyridin-2-yl)-3-oxomorpholin-2-yl)acetic acid (Compound 25-4)

A solution of compound 25-3 (0.21 g) in 4M HCl-dioxane (4.3 mL) was stirred overnight at room temperature. The organic solvent was evaporated under reduced pressure, and the residue and DMAP (7.7 mg) was dissolved in $CH_2Cl_2$ (6.3 mL). Pyridine (0.15 mL) and acetic anhydride (0.18 mL) were added to the mixture at 0° C. and stirred at room temperature for 4 h. After stirring, the mixture was concentrated in vacuo and the residue was purified by silica gel column chromatography ($CH_2Cl_2$:MeOH=90:10) to obtain compound 25-4.

Step 25-5: (1R)-1-((2R)-4-(6-(1-acetoxy-2,2,2-trifluoroethyl)pyridin-2-yl)-3-oxomorpholin-2-yl)-2-((7-carbamoyl-3-(1,3-dioxoisoindolin-2-yl)benzo[d]isothiazol-6-yl)amino)-2-oxoethyl acetate (Compound 25-5)

According to Step 2-5 in the synthetic method for EXAMPLE 2, compound 25-4 (0.16 g) was used instead of compound 2-4 to obtain compound 25-5 as a solid.

Step 25-6: (2R)-2-((S)-(3-amino-9-oxo-6,9-dihydroisothiazolo[5,4-f]quinazolin-7-yl)(hydroxy)methyl)-4-(6-(2,2,2-trifluoro-1-hydroxyethyl)pyridin-2-yl)morpholin-3-one According to Step 9-6 in the synthetic method for EXAMPLE 9, compound 25-5 (80 mg) was used instead of compound 9-5 to obtain EXAMPLE 25 as a solid.

EXAMPLE 26

(2R)-2-((S)-(3-Amino-9-oxo-6,9-dihydroisothiazolo[5,4-f]quinazolin-7-yl)(hydroxy)methyl)-4-(6-(1,1,1-trifluoro-2-hydroxypropan-2-yl)pyridin-2-yl)morpholin-3-one Step 26-1: 2-(6-Bromopyridin-2-yl)-1,1,1-trifluoropropan-2-ol (Compound 26-1)

According to Step 25-1 in the synthetic method for EXAMPLE 25, 2-acetyl-6-bromopyridine (3.1 g) was used instead of 6-bromopyridine-2-carbaldehyde to obtain compound 26-1 as a pale yellow oil.

Step 26-2: (2R)-tert-Butyl 2-hydroxy-2-((R)-3-oxo-4-(6-(1,1,1-trifluoro-2-hydroxypropan-2-yl)pyridin-2-yl)morpholin-2-yl)acetate (Compound 26-2)

According to Step 1-6 in the synthetic method for EXAMPLE 1, compound 26-1 (1.0 g) was used instead of compound 1-5 to obtain compound 26-2 as a colorless oil.

Step 26-3: (2R)-tert-Butyl 2-acetoxy-2-((2R)-3-oxo-4-(6-(1,1,1-trifluoro-2-hydroxypropan-2-yl)pyridin-2-yl)morpholin-2-yl)acetate (Compound 26-3)

According to Step 2-3 in the synthetic method for EXAMPLE 2, compound 26-2 (0.13 g) was used instead of compound 1-6 to obtain compound 26-3.

Step 26-4: (2R)-2-Acetoxy-2-((2R)-3-oxo-4-(6-(1,1,1-trifluoro-2-hydroxypropan-2-yl)pyridin-2-yl)morpholin-2-yl)acetic acid (Compound 26-4)

According to Step 1-7 in the synthetic method for EXAMPLE 1, compound 26-3 (0.11 g) was used instead of compound 1-6 to obtain compound 26-4.

Step 26-5: (1R)-2-((7-Carbamoyl-3-(1,3-dioxoisoindolin-2-yl)benzo[d]isothiazol-6-yl)amino)-2-oxo-1-((2R)-3-oxo-4-(6-(1,1,1-trifluoro-2-hydroxypropan-2-yl)pyridin-2-yl)morpholin-2-yl)ethyl acetate (Compound 26-5)

According to Step 2-5 in the synthetic method for EXAMPLE 2, compound 26-4 (0.23 g) was used instead of compound 2-4 to obtain compound 26-5 as a yellow solid.

Step 26-6: (2R)-2-((S)-(3-amino-9-oxo-6,9-dihydroisothiazolo[5,4-f]quinazolin-7-yl)(hydroxy)methyl)-4-(6-(1,1,1-trifluoro-2-hydroxypropan-2-yl)pyridin-2-yl)morpholin-3-one According to Step 9-6 in the synthetic method for EXAMPLE 9, compound 26-5 (25 mg) was used instead of compound 9-5 to obtain EXAMPLE 26 as a colorless solid.

EXAMPLE 27

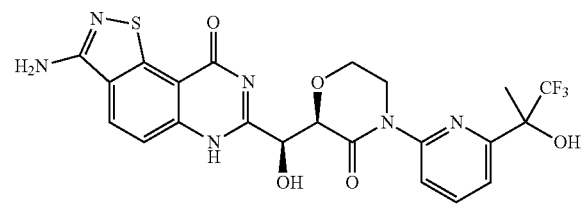 [SMILES: CC(O)(c1cccc(N2CCO[C@H]([C@@H](O)c3nc(=O)c4c(ccc5c(N)nsc54)[nH]3)C2=O)n1)C(F)(F)F]

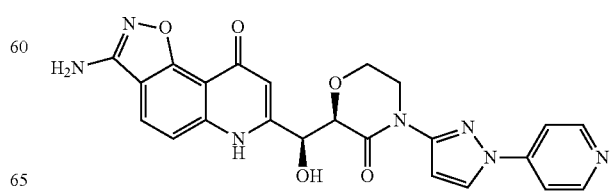

3-Amino-7-((S)-hydroxy((R)-3-oxo-4-(1-(pyridin-4-yl)-1H-pyrazol-3-yl)morpholin-2-yl)methyl)isoxazolo[5,4-f]quinolin-9(6H)-one

Step 27-1: 1-(6-amino-2-fluoro-3-iodophenyl)ethanone (Compound 27-1)

According to Step 1-2 in the synthetic method for EXAMPLE 1, 1-(2-amino-6-fluorophenyl)ethanone (0.16 g) was used instead of compound 1-1 to obtain compound 27-1 as an orange solid.

Step 27-2: Methyl 5-fluoro-6-iodo-4-oxo-1,4-dihydroquinoline-2-carboxylate (Compound 27-2)

A mixture of compound 27-1 (3.4 g), dimethyl oxalate (5.8 g) and sodium methoxide (2.7 g) in MeOH (123 mL) was stirred under reflux condition for 4 h. The reaction mixture was cooled to room temperature and poured into sat.NH$_4$Cl. Then EtOAc was added and the mixture was stirred. The precipitate was filtered and dried to give compound 27-2 as a purple solid.

Step 27-3: Methyl 5-fluoro-6-iodo-4-((4-methoxybenzyl)oxy)quinoline-2-carboxylate (Compound 27-3)

A mixture of 27-2 (2.1 g), KI (0.05 g) and K$_2$CO$_3$ (1.7 g) in DMF (30 mL) was added paramethoxybenzylchloride (2.8 g) and stirred at 19 h. Water and EtOAc were added with stirring. The precipitate was filtered and dried to give 27-3 (0.84 g) as a pale yellow solid. The filtrate was extracted with EtOAc. The combined organic layer was washed with brine and dried over Na$_2$SO$_4$, filtered and concentrated in vacuo. The residue was purified by silica gel column chromatography (Heptane:EtOAc=65:35 to 0:100), and then triturated with diethyl ether to obtain compound 27-3 as a pale yellow solid.

Step 27-4: (5-Fluoro-6-iodo-4-((4-methoxybenzyl)oxy)quinolin-2-yl)methanol (Compound 27-4)

To a suspension of compound 27-3 (0.83 g) in THF (18 mL) and EtOH (18 mL), were added LiCl (90 mg) and NaBH$_4$ (81 mg) at 0° C. and stirred at room temperature for 2 h. The reaction mixture was quenched with sat.NH$_4$Cl and extracted with EtOAc. The combined organic layer was washed with brine and dried over Na$_2$SO$_4$, filtered and concentrated in vacuo to give compound 27-4 as a pale yellow solid.

Step 27-5: 5-Fluoro-6-iodo-4-((4-methoxybenzyl)oxy)quinoline-2-carbaldehyde (Compound 27-5)

To a suspension of compound 27-4 (0.70 g) in CH$_2$Cl$_2$ (35 mL), was added Dess-Martin Periodinane (0.81 g) at 0° C. and stirred at room temperature for 2 h. The reaction mixture was diluted with CH$_2$Cl$_2$ and added sat.NaHCO$_3$ and Na$_2$S$_2$O$_3$ aq. The mixture was stirred for 30 min and extracted with CH$_2$Cl$_2$. The combined organic layer was washed with brine and dried over Na$_2$SO$_4$, filtered and concentrated in vacuo to give compound 27-5 as a pale yellow solid.

Step 27-6: 4-(1-(Pyridin-4-yl)-1H-pyrazol-3-yl)morpholin-3-one (Compound 27-6)

According to Step 1-6 in the synthetic method for EXAMPLE 1, morpholin-3-one (0.22 g) was used instead of compound 1-5 to obtain compound 27-6 as a colorless solid.

Step 27-7: 2-((5-Fluoro-6-iodo-4-(4-methoxybenzyl)oxy)quinolin-2-yl)(hydroxy)methyl)-4-(1-(pyridin-4-yl)-1H-pyrazol-3-yl)morpholin-3-one (Compound 27-7)

To a solution of diisopropylamine (21 uL) in THF (0.5 mL) was added n-BuLi (1.6 M solution in hexane, 75 uL) at 0° C. and stirred for 30 min at the same temperature. The mixture was cooled to −78° C. and added a suspension of compound 27-6 (30 mg) in THF (2 mL). The mixture was stirred for 30 min at the same temperature. A suspension of 27-5 (27 mg) in THF (2 mL) was added dropwise to the reaction mixture, and stirred at room temperature for 40 min. The reaction mixture was quenched with sat.NH$_4$Cl and extracted with CH$_2$Cl$_2$. The combined organic layer was washed with brine and dried over Na$_2$SO$_4$, filtered and concentrated in vacuo. The residue was purified by silica gel column chromatography (CH$_2$Cl$_2$:MeOH=99:1~97:3) to give compound 27-7 including inseparable impurities.

Step 27-8: 5-Fluoro-2-(hydroxy(3-oxo-4-(1-(pyridin-4-yl)-1H-pyrazol-3-yl)morpholin-2-yl)methyl)-4-((4-methoxybenzyl)oxy)quinoline-6-carbonitrile (Compound 27-8)

Under nitrogen atmosphere, a mixture of compound 27-7 (36 mg), Zn(CN)$_2$ (7.5 mg), Pd(PPh$_3$)$_4$ (6.1 mg) and Zn (2.5 mg) in DMF (2 mL) was stirred at 80° C. overnight. The reaction mixture was cooled to room temperature and extracted with CH$_2$Cl$_2$. The combined organic layer was washed with brine and dried over Na$_2$SO$_4$, filtered and concentrated in vacuo. The residue was purified by silica gel column chromatography (CH$_2$Cl$_2$:MeOH=100:0 to 90:10) to give compound 27-8 as a mixture of diastereoisomers.

Step 27-9: 2-((3-Amino-9-((4-methoxybenzyl)oxy)isoxazolo[5,4-f]quinolin-7-yl)(hydroxy)methyl)-4-(1-(pyridin-4-yl)-1H-pyrazol-3-yl)morpholin-3-one (Compound 27-9)

A solution of compound 27-8 (25 mg), acetohydroxamic acid (4.9 mg) in DMF (2 mL) was added KOtBu (7.3 mg) and stirred at room temperature for 1 h. The reaction mixture was poured into sat.NH$_4$Cl and extracted with CH$_2$Cl$_2$. The combined organic layer was washed with brine and dried over Na$_2$SO$_4$, filtered and concentrated in vacuo. The residue was purified by silica gel column chromatography (CH$_2$Cl$_2$:MeOH=99:1~95:5) to give compound 27-9 as a mixture of diastereoisomers.

Step 27-10: 3-Amino-7-(hydroxy(3-oxo-4-(1-(pyridin-4-yl)-1H-pyrazol-3-yl)morpholin-2-yl)methyl)isoxazolo[5,4-f]quinolin-9(6H)-one (Compound 27-10)

A solution of compound 27-9 (7 mg) in TFA (1 mL) and CH$_2$Cl$_2$ (1 mL) was stirred at room temperature for 5 h and at 40° C. for 10 h. The reaction mixture was concentrated in vacuo and remaining TFA was azeotropically removed with toluene. The residue was triturated with EtOAc to give compound 27-10 as a mixture of diastereoisomers.

Step 27-11: 3-Amino-7-((S)-hydroxy((R)-3-oxo-4-(1-(pyridin-4-yl)-1H-pyrazol-3-yl)morpholin-2-yl)methyl)isoxazolo[5,4-f]quinolin-9(6H)-one Chiral resolution of compound 27-10 (diastereomer mixture) was conducted the following condition.
System Waters Fraction Lynx System (LC-3)
Solvent Hexane/EtOH=1:1
Column Daicel CHIRALPAK AS-H Φ20×250 mm (Lot ASH0CJ-PA002) with precolumn Φ10×20 mm (Lot ASH0CX-OK003)
Flow Rate: 4.5 (mL/min), Temperature: 40 deg C., Run Time: 200 (min), Sample Concentration: 2.5 (mg/mL), Injection Volume: 2500 (uL)
Chiral resolution of compound 27-10 gave to 1st peak: EXAMPLE 27 as colorless solid, 2nd peak as colorless solid, 3rd peak as colorless solid and 4th peak as colorless solid. Optical purity of each compounds were 100% ee.

EXAMPLE 28

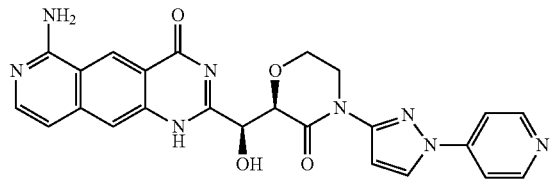 [SMILES: Nc1nccc2cc3[nH]c([C@H](O)[C@H]4OCCN(c5ccn(-c6ccncc6)n5)C4=O)nc(=O)c3cc12]

(R)-2-((S)-(6-Amino-4-oxo-1,4-dihydropyrido[3,4-g]quinazolin-2-yl)(hydroxy)methyl)-4-(1-(pyridin-4-yl)-1H-pyrazol-3-yl)morpholin-3-one Step 28-1: 6-Amino-1-chloroisoquinoline-7-carbonitrile (Compound 28-1)

6-Amino-7-cyano-2H-isoquinoline-1-one (0.34 g, WO20080365540) was added to stirring $POCl_3$ (1.68 mL) at 0° C. The reaction mixture was stirred for 3 h at 100° C., then it was cooled to room temperature and poured over ice. After the pH adjustment to pH 8 by 1N NaOH aq., it was extracted with dichloromethane. The residue was triturated with hexane and EtOAc to give compound 28-4 as a beige solid.

Step 28-2: 6-Amino-1-((4-methoxybenzyl)amino)isoquinoline-7-carbonitrile (Compound 28-2)

To a solution of compound 28-1 (87 mg) in DMF (4.4 mL) was added 4-mehtoxybenzylamine (114 uL) and $Na_2CO_3$ (226 mg). The reaction mixture was stirred for 6 h at 60° C. After cooling to room temperature, it was diluted with water and extracted with EtOAc. The organic layer was washed with brine, dried over $Na_2SO_4$, filtered and concentrated. The residue was purified by N—H silica gel flash chromatography (eluent:Hexane:EtOAc=50:50~0:100) to give compound 28-2 as a solid.

Step 28-3: 6-Amino-1-((4-methoxybenzyl)amino)isoquinoline-7-carboxamide (Compound 28-3)

To a solution of 28-2 (43 mg) in EtOH (2.5 mL) was added 2M NaOH aq. (1.3 mL) and 30% $H_2O_2$ aq. (51.6 uL). The reaction mixture was stirred for 15 h at room temperature. The mixture was diluted with water and extracted with EtOAc. The organic layer was washed with brine, dried over $Na_2SO_4$, filtered and concentrated to give compound 28-3 as a solid, which was used in the next step without further purification.

Step 28-4: (R)-2-((7-Carbamoyl-1-((4-methoxybenzyl)amino)isoquinolin-6-yl)amino)-2-oxo-1-((R)-3-oxo-4-(1-(pyridin-4-yl)-1H-pyrazol-3-yl)morpholin-2-yl)ethyl acetate (Compound 28-4)

According to Step 1-8 in the synthetic method for EXAMPLE 1, compound 28-3 (32 mg) and compound 2-4 (59 mg) were used instead of compound 1-4 and 1-7 to obtain compound 28-4 as a solid.

Step 28-5: (R)-2-((S)-Hydroxy(6-((4-methoxybenzyl)amino)-4-oxo-1,4-dihydropyrido[3,4-g]quinazolin-2-yl)methyl)-4-(1-(pyridin-4-yl)-1H-pyrazol-3-yl)morpholin-3-one (Compound 28-5)

According to Step 1-9 in the synthetic method for EXAMPLE 1, compound 28-4 (20 mg) was used instead of compound 1-8 to obtain compound 28-5 as a solid.

Step 28-6: (R)-2-((S)-(6-Amino-4-oxo-1,4-dihydropyrido[3,4-g]quinazolin-2-yl)(hydroxy)methyl)-4-(1-(pyridin-4-yl)-1H-pyrazol-3-yl)morpholin-3-one According to Step 27-10 in the synthetic method for EXAMPLE 27, compound 28-5 (13 mg) was used instead of compound 27-9 to obtain EXAMPLE 28 as a yellow solid.

TABLE 1

| EXAMPLE | NMR (ppm) (No mark: 400 MHz, *: 300 MHz) |
|---|---|
| 1-1 | DMSO-$d_6$: 7.60-7.42 (2H, m), 7.11-7.01 (1H, m), 6.49 (1H, d, J = 8 Hz), 6.34-6.25 (1H, m), 6.15 (2H, s) |
| 1-2 | *DMSO-$d_6$: 7.75-7.53 (2H, m), 7.40 (1H, dd, J = 9, 7 Hz), 6.90-6.46 (2H, m), 6.40 (1H, dd, J = 9, 1Hz) |
| 1-3 | DMSO-$d_6$: 7.90-7.72 (2H, m), 7.45 (1H, dd, J = 9, 8 Hz), 6.99 (2H, s), 6.58 (1H, d, J = 9Hz) |
| 1-4 | DMSO-$d_6$: 7.61-7.43 (4H, m), 7.20-7.07 (1H, m), 6.59 (1H, d, J = 9 Hz), 6.18 (2H, s) |
| 1-5 | *CDCl$_3$: 8.70-8.63 (2H, m), 7.85 (1H, d, J = 3 Hz), 7.63-7.58 (2H, m), 6.70-6.67 (1H, m) |
| 1-6 | CDCl$_3$: 8.64-8.61 (2H, m), 7.98 (1H, d, J = 3 Hz), 7.58-7.55 (2H, m), 7.28 (1H, d, J = 3 Hz), 4.77 (1H, dd, J = 7, 2 Hz), 4.64 (1H, d, J = 2 |

TABLE 1-continued

| EXAMPLE | NMR (ppm) (No mark: 400 MHz, *: 300 MHz) |
|---|---|
|  | Hz), 4.33-4.20 (2H, m), 4.15-3.93 (2H, m), 3.23 (1H, d, J = 7 Hz), 1.52 (9H, s) |
| 1-7 | *DMSO-$d_6$: 8.92 (1H, d, J = 3 Hz), 8.88 (2H, d, J = 7 Hz), 8.25 (2H, d, J = 7 Hz), 7.27 (1H, d, J = 3 Hz), 4.69 (1H, d, J = 2 Hz), 4.55 (1H, d, J = 2 Hz), 4.25-3.90 (4H, m) |
| 1-8 | *DMSO-$d_6$: 12.56 (1H, s), 8.71 (1H, d, J = 3 Hz), 8.66-8.59 (3H, m), 8.10 (1H, s), 7.93 (1H, d, J = 9 Hz), 7.87-7.75 (3H, m), 7.15 (1H, d, J = 3 Hz), 6.63 (1H, d, J = 7 Hz), 6.59-6.51 (2H, m), 4.77 (1H, d, J = 2 Hz), 4.68 (1H, dd, J = 7, 2 Hz), 4.28-3.86 (4H, m) |
| 1 | *DMSO-$d_6$: 11.94 (1H, s), 8.72 (1H, d, J = 3 Hz), 8.63 (2H, d, J = 6 Hz), 8.12 (1H, d, J = 8 Hz), 7.84 (2H, d, J = 6 Hz), 7.51-7.42 (1H, m), 7.16 (1H, d, J = 3 Hz), 6.53 (2H, s), 6.29-6.17 (1H, m), 5.18-5.12 (1H, m), 4.85 (1H, d, J = 2 Hz), 4.25-3.90 (4H, m) |
| 2-1 | DMSO-$d_6$: 7.77 (1H, d, J = 9 Hz), 7.35 (2H, s), 6.81-6.73 (1H, m), 6.43-6.26 (4H, m) |
| 2-2 | *DMSO-$d_6$: 8.11-7.92 (4H, m), 7.78 (1H, d, J = 9 Hz), 7.66-7.56 (2H, m), 6.95 (1H, d, J = 9 Hz), 6.66-6.54 (2H, m) |
| 2-3 | CDCl$_3$: 8.66-8.62 (2H, m), 7.99 (1H, d, J = 3 Hz), 7.59-7.56 (2H, m), 7.23 (1H, d, J = 3 Hz), 5.70 (1H, d, J = 2 Hz), 4.87 (1H, d, J = 2 Hz), 4.37-4.30 (1H, m), 4.25-4.13 (2H, m), 4.04-3.95 (1H, m), 2.11 (3H, s), 1.51 (9H, s) |
| 2-5 | DMSO-$d_6$: 10.72 (1H, s), 8.73 (1H, d, J = 3 Hz), 8.64 (2H, d, J = 6 Hz), 8.32-8.26 (1H, m), 8.10-8.04 (2H, m), 8.01-7.96 (2H, m), 7.85 (2H, d, J = 6 Hz), 7.68 (1H, d, J = 9 Hz), 7.10 (1H, d, J = 3 Hz), 5.67 (1H, d, J = 2 Hz), 5.10-5.05 (1H, m), 4.36-3.96 (4H, m), 2.14 (3H, s) |
| 2 | DMSO-$d_6$: 12.31 (1H, br s), 8.73 (1H, d, J = 3 Hz), 8.66-8.61 (2H, m), 8.40 (1H, d, J = 9 Hz), 7.86-7.81 (2H, m), 7.65-7.57 (1H, m), 7.17 (1H, d, J = 3 Hz), 6.86 (2H, s), 6.29 (1H, br s), 5.23-5.19 (1H, m), 4.88 (1H, d, J = 2 Hz), 4.24-3.90 (4H, m) |
| 4-1 | *CDCl$_3$: 8.73-8.70 (1H, m), 8.64 (1H, dd, J = 5, 1 Hz), 7.84-7.78 (1H, m), 7.43 (1H, ddd, J = 8, 5, 1 Hz), 6.41-6.39 (1H, m), 2.36 (3H, d, J = 1 Hz) |
| 9 | *DMSO-$d_6$: 12.33 (1H, br s), 9.84-9.81 (1H, m), 9.27 (1H, d, J = 6 Hz), 8.83 (1H, d, J = 3 Hz), 8.41 (1H, d, J = 9 Hz), 8.04 (1H, dd, J = 6, 3 Hz), 7.70-7.56 (1H, m), 7.24 (1H, d, J = 3 Hz), 6.86 (2H, s), 6.32 (1H, br s), 5.25-5.18 (1H, m), 4.89 (1H, d, J = 2 Hz), 4.27-3.90 (4H, m) |
| 10-2 | CDCl$_3$: 7.81 (1H, d, J = 3 Hz), 7.75 (1H, dd, J = 10, 3 Hz), 7.69 (1H, t, J = 60 Hz), 7.56-7.53 (1H, m), 6.68 (1H, d, J = 10 Hz), 6.63 (1H, d, J = 3 Hz) |
| 14-1 | *CDCl$_3$: 6.17 (1H, s), 3.79 (3H, s), 2.26 (3H, s) |
| 17 | *DMSO-$d_6$: 12.32 (1H, br s), 8.44-8.35 (2H, m), 8.16 (1H, dd, J = 8, 8 Hz), 7.81-7.73 (1H, m), 7.67-7.55 (1H, m), 6.85 (2H, s), 6.30 (1H, br s), 5.24-5.16 (1H, m), 4.90 (1H, d, J = 2 Hz), 4.25-3.88 (4H, m) |
| 21-1 | CDCl$_3$: 7.55 (1H, dd, J = 8, 8 Hz), 7.37 (1H, d, J = 8 Hz), 7.35 (1H, d, J = 8 Hz), 4.08 (1H, s), 1.55 (6H, s) |
| 25-1 | CDCl$_3$: 7.65 (1H, dd, J = 8, 8 Hz), 7.57 (1H, d, J = 8 Hz), 7.42-7.38 (1H, m), 5.06-4.98 (1H, m), 4.77 (1H, d, J = 8 Hz) |
| 25-4 | DMSO-$d_6$: 8.04-7.92 (2H, m), 7.46 (1H, d, J = 7 Hz), 6.32 (1H, q, J = 7 Hz), 5.37 (1H, s), 4.94-4.88 (1H, m), 4.22-3.79 (4H, m), 2.24 (3H, s), 1.99 (3H, s) |
| 27-2 | *DMSO-$d_6$: 12.01 (1H, br s), 8.01 (1H, dd, J = 9, 6 Hz), 7.58 (1H, d, J = 9 Hz), 6.62 (1H, s), 3.94 (3H, s) |
| 27-3 | DMSO-$d_6$: 8.15 (1H, dd, J = 9, 6 Hz), 7.74-7.70 (2H, m), 7.49 (2H, d, J = 9 Hz), 7.04-6.99 (2H, m), 5.39 (2H, s), 3.95 (3H, s), 3.78 (3H, s) |
| 27-4 | DMSO-$d_6$: 8.00 (1H, dd, J = 9, 6 Hz), 7.54-7.46 (3H, m), 7.33 (1H, s), 7.01 (2H, d, J = 9 Hz), 5.65 (1H, t, J = 6 Hz), 5.30 (2H, s), 4.64 (2H, d, J = 6 Hz), 3.78 (3H, s) |
| 27-5 | CDCl$_3$: 10.10 (1H, s), 8.04 (1H, dd, J = 9, 6 Hz), 7.74 (1H, d, J = 9 Hz), 7.49 (1H, s), 7.46 (2H, d, J = 9 Hz), 6.97 (2H, d, J = 9 Hz), 5.30 (2H, s), 3.84 (3H, s) |
| 27-7 | DMSO-$d_6$: 8.75-8.68 (1H, m), 8.66-8.60 (2H, m), 8.06-7.79 (3H, m), 7.59-7.36 (4H, m), 7.22-7.07 (1H, m), 7.04-6.95 (2H, m), 6.37-6.02 (1H, m), 5.39-5.22 (3H, m), 4.90-4.81 (1H, m), 4.17-3.82 (4H, m), 3.80-3.76 (3H, m) |
| 27-8 | DMSO-$d_6$: 8.74-8.68 (1H, m), 8.65-8.60 (2H, m), 8.04-7.79 (3H, m), 7.65-7.45 (4H, m), 7.22-7.07 (1H, m), 7.03-6.96 (2H, m), 6.23-6.00 (1H, m), 5.42-5.29 (3H, m), 4.91-4.84 (1H, m), 4.15-3.81 (4H, m), 3.79-3.75 (3H, m) |
| 27-9 | DMSO-$d_6$: 8.76-8.71 (1H, m), 8.66-8.61 (2H, m), 8.04-7.79 (3H, m), 7.73-7.43 (4H, m), 7.26-7.10 (1H, m), 7.05-6.96 (2H, m), 6.50-6.35 (2H, m), 6.31-6.05 (1H, m), 5.47-5.32 (3H, m), 4.93-4.82 (1H, m), 4.16-3.76 (7H, m) |
| 27-10 | DMSO-$d_6$: 11.97-11.66 (1H, m), 8.86-8.68 (3H, m), 8.07-7.58 (4H, m), 7.27-7.12 (1H, m), 6.48-6.27 (4H, m), 5.33-5.20 (1H, m), 4.83-4.72 (1H, m), 4.26-3.88 (4H, m) |
| 27 | DMSO-$d_6$: 11.75 (1H, s), 8.76 (1H, d, J = 3 Hz), 8.71-8.61 (2H, m), 7.94-7.86 (3H, m), 7.60 (1H, d, J = 9 Hz), 7.19 (1H, d, J = 3 Hz), |

TABLE 1-continued

| EXAMPLE | NMR (ppm) (No mark: 400 MHz, *: 300 MHz) |
|---|---|
|  | 6.43-6.26 (4H, m), 5.28 (1H, d, J = 3 Hz), 4.75-4.71 (1H, m), 4.25-3.87 (4H, m) |
| 28-1 | *DMSO-$d_6$: 8.45 (1H, s), 8.03 (1H, d, J = 6 Hz), 7.49 (1H, d, J = 6 Hz), 7.05 (1H, s), 6.77 (2H, s) |
| 28-2 | *DMSO-$d_6$: 8.59 (1H, s), 7.88-7.81 (1H, m), 7.67 (1H, d, J = 6 Hz), 7.26 (2H, d, J = 9 Hz), 6.85 (2H, d, J = 9 Hz), 6.76 (1H, s), 6.54 (1H, dd, J = 6, 1 Hz), 6.20 (2H, s), 4.58 (2H, d, J = 6 Hz), 3.71 (3H, s) |
| 28-3 | *DMSO-$d_6$: 8.52 (1H, s), 7.86-7.77 (1H, m), 7.69 (1H, d, J = 6 Hz), 7.50-7.33 (4H, m), 6.97-6.91 (2H, m), 6.79 (2H, s), 6.74 (1H, s), 6.57 (1H, d, J = 6 Hz), 4.69 (2H, d, J = 6 Hz), 3.78 (3H, s) |

TABLE 2

| EXAMPLE | LC/MS m/z [M + 1]$^+$ | RT min | Method/Solvent |
|---|---|---|---|
| 1-5 | 272 | 3.88 | A |
| 1-6 | 375 | 4.47 | A |
| 1-7 | 319 | 2.70 | B |
| 1-8 | 493 | 3.68 | A |
| 1 | 475 | 3.52 | A |
| 2-1 | 209 | 0.42 | A |
| 2-2 | 339 | 3.97 | A |
| 2-3 | 417 | 4.72 | A |
| 2-4 | 361 | 2.55 | B |
| 2-5 | 681 | 4.03 | B |
| 2 | 491 | 3.25 | B |
| 3-1 | 286 | 4.38 | A |
| 3-2 | 389 | 4.62 | A |
| 3-3 | 431 | 0.83 | C |
| 3-4 | 375 | 2.75 | A |
| 3-5 | 695 | 4.22 | B |
| 3 | 505 | 3.40 | B |
| 4-1 | 286 | 4.40 | A |
| 4-2 | 389 | 4.73 | A |
| 4-3 | 431 | 4.95 | A |
| 4-4 | 375 | 3.42 | A |
| 4-5 | 695 | 4.73 | B |
| 4 | 505 | 3.92 | B |
| 5-1 | 302 | 5.30 | A |
| 5-2 | 405 | 5.10 | A |
| 5-3 | 447 | 5.62 | A |
| 5-4 | 391 | 4.20 | A |
| 5-5 | 711 | 1.02 | C |
| 5 | 521 | 0.94 | C |
| 6-1 | 316 | 5.30 | A |
| 6-2 | 419 | 5.35 | A |
| 6-3 | 461 | 5.53 | A |
| 6-4 | 405 | 4.50 | B |
| 6-5 | 725 | 5.23 | B |
| 6 | 535 | 4.87 | A |
| 7-1 | 340 | 5.48 | A |
| 7-2 | 443 | 5.52 | A |
| 7-3 | 485 | 5.60 | A |
| 7-4 | 429 | 4.92 | B |
| 7-5 | 749 | 1.04 | C |
| 7 | 559 | 5.17 | A |
| 8-1 | 354 | 5.57 | A |
| 8-2 | 457 | 5.53 | A |
| 8-3 | 521[M + Na]$^+$ | 5.67 | A |
| 8-4 | 443 | 4.85 | B |
| 8-5 | 763 | 1.05 | C |
| 8 | 573 | 5.05 | A |
| 9-1 | 273 | 3.80 | A |
| 9-2 | 376 | 4.52 | A |
| 9-3 | 418 | 4.68 | A |
| 9-4 | 362 | 3.20 | B |
| 9-5 | 682 | 4.65 | A |
| 9 | 492 | 3.78 | B |
| 10-1 | 227 | 0.55 | C |
| 10-2 | 338 | 0.94 | C |
| 10-3 | 463[M + Na]$^+$ | 0.96 | C |
| 10-4 | 505[M + Na]$^+$ | 0.99 | C |
| 10-5 | 449[M + Na]$^+$ | 0.77 | C |
| 10-6 | 747 | 0.97 | C |
| 10 | 557 | 0.86 | C |
| 11-1 | 303 | 5.25 | A |
| 11-2 | 428[M + Na]$^+$ | 5.37 | A |
| 11-3 | 470[M + Na]$^+$ | 5.53 | A |
| 11-4 | 392 | 4.77 | A |
| 11-5 | 712 | 5.35 | B |
| 11 | 522 | 4.88 | B |
| 12-1 | 296 | 5.15 | A |
| 12-2 | 421[M + Na]$^+$ | 5.23 | A |
| 12-3 | 463[M + Na]$^+$ | 5.40 | A |
| 12-4 | 385 | 4.47 | B |
| 12-5 | 705 | 1.02 | u |
| 12 | 515 | 4.85 | B |
| 13-1 | 364 | 5.75 | A |
| 13-2 | 489[M + Na]$^+$ | 5.72 | A |
| 13-3 | 531[M + Na]$^+$ | 5.80 | A |
| 13-4 | 453 | 5.15 | B |
| 13-5 | 773 | 5.55 | B |
| 13 | 583 | 5.37 | B |
| 14-1 | 223 | 4.13 | A |
| 14-2 | 348[M + Na]$^+$ | 4.42 | A |
| 14-3 | 390[M + Na]$^+$ | 4.68 | A |
| 14-4 | 334[M + Na]$^+$ | 3.33 | A |
| 14-5 | 632 | 4.68 | B |
| 14 | 442 | 4.03 | A |
| 15-1 | 235 | 4.25 | A |
| 15-2 | 360[M + Na]$^+$ | 4.62 | A |
| 15-3 | 402[M + Na]$^+$ | 4.83 | A |
| 15-4 | 346[M + Na]$^+$ | 3.57 | A |
| 15-5 | 644 | 4.78 | B |
| 15 | 454 | 4.02 | B |
| 16-1 | 293 | 4.38 | A |
| 16-2 | 418[M + Na]$^+$ | 4.73 | A |
| 16-3 | 460[M + Na]$^+$ | 5.02 | A |
| 16-4 | 382 | 3.75 | B |
| 16-5 | 702 | 4.85 | B |
| 16 | 512 | 4.22 | A |
| 17-1 | 399[M + Na]$^+$ | 5.33 | A |
| 17-2 | 441[M + Na]$^+$ | 5.53 | B |
| 17-3 | 385[M + Na]$^+$ | 4.60 | B |
| 17-4 | 683 | 5.28 | B |
| 17 | 493 | 4.87 | B |
| 18-1 | 417[M + Na]$^+$ | 5.50 | A |
| 18-2 | 459[M + Na]$^+$ | 5.67 | A |
| 18-3 | 403[M + Na]$^+$ | 5.05 | B |
| 18-4 | 701 | 5.48 | B |
| 18 | 511 | 5.10 | B |
| 19-1 | 397[M + Na]$^+$ | 5.17 | A |
| 19-2 | 439[M + Na]$^+$ | 5.35 | A |
| 19-3 | 361 | 4.57 | B |
| 19-4 | 681 | 5.20 | B |
| 19 | 491 | 4.75 | A |
| 20-1 | 371[M + Na]$^+$ | 5.27 | A |

TABLE 2-continued

| EXAMPLE | LC/MS m/z [M + 1]+ | RT min | Method/ Solvent |
|---|---|---|---|
| 20-2 | 413[M + Na]+ | 5.50 | A |
| 20-3 | 335 | 4.45 | A |
| 20-4 | 655 | 5.25 | A |
| 20 | 466 | 4.85 | A |
| 21-2 | 367 | 4.68 | A |
| 21-3 | 409 | 4.97 | A |
| 21-4 | 353 | 3.58 | B |
| 21-5 | 673 | 4.83 | B |
| 21 | 483 | 4.25 | A |
| 22-1 | 266[M-18]+ | 1.05 | C |
| 22-2 | 457[M + Na]+ | 1.04 | C |
| 22-3 | 499[M + Na]+ | 1.08 | C |
| 22-4 | 443[M + Na]+ | 0.90 | C |
| 22-5 | 741 | 1.03 | C |
| 22 | 551 | 4.75 | B |
| 23-1 | 250[M + Na]+ | 4.78 | A |
| 23-2 | 379 | 4.88 | A |
| 23-3 | 463 | 5.45 | A |
| 23-4 | 407 | 4.53 | B |
| 23-5 | 727 | 5.28 | A |
| 23 | 537 | 4.85 | B |
| 24-1 | 421 | 5.18 | A |
| 24-2 | 365 | 3.93 | B |
| 24-3 | 685 | 5.02 | B |
| 24 | 495 | 4.38 | B |
| 25-1 | 256 | 4.47 | A |
| 25-2 | 429[M + Na]+ | 4.88, 5.00 | A |
| 25-3 | 513[M + Na]+ | 5.52 | A |
| 25-4 | 435 | 4.73 | B |
| 25-5 | 755 | 1.04 | C |
| 25 | 523 | 4.35 | B |
| 26-1 | 271 | 4.97 | A |
| 26-2 | 443[M + Na]+ | 5.22 | A |
| 26-3 | 485[M + Na]+ | 5.37 | A |
| 26-4 | 407 | 4.37 | A |
| 26-5 | 727 | 5.18 | A |
| 26 | 537 | 4.72 | B |
| 27-1 | 280 | 1.10 | C |
| 27-2 | 348 | 4.83 | B |
| 27-3 | 490[M + Na]+ | 1.26 | C |
| 27-4 | 462[M + Na]+ | 1.02 | C |
| 27-5 | 460[M + Na]+ | 1.15 | C |
| 27-6 | 245 | 0.54 | C |
| 27-7 | 682 | 1.00, 1.04 | C |
| 27-8 | 581 | 0.95, 0.97 | C |
| 27-9 | 594 | 0.77, 0.79 | C |
| 27-10 | 474 | 0.54, 0.58 | C |
| 27 | 474 | 3.05 | A |
| 28-1 | 204 | 4.52 | B |
| 28-2 | 305 | 3.93 | B |
| 28-3 | 323 | 3.65 | B |
| 28-4 | 665 | 3.88 | A |
| 28-5 | 605 | 3.77 | A |
| 28 | 485 | 3.03 | B |

Intermediate 1

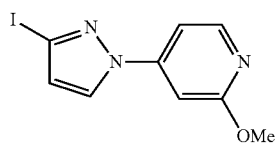 [SMILES: COc1cc(-n2ccc(I)n2)ccn1]

4-(3-Iodo-1H-pyrazol-1-yl)-2-methoxypyridine

To 3-iodo-1H-pyrazole (763 mg, 3.93 mmol) in DMSO (15 mL) at 0° C., was added sodium hydride (60% in mineral oil, 189 mg, 4.72 mmol). The reaction was warmed to 25° C. and stirred for 60 min before 4-fluoro-2-methoxypyridine (500 mg, 3.93 mmol) was added. The reaction mixture was stirred at 90° C. for 4.5 h before quenching by the addition of water. The reaction mixture was extracted with EtOAc. The combined organic extracts were dried over MgSO$_4$ and concentrated in vacuo. The crude mixture was purified by flash chromatography (ISCO Combiflash, 0-30% EtOAc in hexanes) to afford 4-(3-iodo-1H-pyrazol-1-yl)-2-methoxypyridine, as a white solid. LCMS calc.=301.97. found=302.02 (M+H)'.

Intermediate 2

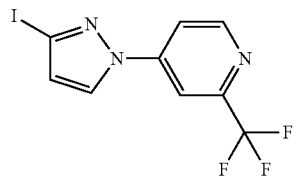

4-(3-Iodo-1H-pyrazol-1-yl)-2-(trifluoromethyl)pyridine

To a solution of 3-iodopyrazole (0.70 g, 3.61 mmol), in DMSO (18.0 mL) was added sodium hydride (60% disp. in oil, 0.173 g, 4.33 mmol), and the resulting mixture was stirred for 0.5 h before adding 4-fluoro-2-trifluoromethyl pyridine (0.596 g, 3.61 mmol). The reaction mixture was stirred at 90° C. for 3 h. The reaction was quenched by the addition of water and extracted with EtOAc. The combined organic extracts were washed with water and brine, dried over MgSO$_4$ and concentrated in vacuo. The crude mixture was purified by flash chromatography (ISCO, 40 g, 0-50% EtOAc in hexanes) to afford 4-(3-iodo-1H-pyrazol-1-yl)-2-(trifluoromethyl)pyridine, as a white solid. LCMS calc.=339.95. found=339.93 (M+H)+. $^1$H NMR (500 MHz, CDCl$_3$): δ 8.77 (d, J=5.3 Hz, 1H); 8.03 (d, J=3.8 Hz, 1H); 7.91 (d, J=2.6 Hz, 1H); 7.77 (d, J=5.4 Hz, 1H); 6.74 (d, J=2.5 Hz, 1H).

Intermediate 3

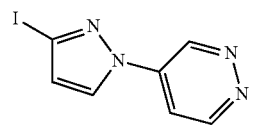 [SMILES: Ic1ccn(-c2ccnnc2)n1]

4-(3-Iodo-1H-pyrazol-1-yl)pyridazine

To the stirred solution of 4-iodopyridazine (1000 mg, 4.85 mmol) and 3-iodo-1H-pyrazole (951 mg, 4.90 mmol) in DMSO was added NaH (60% in oil, 233 mg, 5.83 mmol) in portion at 0° C. The mixture was stirred at room temperature for 30 min or until bubbling ceased, then warmed up to 50° C. and stirred at 50° C. overnight. The reaction mixture was cooled to room temperature, partitioned between EtOAc and water. The aqueous was extracted with EtOAc for three times. The organic phases were combined, dried over Na$_2$SO$_4$ and concentrated in vacuo to give the crude product. This was purified by flash chromatography (Isco Combi-Flash, 80 g Silica gel column, 0-100% EtOAc in hexanes) to afford 4-(3-iodo-1H-pyrazol-1-yl)pyridazine. LCMS calc.=272.96. found=272.96 (M+H)$^+$. $^1$H NMR (500 MHz, CDCl$_3$): δ 9.64 (d, J=3.0 Hz, 1H); 9.27 (d, J=6.0 Hz, 1H); 7.95 (d, J=2.5 Hz, 1H); 7.81 (dd, J=2.5 Hz, J=5.5 Hz, 1H); 6.79 (d, J=2.5 Hz, 1H).

Intermediate 4

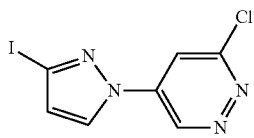 [SMILES: Clc1cc(-n2ccc(I)n2)cnn1]

3-Chloro-5-(3-iodo-1H-pyrazol-1-yl)pyridazine

To a solution of 3-iodopyrazole (500 mg, 2.58 mmol) and 3,5-dichloropyridazine (384 mg, 2.58 mmol) in anhydrous DMF (5 mL) at room temperature was added potassium tert-butoxide (289 mg, 2.58 mmol) in one portion. It was heated at 100° C. for 1 h. It was cooled to room temperature, diluted with EtOAc (50 mL), washed with satd aq. NaHCO$_3$ (10 mL) and water (100 mL). The aqueous layer was separated and extracted with EtOAc (3×50 mL). The combined organic layers were washed with water (100 mL), brine (100 mL), dried over Na$_2$SO$_4$, filtered and concentrated. The residue was purified by flash chromatography (ISCO Combiflash, Gold 40 g, 0-60% EtOAc in hexanes) to give 3-chloro-5-(3-iodo-1H-pyrazol-1-yl)pyridazine, as a white solid. LCMS calc.=306.92. found=306.96 (M+H)$^+$. $^1$H NMR (500 MHz, CHCl$_3$-d): δ 9.54 (d, J=2.3 Hz, 1H); 7.94 (d, J=2.7 Hz, 1H); 7.90 (d, J=2.3 Hz, 1H); 6.81 (d, J=2.7 Hz, 1H).

Intermediate 5

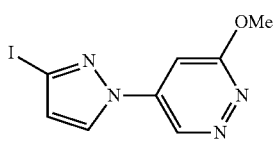 [SMILES: COc1cc(-n2ccc(I)n2)cnn1]

5-(3-Iodo-1H-pyrazol-1-yl)-3-methoxypyridazine

To a suspension of 3-chloro-5-(3-iodo-1H-pyrazol-1-yl)pyridazine (400 mg, 1.305 mmol) in MeOH (1 mL) was added triflic acid (300 µl, 3.38 mmol). The mixture was stirred at 50° C. for 6 h. It became a slight yellow solution. TEA (0.5 mL) was added and the mixture was concentrated and purified by flash chromatography (ISCO Combiflash, 40 g, 0-60% EtOAc in hexane) to give 5-(3-iodo-1H-pyrazol-1-yl)-3-methoxypyridazine. LCMS calc.=302.97. found=302.88 (M+H)$^+$.

Intermediate 6

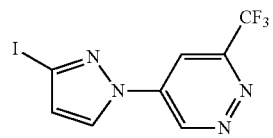 [SMILES: FC(F)(F)c1cc(-n2ccc(I)n2)cnn1]

5-(3-Iodo-1H-pyrazol-1-yl)-3-(trifluoromethyl)pyridazine

Step 6-1: 5-Chloro-3-iodopyridazine (intermediate 6-1)

A solution of pyridine (0.72 mL, 8.90 mmol), 5-chloro-pyridazin-3(2H)-one (1 g, 7.66 mmol) in MeCN (7 mL) was cooled to 0° C. and trifluoromethanesulfonic anhydride (2.4 g, 8.51 mmol) was added dropwise over 2 min. It was stirred for 30 min at room temperature, then charged with sodium iodide (5.74 g, 38.3 mmol) in one portion. Triflic acid (0.75 mL, 8.45 mmol) was added dropwise and the mixture was stirred for 1 h. It was quenched with water (10 mL) and 10 M NaOH (~1.5 mL) and 1 M NaOH (3 mL) were added to adjust pH to 10. 10% Aqueous Na$_2$CO$_3$ (10 mL), and saturated aqueous sodium thiosulfate (30 mL) were added and the mixture was extracted with EtOAc (2×50 mL). The combined organic layers were washed with brine, dried over Na$_2$SO$_4$, filtered and concentrated. The residue was purified twice by flash chromatography (ISCO Combiflash, 40 g, 0-40% EtOAc in hexanes, then Gold 40 g, 0-40% EtOAc in hexanes) to give 5-chloro-3-iodopyridazine. LCMS calc.=240.90. found=240.92 (M+H)$^+$.

Step 6-2: 5-Chloro-3-(trifluoromethyl)pyridazine (intermediate 6-2)

Cuprous iodide (0.77 g, 4.04 mmol) and potassium fluoride (0.24 g, 4.13 mmol) were thoroughly mixed and flame-heated under gentle shaking and at reduced pressure for 30 min until a greenish color appeared. 5-Chloro-3-iodopyridazine (0.88 g, 3.66 mmol), anhydrous DMF (2 mL), N-methyl-2-pyrrolidinone (2 mL) and (trifluoromethyl)trimethylsilane (0.57 g, 4.01 mmol) were added and the slurry was stirred vigorously for 16 h at room temperature. It was quenched with satd aq. NH$_4$Cl (20 mL) and EtOAc (20 mL). The mixture was filtered through Celite® (Fluka) diatomite which is diatomaceous earth and separated. The aqueous layer was extracted with EtOAc (2×30 mL). The combined organic layers were filtered and washed with satd aq. NaHCO$_3$ and brine, dried over Na$_2$SO$_4$, filtered and concentrated. The residue was purified by flash chromatography (ISCO Combiflash, Gold 40 g, 0-30% EtOAc in hexanes) to give 5-chloro-3-(trifluoromethyl)pyridazine. $^1$H NMR (500 MHz, CDCl$_3$): δ 9.41 (d, J=2.3 Hz, 1H); 7.90 (d, J=2.3 Hz, 1H).

Step 6-3: 5-(3-Iodo-1H-pyrazol-1-yl)-3-(trifluoromethyl)pyridazine

To 3-iodopyrazole (124 mg, 0.641 mmol) in DMF (2 mL) was added potassium tert-butoxide (53 mg, 0.472 mmol) at 0° C. The mixture was stirred at room temperature for 15 min. It was transferred into a solution of 5-chloro-3-(trifluoromethyl)pyridazine (78 mg, 0.427 mmol) in DMF (2 mL) at 0° C. It was warmed to room temperature, stirring for 30 min. It was diluted with EtOAc (20 mL), washed with water (3×20 mL), the combined aqueous layers were extracted with EtOAc (30 mL), the combined organic layers were washed with brine (30 mL), dried over $Na_2SO_4$, filtered and concentrated. The residue was purified by flash chromatography (ISCO Combiflash, 12 g, 0-100% EtOAc in hexanes) to give a mixture of 3-iodopyrazole and the desired product (1:2, 180 mg). It was dissolved in anhydrous $CH_2Cl_2$ (2 mL) and added a little bit of DMAP and of di-tert-butyl dicarbonate (~100 mg). It was stirred at room temperature for 10 min and purified by flash chromatography (ISCO Combiflash, 0-40% EtOAc in hexanes) to give 5-(3-iodo-1H-pyrazol-1-yl)-3-(trifluoromethyl)pyridazine, as a white solid. LCMS calc.=340.95. found=340.84 $(M+H)^+$. $^1H$ NMR (500 MHz, $CHCl_3$-d): δ 9.78 (d, J=2.5 Hz, 1H); 8.17 (d, J=2.5 Hz, 1H); 8.04 (d, J=2.7 Hz, 1H); 6.84 (d, J=2.7 Hz, 1H).

Intermediate 7

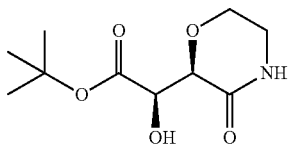 [SMILES: CC(C)(C)OC(=O)[C@H](O)[C@H]1OCCNC1=O]

(R)-tert-Butyl 2-hydroxy-2-((R)-3-oxomorpholin-2-yl)acetate

This compound was synthesized as in WO2010065717.

EXAMPLE 29

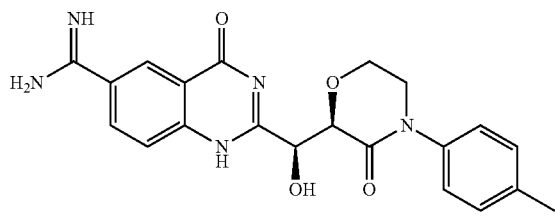 [SMILES: Cc1ccc(N2CCO[C@H]([C@@H](O)c3nc(=O)c4cc(C(=N)N)ccc4[nH]3)C2=O)cc1]

2-((S)-Hydroxy((R)-3-oxo-4-(p-tolyl)morpholin-2-yl)methyl)-4-oxo-1,4-dihydroquinazoline-6-carboximidamide Step 29-1: 5-Cyano-2-((R)-2-hydroxy-2-((R)-3-oxo-4-(p-tolyl)morpholin-2-yl)acetamido)benzamide (Compound 29-1)

Thionyl chloride (0.07 mL, 0.97 mmol) was added to imidazole (258 mg, 3.8 mmol) in $CH_2Cl_2$ (4.0 mL) at −10° C. The reaction mixture was stirred at room temperature for 10 min to form the imidazolium chloride salt which was removed by filtration. Additional thionyl chloride (0.07 mL, 0.97 mmol) was added to the filtrate. The reaction mixture was stirred at room temperature for 10 min to give a solution which was added immediately to 2-amino-5-cyanobenzamide (304 mg, 1.9 mmol) in $CH_2Cl_2$ (3.0 mL) at −40° C. After stirring at room temperature for 30 min, imidazolium chloride salt was removed by filtration to give a filtrate (intermediate A) which was used for the subsequent reaction. The mixture of (R)-2-hydroxy-2-((R)-3-oxo-4-(p-tolyl)morpholin-2-yl)acetic acid (100 mg, 0.38 mmol) and 1, 2, 4-triazole (39 mg, 0.57 mmol) in $CH_2Cl_2$ (3.0 mL) was stirred at room temperature until it became a clear solution. The solution was cooled to 0° C. and intermediate A above in $CH_2Cl_2$ solution was added. The reaction mixture was stirred at room temperature for 72 h. Solvent was evaporated under reduced pressure and the residue was diluted with EtOAc. The organic solution was washed with 2N HCl, saturated aqueous $NaHCO_3$ and brine solution, dried over anhydrous $Na_2SO_4$ and evaporated under reduced pressure. The product product was purified by flash chromatography (ISCO, 0-100% EtOAc/hexanes) to afford 5-cyano-2-((R)-2-hydroxy-2-((R)-3-oxo-4-(p-tolyl)morpholin-2-yl)acetamido)benzamide, as a colorless viscous liquid. LCMS calc.=409.15. found=409.2 $(M+H)^+$.

Step 29-2: 2-((S)-Hydroxy((R)-3-oxo-4-(p-tolyl)morpholin-2-yl)methyl)-4-oxo-1,4-dihydroquinazoline-6-carbonitrile (Compound 29-2)

A mixture of 5-cyano-2-((R)-2-hydroxy-2-((R)-3-oxo-4-(p-tolyl)morpholin-2-yl)acetamido)benzamide (5.0 mg, 0.012 mmol) and 1 N NaOH (0.1 mL, 0.1 mmol) in 1,4-dioxane (2.0 mL) was stirred at room temperature for 2 h. The reaction mixture was diluted with EtOAc, washed with 1 N HCl, water and brine solution, dried over $Na_2SO_4$ and evaporated under reduced pressure to afford 2-((S)-hydroxy((R)-3-oxo-4-(p-tolyl)morpholin-2-yl)methyl)-4-oxo-1,4-dihydroquinazoline-6-carbonitrile, as a colorless viscous liquid which was used for next step without further purification. LCMS calc.=391.14. found=391.2 $(M+H)^+$.

Step 29-3: Ethyl 2-((S)-hydroxy((R)-3-oxo-4-(p-tolyl)morpholin-2-yl)methyl)-4-oxo-1,4-dihydroquinazoline-6-carbimidate Acetyl chloride (3.0 mL) was added to EtOH (1.0 mL) dropwise at 0° C., followed by crude 2-((S)-hydroxy((R)-3-oxo-4-(p-tolyl)morpholin-2-yl)methyl)-4-oxo-1,4-dihydroquinazoline-6-carbonitrile (4.7 mg, 0.012 mmol) in EtOH (2.0 mL) dropwise. The reaction mixture was stirred at room temperature for 72 h. The solvent was evaporated under reduced pressure. The residue was treated with ammonium solution (7.0 N in MeOH, 5 mL). The reaction mixture was stirred overnight and purified by RP-HPLC to afford ethyl 2-((S)-hydroxy((R)-3-oxo-4-(p-tolyl)morpholin-2-yl)methyl)-4-oxo-1,4-dihydroquinazoline-6-carbimidate, as a colorless syrup. LCMS calc.=408.17. found=408.2 $(M+H)^+$.

EXAMPLE 30

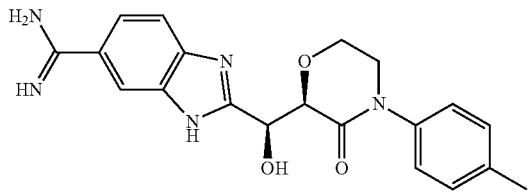 [SMILES: Cc1ccc(N2CCO[C@H]([C@@H](O)c3nc4ccc(C(=N)N)cc4[nH]3)C2=O)cc1]

2-((S)-Hydroxy((R)-3-oxo-4-(p-tolyl)morpholin-2-yl)methyl)-1H-benzo[d]imidazole-6-carboximidamide

Step 30-1: (R)-tert-Butyl 2-hydroxy-2-((R)-3-oxo-4-(p-tolyl)morpholin-2-yl)acetate (Compound 30-1)

To a stirred mixture of (R)-tert-butyl 2-hydroxy-2-((R)-3-oxomorpholin-2-yl)acetate (200 mg, 0.865 mmol), 1-iodo-4-methylbenzene (226 mg, 1.037 mmol), copper (I) iodide (16 mg, 0.084 mmol) and potassium phosphate (367 mg, 1.729 mmol) in DMF (5 mL) was added $N^1,N^2$-dimethylcyclohexane-1,2-diamine (0.027 mL, 0.171 mmol) at 25° C. The reaction was heated at 110° C. for 4 h under $N_2$. The reaction mixture was diluted with EtOAc, washed with ammonium hydroxide, water (×3) and brine, dried over $Na_2SO_4$ and concentrated in vacuo to yield the crude product. This was purified by reversed phase chromatography (0-100% 0.1% formic acid in MeCN/0.1% formic acid in water) to afford (R)-tert-butyl 2-hydroxy-2-((R)-3-oxo-4-(p-tolyl)morpholin-2-yl)acetate. LCMS calc.=344.15. found=344.2 $(M+Na)^+$.

Step 30-2: (R)-2-Hydroxy-2-((R)-3-oxo-4-(p-tolyl)morpholin-2-yl)acetic acid (Compound 30-2)

A solution of (R)-tert-butyl 2-hydroxy-2-((R)-3-oxo-4-(p-tolyl)morpholin-2-yl)acetate (87 mg, 0.271 mmol) in 20% TFA in $CH_2Cl_2$ was stirred at 25° C. for 1 h. The solvent was evaporated in vacuo to afford product (R)-2-hydroxy-2-((R)-3-oxo-4-(p-tolyl)morpholin-2-yl)acetic acid. LCMS calc.=266.10. found=266.2 $(M+H)^+$.

Step 30-3: (R)—N-(2-Amino-5-cyanophenyl)-2-hydroxy-2-((R)-3-oxo-4-(p-tolyl)morpholin-2-yl)acetamide (Compound 30-3)

A mixture of (R)-2-hydroxy-2-((R)-3-oxo-4-(p-tolyl)morpholin-2-yl)acetic acid (155 mg, 0.584 mmol), 3,4-diaminobenzonitrile (93 mg, 0.698 mmol), HATU (289 mg, 0.76 mmol) and N-ethyl-N-isopropylpropan-2-amine (0.312 mL, 1.791 mmol) in DMF (4 mL) was stirred at 25° C. overnight. The reaction mixture was diluted with EtOAc, washed with water (×3) and brine, dried over $Na_2SO_4$ and concentrated in vacuo. The crude product was purified by reversed phase chromatography (0-100% 0.1% formic acid in MeCN/0.1% formic acid in water) to afford (R)—N-(2-amino-5-cyanophenyl)-2-hydroxy-2-((R)-3-oxo-4-(p-tolyl)morpholin-2-yl)acetamide.

Step 30-4: 2-((S)-Hydroxy((R)-3-oxo-4-(p-tolyl)morpholin-2-yl)methyl)-1H-benzo[d]imidazole-6-carbonitrile (Compound 30-4)

A suspension of (R)—N-(2-amino-5-cyanophenyl)-2-hydroxy-2-((R)-3-oxo-4-(p-tolyl)morpholin-2-yl)acetamide (76 mg, 0.200 mmol) in HOAc (4 mL) was treated with microwave reaction condition at 120° C. for 20 min. The crude product was purified by reversed phase chromatography (0-100% 0.1% formic acid in MeCN/0.1% formic acid in water) to afford 2-((S)-hydroxy((R)-3-oxo-4-(p-tolyl)morpholin-2-yl)methyl)-1H-benzo[d]imidazole-6-carbonitrile. LCMS calc.=363.15. found=363.2 $(M+H)^+$. $^1$H-NMR (600 MHz, $CD_3OD$): 7.92 (br s, 1H); 7.64 (d, J=8.1 Hz, 1H); 7.48 (dd, J=8.4, 0.9 Hz, 1H); 7.13-7.25 (m, 4H); 5.63 (d, J=1.5 Hz, 1H); 4.82 (d, J=1.5 Hz, 1H); 4.10-4.23 (m, 1H); 3.97 (d, J=6.6 Hz, 2H); 3.48-3.61 (m, 1H); 2.33 (s, 3H).

Step 30-5: Ethyl 2-((S)-hydroxy((R)-3-oxo-4-(p-tolyl)morpholin-2-yl)methyl)-1H-benzo[d]imidazole-6-carbimidate (Compound 30-5)

A solution of 2-((S)-hydroxy((R)-3-oxo-4-(p-tolyl)morpholin-2-yl)methyl)-1H-benzo[d]imidazole-6-carbonitrile (32.2 mg, 0.089 mmol) in EtOH (3 mL) was cooled to 0° C. and acetyl chloride (2.424 mL, 34.1 mmol) was added dropwise. The reaction mixture was stirred at 25° C. for two days. Solvent was evaporated in vacuo to afford a crude product ethyl 2-((S)-hydroxy((R)-3-oxo-4-(p-tolyl)morpholin-2-yl)methyl)-1H-benzo[d]imidazole-6-carbimidate which was used in the next step without further purification.

Step 30-6: 2-((S)-Hydroxy((R)-3-oxo-4-(p-tolyl)morpholin-2-yl)methyl)-1H-benzo[d]imidazole-6-carboximidamide Ethyl 2-((S)-hydroxy((R)-3-oxo-4-(p-tolyl)morpholin-2-yl)methyl)-1H-benzo[d]imidazole-6-carbimidate was suspended in 7N $NH_3$ in MeOH (4 mL) and the reaction mixture was stirred at 25° C. overnight. Solvent was evaporated in vacuo. The crude product was purified by reversed phase chromatography (0-100% 0.1% formic acid in MeCN/0.1% formic acid in water) to afford 2-((S)-hydroxy((R)-3-oxo-4-(p-tolyl)morpholin-2-yl)methyl)-1H-benzo[d]imidazole-6-carboximidamide. LCMS calc.=380.17. found=380.2 $(M+H)^+$.

EXAMPLE 31

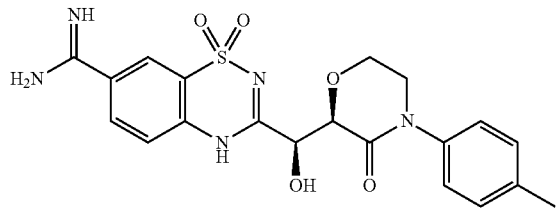 [SMILES: Cc1ccc(N2CCO[C@H]([C@@H](O)C3=NS(=O)(=O)c4cc(C(=N)N)ccc4N3)C2=O)cc1]

3-((S)-Hydroxy((R)-3-oxo-4-(p-tolyl)morpholin-2-yl)methyl)-4H-benzo[e][1,2,4]thiadiazine-7-carboximidamide 1,1-dioxide

Step 31-1: (R)—N-(4-Cyano-2-sulfamoylphenyl)-2-hydroxy-2-((R)-3-oxo-4-(p-tolyl)morpholin-2-yl)acetamide (Compound 31-1)

A suspension of 1H-imidazole (349 mg, 5.13 mmol) in $CH_2Cl_2$ (4 mL) was added to sulfurous dichloride (0.093 mL, 1.274 mmol) at −10° C. The reaction mixture was stirred at room temperature for 10 min. The reaction mixture was filtered and additional sulfurous dichloride (0.093 mL, 1.274 mmol) was added at −10° C. The reaction mixture was stirred at room temperature for 10 min and was added to a suspension of 2-amino-5-cyanobenzenesulfonamide (303 mg, 1.536 mmol) in CH$_2$Cl$_2$ (1 mL) at −40° C. The reaction mixture was stirred at room temperature for 30 min and filtered to yield a yellow solution-A. To (R)-2-hydroxy-2-((R)-3-oxo-4-(p-tolyl)morpholin-2-yl)acetic acid (136 mg, 0.513 mmol) was added 1H-1,2,3-triazole (53 mg, 0.767 mmol) in CH$_2$Cl$_2$. The reaction mixture was stirred at room temperature for 20 min and was cooled to 0° C. Solution-A was added and the reaction mixture was stirred at 25° C. overnight. Solvent was evaporated in vacuo and the crude product was purified by reversed phase chromatography (0-100% 0.1% formic acid in MeCN/0.1% formic acid in water) to afford (R)—N-(4-cyano-2-sulfamoylphenyl)-2-hydroxy-2-((R)-3-oxo-4-(p-tolyl)morpholin-2-yl)acetamide. LCMS calc.=445.12. found=445.2 (M+H)$^+$.

Step 31-2: 3-((S)-Hydroxy((R)-3-oxo-4-(p-tolyl)morpholin-2-yl)methyl)-4H-benzo[e][1,2,4]thiadiazine-7-carbonitrile 1,1-dioxide (Compound 31-2)

(R)—N-(4-Cyano-2-sulfamoylphenyl)-2-hydroxy-2-((R)-3-oxo-4-(p-tolyl)morpholin-2-yl)acetamide (86.4 mg, 0.194 mmol) was dissolved in concentrated ammonium hydroxide (8 mL) and the reaction mixture was heated to reflux under N$_2$ for two days. Solvent was evaporated in vacuo and the crude product was purified by reversed phase chromatography (0-100% 0.1% formic acid in MeCN/0.1% formic acid in water) to afford 3-((S)-hydroxy((R)-3-oxo-4-(p-tolyl)morpholin-2-yl)methyl)-4H-benzo[e][1,2,4]thiadiazine-7-carbonitrile 1,1-dioxide. LCMS calc.=427.11. found=427.2 (M+H)$^+$.

Step 31-3: Ethyl 3-((S)-hydroxy((R)-3-oxo-4-(p-tolyl)morpholin-2-yl)methyl)-4H-benzo[e][1,2,4]thiadiazine-7-carbimidate 1,1-dioxide (Compound 31-3)

A solution of 3-((S)-hydroxy((R)-3-oxo-4-(p-tolyl)morpholin-2-yl)methyl)-4H-benzo[e][1,2,4]thiadiazine-7-carbonitrile 1,1-dioxide (8.5 mg, 0.020 mmol) in EtOH (2 mL) was cooled to 0° C. Acetyl chloride (1.62 mL, 22.73 mmol) was added dropwise. The reaction mixture was stirred at 25° C. overnight. Solvent was evaporated in vacuo to afford a crude product ethyl 3-((S)-hydroxy((R)-3-oxo-4-(p-tolyl)morpholin-2-yl)methyl)-4H-benzo[e][1,2,4]thiadiazine-7-carbimidate 1,1-dioxide which was used in the next step without further purification.

Step 31-4: 3-Oxo-4-(p-tolyl)morpholin-2-yl)methyl)-4H-benzo[e][1,2,4]thiadiazine-7-carboximidamide 1,1-dioxide (EXAMPLE 31)

Ethyl 3-((S)-hydroxy((R)-3-oxo-4-(p-tolyl)morpholin-2-yl)methyl)-4H-benzo[e][1,2,4]thiadiazine-7-carbimidate 1,1-dioxide was suspended in 7N NH$_3$ in MeOH (4 mL) and the reaction mixture was stirred at 25° C. overnight. Solvent was evaporated in vacuo and the crude product was purified by reversed phase chromatography (0-100% 0.1% formic acid in MeCN/0.1% formic acid in water) to afford 3-oxo-4-(p-tolyl)morpholin-2-yl)methyl)-4H-benzo[e][1,2,4]thiadiazine-7-carboximidamide 1,1-dioxide. LCMS calc.=444.13. found=444.2 (M+H)$^+$.

Intermediate 8

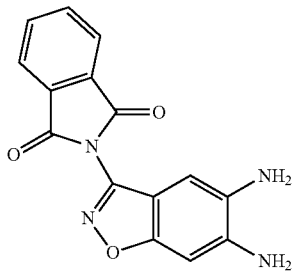 [SMILES: Nc1cc2onc(N3C(=O)c4ccccc4C3=O)c2cc1N]

2-(5,6-Diaminobenzo[d]isoxazol-3-yl)isoindoline-1,3-dione

Step 8-1: 4-Amino-2-fluoro-5-nitrobenzonitrile (intermediate 8-1)

2,4-Difluoro-5-nitrobenzonitrile (10 g, 54.3 mmol) and EtOH (14 mL) were stirred at room temperature. To this mixture was added ammonium hydroxide (45.3 mL, 326 mmol) slowly to give a precipitate. The reaction was exothermic and was boiling a little during the addition of 1st 10 mL NH$_4$OH. The reaction mixture was filtered after 2.5 h. The cake was air-dried for 1 h then transferred to a vial and placed under high vacuum overnight to afford 4-amino-2-fluoro-5-nitrobenzonitrile, as a free flowing yellow solid. LCMS calc.=181.03. found=181.96 (M+H)$^+$.

Step 8-2: tert-Butyl (4-cyano-5-fluoro-2-nitrophenyl)carbamate (intermediate 8-2)

To solution of 4-amino-2-fluoro-5-nitrobenzonitrile (2.5 g, 13.80 mmol) in THF (20 mL), was added sodium hydride (0.552 g, 13.80 mmol). The resulting dark colored mixture was stirred for 30 min followed by addition of di-tert-butyl dicarbonate (3.01 g, 13.80 mmol) and 4-dimethylaminopyridine (0.253 g, 2.070 mmol). The reaction mixture was stirred for 2 h then quenched carefully with satd. aq. NH$_4$Cl and extracted with EtOAc. The combined organic layers were dried (Na$_2$SO$_4$), filtered and concentrated in vacuo. The pot residue was purified by flash chromatography (SiO$_2$, 330 g cartridge, EtOAc/hexanes) to afford tert-butyl (4-cyano-5-fluoro-2-nitrophenyl)carbamate, as a light yellow solid. $^1$H NMR (500 MHz, DMSO-d$_6$): δ 10.11 (s, 1H); 8.73 (d, J=6.6 Hz, 1H); 7.90 (d, J=11.5 Hz, 1H); 1.47 (s, 9H).

Step 8-3: tert-Butyl (3-amino-5-nitrobenzo[d]isoxazol-6-yl)carbamate (intermediate 8-3)

tert-Butyl (4-cyano-5-fluoro-2-nitrophenyl)carbamate (1.2013 g, 4.27 mmol), acetohydroxamic acid (0.641 g, 8.54 mmol), potassium carbonate (2.361 g, 17.09 mmol), DMF (32.4 mL) and water (3.2 mL) were stirred at room temperature for 2 h. The crude was worked up with water/EtOAc. The combined extracts were dried over Na$_2$SO$_4$, filtered and evaporated in vacuo. The resulting residue was purified by flash chromatography (SiO$_2$, 100 g cartridge, EtOAc/hexanes (0-60%)) to afford tert-butyl (3-amino-5-nitrobenzo[d]isoxazol-6-yl)carbamate, as a yellow solid. $^1$H NMR (500 MHz, DMSO-d$_6$): δ 9.80 (s, 1H); 8.73 (s, 1H); 7.80 (s, 1H); 6.73 (s, 2H); 1.46 (s, 9H).

Step 8-4: tert-Butyl (3-(1,3-dioxoisoindolin-2-yl)-5-nitrobenzo[d]isoxazol-6-yl)carbamate (intermediate 8-4)

To a solution of tert-butyl (3-amino-5-nitrobenzo[d]isoxazol-6-yl)carbamate (250 mg, 0.850 mmol) in $CH_2Cl_2$ (17.0 mL) at room temperature was added phthaloyl dichloride (0.147 mL, 1.019 mmol) followed by triethylamine (0.284 mL, 2.039 mmol). The mixture was stirred at room temperature overnight. The crude was worked up with water/$CH_2Cl_2$. The combined extracts were dried over $Na_2SO_4$, filtered and evaporated in vacuo. The pot residue was purified by flash chromatography ($SiO_2$, 80 g cartridge, EtOAc/hexanes (0-60%)) to afford tert-butyl (3-(1,3-dioxoisoindolin-2-yl)-5-nitrobenzo[d]isoxazol-6-yl)carbamate, as a yellow solid. LCMS calc.=425.11. found=424.84 $(M+H)^+$.

Step 8-5: tert-Butyl (5-amino-3-(1,3-dioxoisoindolin-2-yl)benzo[d]isoxazol-6-yl)carbamate (intermediate 8-5)

tert-Butyl (3-(1,3-dioxoisoindolin-2-yl)-5-nitrobenzo[d]isoxazol-6-yl)carbamate (230.6 mg, 0.543 mmol), stannous chloride (412 mg, 2.174 mmol) and DMF (8.4 mL) were stirred at room temperature overnight. The crude was worked up with water/EtOAc. The combined extracts were dried over $Na_2SO_4$, filtered and evaporated in vacuo. The resulting crude mixture was purified by flash chromatography ($SiO_2$, silica 80 g cartridge, EtOAc/hexanes) to afford tert-butyl (5-amino-3-(1,3-dioxoisoindolin-2-yl)benzo[d]isoxazol-6-yl)carbamate, as a light yellow glass. LCMS calc.=395.13. found=394.93 $(M+H)'$.

Step 8-6: 2-(5,6-Diaminobenzo[d]isoxazol-3-yl)isoindoline-1,3-dione tert-Butyl (5-amino-3-(1,3-dioxoisoindolin-2-yl)benzo[d]isoxazol-6-yl)carbamate (132 mg, 0.335 mmol), HCl (0.50 mL of a 4 M solution in 1,4-dioxane, 2.00 mmol) and $CH_2Cl_2$ (3 mL) were stirred at room temperature for 2 h. Volatiles were removed from the crude in vacuo. The pot residue was taken up by EtOAc and washed with sats aq. $NaHCO_3$. The combined extracts were dried over $Na_2SO_4$, filtered and evaporated in vacuo to afford 2-(5,6-diaminobenzo[d]isoxazol-3-yl)isoindoline-1,3-dione, as a foam. LCMS calc.=295.08. found=294.90 $(M+H)^+$.

EXAMPLE 32

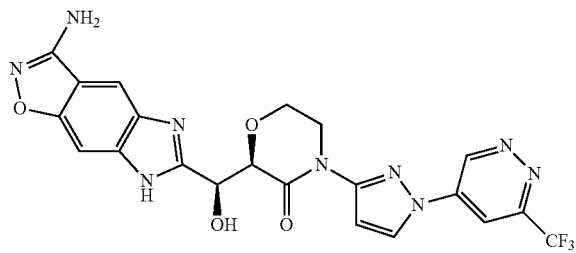 [SMILES: Nc1noc2cc3[nH]c([C@H](O)[C@H]4OCCN(c5ccn(-c6cnnc(C(F)(F)F)c6)n5)C4=O)nc3cc12]

(R)-2-((S)-(3-Amino-7H-imidazo[4',5':4,5]benzo[1,2-d]isoxazol-6-yl)(hydroxy)methyl)-4-(1-(6-(trifluoromethyl)pyridazin-4-yl)-1H-pyrazol-3-yl)morpholin-3-one Step 32-1: (R)-tert-Butyl 2-hydroxy-2-((R)-3-oxo-4-(1-(6-(trifluoromethyl)pyridazin-4-yl)-1H-pyrazol-3-yl)morpholin-2-yl)acetate (Compound 32-1)

(R)-tert-Butyl 2-hydroxy-2-((R)-3-oxomorpholin-2-yl)acetate (110 mg, 0.476 mmol), 5-(3-iodo-1H-pyrazol-1-yl)-3-(trifluoromethyl)pyridazine (162 mg, 0.476 mmol), potassium phosphate (0.240 mL, 1.189 mmol), trans-N,N'-dimethylcyclohexane-1,2-diamine (0.038 mL, 0.238 mmol), copper(I) iodide (45.3 mg, 0.238 mmol) and 1,4-dioxane (7 mL) were sealed in a reaction vessel. $N_2$ was bubbled through the mixture for 2 min then the vessel was sealed and heated at 80° C. for 4 h. The reaction crude was filtered into a stirred satd aq.$NH_4Cl$/ice mixture. The resulting mixture was partitioned between satd aq. $NH_4Cl$ and EtOAc. The combined extracts were dried over $Na_2SO_4$, filtered and evaporated in vacuo. The resulting crude mixture was purified by preparative HPLC (reversed phase, YMC-Pack Pro C-18, 100×20 mm, MeCN/water+0.05% HCOOH (10% to 100% organic in 10 min, hold 100% for 2 min, 20 mL/min)) to afford a light tan solid. This solid was again purified by preparative HPLC (reversed phase, YMC-Pack Pro C-18, 100×20 mm, MeCN/water+0.05% HCOOH (0% to 70% organic in 10 min, hold 100% for 2 min, 20 mL/min)) to afford a light tan solid. This was further purified by flash chromatography ($SiO_2$, 25 g cartridge, EtOAc/hexanes) to afford (R)-tert-butyl 2-hydroxy-2-((R)-3-oxo-4-(1-(6-(trifluoromethyl)pyridazin-4-yl)-1H-pyrazol-3-yl)morpholin-2-yl)acetate, as a white solid. LCMS calc.=444.15. found=443.89 $(M+H)^+$.

Step 32-2: (R)-2-Hydroxy-2-((R)-3-oxo-4-(1-(6-(trifluoromethyl)pyridazin-4-yl)-1H-pyrazol-3-yl)morpholin-2-yl)acetic acid hydrochloride (Compound 32-2)

(R)-tert-Butyl 2-hydroxy-2-((R)-3-oxo-4-(1-(6-(trifluoromethyl)pyridazin-4-yl)-1H-pyrazol-3-yl)morpholin-2-yl)acetate (40.7 mg, 0.092 mmol), trifluoroacetic acid (10 mg, 0.092 mmol) and $CH_2Cl_2$ (2 mL) were stirred at room temperature for 2 h. Volatiles were removed under reduced pressure. The pot residue was stirred in hydrochloric acid (0.023 mL of a 4 M solution in 1,4-dioxane, 0.092 mmol) at room temperature for 1 h. Volatiles were removed in vacuo. The remaining volatiles in the resulting yellow oil was chased with toluene (3×5 mL) and evaporated in vacuo to afford (R)-2-hydroxy-2-((R)-3-oxo-4-(1-(6-(trifluoromethyl)pyridazin-4-yl)-1H-pyrazol-3-yl)morpholin-2-yl)acetic acid hydrochloride, as a yellow glass. LCMS calc.=388.09. found=387.92 $(M+H)^+$.

Step 32-3: (R)-2-((S)-(3-Amino-7H-imidazo[4',5':4,5]benzo[1,2-d]isoxazol-6-yl)(hydroxy)methyl)-4-(1-(6-(trifluoromethyl)pyridazin-4-yl)-1H-pyrazol-3-yl)morpholin-3-one (R)-2-Hydroxy-2-((R)-3-oxo-4-(1-(6-(trifluoromethyl)pyridazin-4-yl)-1H-pyrazol-3-yl)morpholin-2-yl)acetic acid hydrochloride, 1-hydroxy-7-azabenzotriazole (19.3 mg, 0.142 mmol), 1-(3-dimethylaminopropyl)-3-ethylcarbodiimide hydrochloride (27.1 mg, 0.142 mmol) and 2-(5,6-diaminobenzo[d]isoxazol-3-yl)isoindoline-1,3-dione (20.8 mg, 0.071 mmol) were stirred in NMP (2 mL) at room temperature overnight. The reaction crude was purified by preparative HPLC (reversed phase, YMC-Pack Pro C-18, 100×20 mm, MeCN/water+0.1% formic acid (10% to 85% organic in 10 min, then to 100% in 2 min, 20 mL/min)) to afford a light tan solid. This solid was stirred in acetic acid (3 mL) at 60° C. for 3 h. Volatiles were removed under reduced pressure. The pot residue was worked up with aqueous sodium hydrogen carbonate/EtOAc. The combined extracts were dried over $Na_2SO_4$, filtered and evaporated in vacuo to afford a white solid. This solid was dissolved in $CH_2Cl_2$ (2 mL) and MeOH (2 mL). To this mixture was added hydrazine (0.033 mL, 1.062 mmol) and stirred at room temperature for 2 h. Volatiles were removed under reduced pressure. The resulting pot residue was dissolved in MeCN, filtered and purified by preparative HPLC (reversed phase, YMC-Pack Pro C-18, 100×20 mm, MeCN/water+ 0.1% formic acid (10% to 80% organic in 10 min, then to 100% in 2 min, 20 mL/min)) to afford a light yellow solid of 9.2 mg. This solid was further purified by preparative HPLC (reversed phase, YMC-Pack ODS C-18, 100×20 mm, MeCN/water (0% to 30% organic in 25 min, then to 100% in 5 min, 20 mL/min)) to afford (R)-2-((S)-(3-amino-7H-imidazo[4',5':4,5]benzo[1,2d]isoxazol-6-yl)(hydroxy)methyl)-4-(1-(6-(trifluoromethyl)pyridazin-4-yl)-1H-pyrazol-3-yl)morpholin-3-one, as a white solid. LCMS calc.=516.14. found=515.84 (M+H)$^+$. $^1$H NMR (500 MHz, CD$_3$OD): δ 9.95 (s, 1H); 8.66 (s, 1H); 8.39 (s, 1H); 7.90 (s, 1H); 7.42 (s, 1H); 7.38 (s, 1H); 5.70 (s, 1H); 4.92-4.85 (m, 1H); 4.35-4.26 (m, 1H); 4.26-4.17 (m, 1H); 4.16 (s, 1H); 4.00 (s, 1H).

The following compounds (Table 3) were synthesized using methods analogous to those described for EXAMPLE 32 from commercially available materials or intermediates whose syntheses are described above.

TABLE 3

| Example | | LCMS (M + H)$^+$ | Calc. (M + H)$^+$ |
|---|---|---|---|
| 33 | 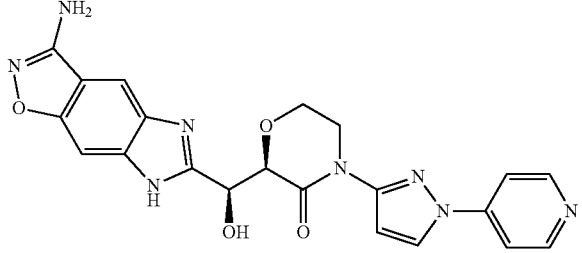<br>(2R)-2-[(S)-(3-amino-7H-imidazo[4,5-f][1,2]benzisoxazol-6-yl)(hydroxy)methyl]-4-(1-pyridin-4-yl-1H-pyrazol-3-yl)morpholin-3-one | 447.11 | 447.15 |
| 34 | 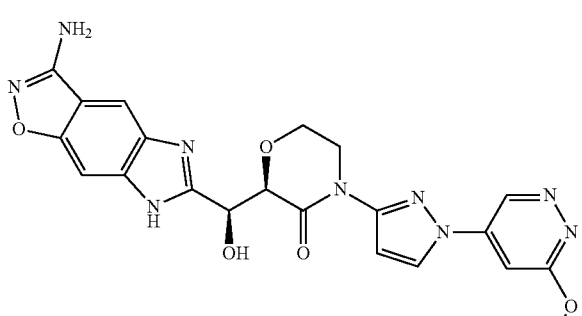<br>(2R)-2-[(S)-(3-amino-7H-imidazo[4,5-f][1,2]benzisoxazol-6-yl)(hydroxy)methyl]-4-[1-(6-methoxypyridazin-4-yl)-1H-pyrazol-3-yl]morpholin-3-one | 477.83 | 478.15 |

EXAMPLE 35

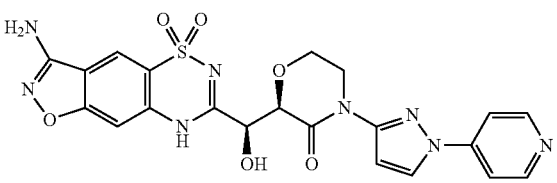 [SMILES: Nc1noc2cc3c(cc12)S(=O)(=O)N=C([C@H](O)[C@H]1OCCN(c2ccn(-c4ccncc4)n2)C1=O)N3]

(R)-2-((S)-(8-Amino-1,1-dioxido-4H-isoxazolo[4,5':4,5]benzo[1,2-e][1,2,4]thiadiazin-3-yl)(hydroxy)methyl)-4-(1-(pyridin-4-yl)-1H-pyrazol-3-yl)morpholin-3-one Step 35-1: 6-Amino-3-(1,3-dioxoisoindolin-2-yl)benzo[d]isoxazole-5-sulfonamide (Compound 35-1)

To 2-(6-aminobenzo[d]isoxazol-3-yl)isoindoline-1,3-dione (1 g, 3.58 mmol) was added sulfurochloridic acid (12.52 g, 107 mmol) portionwise at 0° C. The resulting suspension was heated at 120° C. under $N_2$ for 1 h. The mixture was cooled to room temperature and poured into ice. The cold mixture was extracted with EtOAc (100 mL×3). The organic layer was collected and dried over anhydrous $Na_2SO_4$, and concentrated to afford 6-amino-3-(1,3-dioxoisoindolin-2-yl) benzo[d]isoxazole-5-sulfonyl chloride intermediate, as a solid. The crude solid was suspended in 1,4-dioxane (20 mL) and $NH_4OH$ (2.5 mL) was added dropwise over 30 min. The resulting mixture was stirred at room temperature for 1 h. The solvent was removed in vacuo to give the crude product. This was purified by HPLC (Gilson, C18, reverse phase column, 20% 0.1% TFA in MeCN in 0.1% TFA in water to 85% 0.1% TFA in MeCN in 0.1% TFA in water) to afford 6-amino-3-(1,3-dioxoisoindolin-2-yl)benzo[d]isoxazole-5-sulfonamide. LCMS calc.=359.05. found=358.97 $(M+H)^+$. $^1$H NMR (500 MHz, DMSO-$d_6$): δ 8.19 (s, 1H); 8.01 (m, 2H); 7.97 (m, 2H); 7.41 (br s, 2H); 6.98 (s, 1H).

Step 35-2: (R)-2-((3-(1,3-Dioxoisoindolin-2-yl)-5-sulfamoylbenzo[d]isoxazol-6-yl)amino)-2-oxo-1-((R)-3-oxo-4-(1-(pyridin-4-yl)-1H-pyrazol-3-yl)morpholin-2-yl)ethyl acetate (Compound 35-2)

To a solution of (R)-2-acetoxy-2-((R)-3-oxo-4-(1-(pyridin-4-yl)-1H-pyrazol-3-yl)morpholin-2-yl)acetic acid (60 mg, 0.167 mmol) in DMF (0.5 mL) was added 6-amino-3-(1,3-dioxoisoindolin-2-yl)benzo[d]isoxazole-5-sulfonamide (59.7 mg, 0.167 mmol), HBTU (63.3 mg, 0.167 mmol), and DIEA (64.0 uL, 0.366 mmol). The mixture was stirred at room temperature overnight. The mixture was diluted with water and extracted with EtOAc (10 mL×3). The organic layer was collected, dried over anhydrous $Na_2SO_4$, and concentrated to afford the crude product This was purified by HPLC (Gilson, C18, reverse phase column, 20% 0.1% TFA in MeCN in 0.1% TFA in water to 100% 0.1% TFA in MeCN) to afford (R)-2-((3-(1,3-dioxoisoindolin-2-yl)-5-sulfamoylbenzo[d]isoxazol-6-yl)amino)-2-oxo-1-((R)-3-oxo-4-(1-(pyridin-4-yl)-1H-pyrazol-3-yl)morpholin-2-yl)ethyl acetate. LCMS calc.=701.14. found=700.87 $(M+H)'$.

Step 35-3: (S)-(8-(1,3-Dioxoisoindolin-2-yl)-1,1-dioxido-4H-isoxazolo[4',5':4,5]benzo[1,2-e][1,2,4]thiadiazin-3-yl)((R)-3-oxo-4-(1-(pyridin-4-yl)-1H-pyrazol-3-yl)morpholin-2-yl)methyl acetate (Compound 35-3)

(R)-2-((3-(1,3-dioxoisoindolin-2-yl)-5-sulfamoylbenzo[d]isoxazol-6-yl)amino)-2-oxo-1-((R)-3-oxo-4-(1-(pyridin-4-yl)-1H-pyrazol-3-yl)morpholin-2-yl)ethyl acetate (20 mg, 0.029 mmol) was in 4.0 M HCl in 1,4-dioxane (0.5 mL). The resulting mixture was stirred at 90° C. for 30 min. The solvent was removed in vacuo to afford crude product This was purified by HPLC (Varian, C18, reverse phase column, 30% 0.5% HCOOH in MeCN in 0.5% HCOOH in water to 100% 0.5% HCOOH in MeCN) to afford (S)-(8-(1,3-dioxoisoindolin-2-yl)-1,1-dioxido-4H-isoxazolo[4',5':4,5]benzo[1,2-e][1,2,4]thiadiazin-3-yl)((R)-3-oxo-4-(1-(pyridin-4-yl)-1H-pyrazol-3-yl)morpholin-2-yl)methyl acetate. LCMS calc.=683.13. found=682.89 $(M+H)^+$.

Step 35-4: (R)-2-((S)-(8-Amino-1,1-dioxido-4H-isoxazolo[4',5':4,5]benzo[1,2-e][1,2,4]thiadiazin-3-yl)(hydroxy)methyl)-4-(1-(pyridin-4-yl)-1H-pyrazol-3-yl)morpholin-3-one To a solution of (S)-(8-(1,3-dioxoisoindolin-2-yl)-1,1-dioxido-4H-isoxazolo[4',5':4,5]benzo[1,2-e][1,2,4]thiadiazin-3-yl)((R)-3-oxo-4-(1-(pyridin-4-yl)-1H-pyrazol-3-yl)morpholin-2-yl)methyl acetate (8 mg, 0.012 mmol) in 1,4-dioxane (0.4 mL) was added one drop of hyrazine. The resulting mixture was stirred at 50° C. for 10 min. The solvent was removed in vacuo to give the crude product. This was purified by HPLC (Varian, C18, reverse phase column, 20% 0.5% HCOOH in MeCN in 0.5% HCOOH in water to 60% 0.5% HCOOH in MeCN in 0.5% HCOOH in water) to Example 35. LCMS calc.=511.11. found=510.95 $(M+H)^+$. $^1$H NMR (500 MHz, $CD_3OD$): δ 8.6 (d, 2H); 8.41 (s, 1H); 8.40 (d, 1H); 7.83 (d, 2H); 7.61 (s, 1H); 7.22 (d, 1H). 5.19 (d, 1H); 4.61 (br s, 1H); 4.3 (m, 1H); 4.21 (m, 1H); 4.15 (m, 1H); 4.01 (m, 1H).

The following compounds (Table 4) were synthesized using methods analogous to those described for EXAMPLE 35 from commercially available materials or intermediates whose syntheses are described above.

TABLE 4

| Example | | LCMS (M + H)$^+$ | Calc. (M + H)$^+$ |
|---|---|---|---|
| 36 | (2R)-2-[(S)-(8-amino-1,1-dioxido-4H-isoxazolo[5,4-g][1,2,4]benzothiadiazin-3-yl)(hydroxy)methyl]-4-[6-(trifluoromethyl)pyridin-2-yl]morpholin-3-one | 512.88 | 513.07 |

EXAMPLE 37

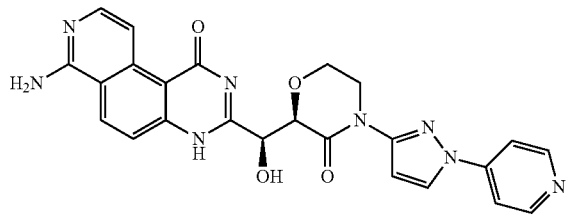 [SMILES: Nc1nccc2c1ccc1[nH]c([C@H](O)[C@H]3OCCN(c4ccn(-c5ccncc5)n4)C3=O)nc(=O)c12]

(R)-2-((S)-(7-Amino-1-oxo-1,4-dihydropyrido[4,3-f]
quinazolin-3-yl)(hydroxy)methyl)-4-(1-(pyridin-4-
yl)-1H-pyrazol-3-yl)morpholin-3-one

Step 37-1: 6-Amino-5-iodo-1-[bis(tert-butoxycarbonyl)amino]isoquinoline (Compound 37-1)

To a solution of 6-amino-1-[bis(tert-butoxycarbonyl)amino]isoquinoline (1.8 g, 5.01 mmol) in anhydrous $CH_2Cl_2$ (20 mL) was added N-iodosuccinimide (1.239 g, 5.51 mmol) at 25° C. The mixture was stirred at 25° C. for 2 h and then quenched with $NaHCO_3$ solution, diluted with $CH_2Cl_2$ (100 mL). The resulting mixture was stirred for 20 min and the layers were separated. The organic layer was washed with brine, dried over $Na_2SO_4$, filtered and evaporated. The resulting red solid was dissolved in EtOH (80 mL). Water (300 mL) was added to the EtOH solution and a yellow precipitate was formed. The mixture was stirred for 20 min and then filtered. The filter cake was washed with water and dried by air flow to give 6-amino-5-iodo-1-[bis(tert-butoxycarbonyl)amino]isoquinoline, as a yellow solid. LCMS calc.=486.09. found=486.1 $(M+H)^+$. $^1H$ NMR (500 MHz, $CDCl_3$): δ 8.39 (d, J=6.0 Hz, 1H); 7.77 (d, J=9.5 Hz, 1H); 7.72 (d, J=6.0 Hz, 1H); 7.08 (d, J=9.0 Hz, 1H); 4.83 (brs, 2H); 1.35 (s, 18H).

Step 37-2: Phenyl 6-amino-1-[bis(tert-butoxycarbonyl)amino]isoquinoline-5-carboxylate (Compound 37-2)

A mixture of Xantphos (119 mg, 0.206 mmol), $PdOAc_2$ (23.1 mg, 0.103 mmol), 6-amino-5-iodo-1-[bis(tert-butoxycarbonyl)amino]isoquinoline (500 mg, 1.030 mmol), phenol (194 mg, 2.061 mmol) was flushed with $N_2$ three times. DMF (8 mL) and triethylamine (0.431 mL, 3.09 mmol) were added. The mixture was bubbled with CO for 5 min and then stirred under 1 atm CO using a balloon. Then the mixture was stirred at 75° C. overnight under 1 atm CO using a balloon. The reaction mixture was then cooled to room temperature, poured into aq. $NH_4Cl$ solution and extracted with EtOAc (180 mL). The organic layer was dried over $Na_2SO_4$, filtered and evaporated. The residue was purified by flash chromatography (Isco Combiflash Rf, RediSep Silica 40 g, 0-100% EtOAc in hexanes) to afford phenyl 6-amino-1-[bis(tert-butoxycarbonyl)amino]isoquinoline-5-carboxylate. LCMS calc.=480.21. found=480.10 $(M+H)^+$.

Step 37-3: 6-Amino-1-[bis(tert-butoxycarbonyl)amino]isoquinoline-5-carboxamide (Compound 37-3)

Phenyl 6-amino-1-[bis(tert-butoxycarbonyl)amino]isoquinoline-5-carboxylate (380 mg, 0.792 mmol), concentrated ammonium hydroxide solution (8 mL, 28% wt, 57.5 mmol) and 1,4-dioxane (12 mL) were added to a microwave tube. The tube was sealed and stirred at 50° C. overnight. The reaction mixture was cooled to room temperature, diluted with brine and extracted with EtOAc (3×20 mL). The combined organic layers were dried over $Na_2SO_4$, filtered and evaporated. The residue was treated with a mixture of $CH_2Cl_2$, EtOAc and hexane, and the resulting suspension was filtered and the filter cake was dried by air-flow to afford 6-amino-1-[bis(tert-butoxycarbonyl)amino]isoquinoline-5-carboxamide, as pale yellow solid. LCMS calc.=403.19. found=403.2 (M+H)'.

Step 37-4: (R)-2-((5-Carbamoyl-[bis(tert-butoxycarbonyl)amino]isoquinolin-6-yl)amino)-2-oxo-1-((R)-3-oxo-4-(1-(pyridin-4-yl)-1H-pyrazol-3-yl)morpholin-2-yl)ethyl acetate (Compound 37-4)

A mixture of 6-amino-1-[bis(tert-butoxycarbonyl)amino]isoquinoline-5-carboxamide, (192 mg, 0.485 mmol), (R)-2-acetoxy-2-((R)-3-oxo-4-(1-(pyridin-4-yl)-1H-pyrazol-3-yl)morpholin-2-yl)acetic acid (192 mg, 0.485 mmol) and (1-cyano-2-ethoxy-2-oxoethylidenaminooxy)dimethylamino-morpholino-carbenium hexafluorophosphate (COMU, 303 mg, 0.708 mmol) was flushed with $N_2$ three times Anhydrous DMF (2 mL) was added, followed by DIEA (0.228 mL, 1.305 mmol). The reaction mixture was stirred at 50° C. overnight and another 1.5 eq of COMU was added. The resulting mixture was stirred at 50° C. overnight again. The reaction mixture was then cooled to room temperature, poured into aq. $NaHCO_3$ and NaCl solution and extracted with $CH_2Cl_2$ (2×80 mL). The combined organic layers were dried over $Na_2SO_4$, filtered and evaporated. The residue was purified by flash chromatography (Isco Combiflash Rf, RediSep Silica 40 g, 0-100% EtOAc in acetone) to afford (R)-2-((5-carbamoyl-[bis(tert-butoxycarbonyl)amino]isoquinolin-6-yl)amino)-2-oxo-1-((R)-3-oxo-4-(1-(pyridin-4-yl)-1H-pyrazol-3-yl)morpholin-2-yl)ethyl acetate. LCMS calc.=745.3. found=745.4 $(M+H)^+$.

Step 37-5: (R)-2-((1-Amino-5-carbamoylisoquinolin-6-yl)amino)-2-oxo-1-((R)-3-oxo-4-(1-(pyridin-4-yl)-1H-pyrazol-3-yl)morpholin-2-yl)ethyl acetate (Compound 37-5)

(R)-2-((5-Carbamoyl-[bis(tert-butoxycarbonyl)amino]isoquinolin-6-yl)amino)-2-oxo-1-((R)-3-oxo-4-(1-(pyridin-4-yl)-1H-pyrazol-3-yl)morpholin-2-yl)ethyl acetate (66 mg, 0.089 mmol) was treated with triethylamine (2 mL) and the reaction was stirred at 25° C. for 20 min. The reaction mixture was evaporated. The residue was dissolved in MeOH (2 mL), purified by reverse phase HPLC (YMC-Pack Pro C18, 12505-2520WT, gradient from 5% MeCN to 60% MeCN in water (containing 0.2% ammonium formate) over 12 min) to afford (R)-2-(1-amino-5-carbamoylisoquinolin-6-yl)amino)-2-oxo-1-((R)-3-oxo-4-(1-(pyridin-4-yl)-1H-pyrazol-3-yl)morpholin-2-yl)ethyl acetate, as white solid. LCMS calc.=545.2. found=545.2 $(M+H)^+$.

Step 37-6: (R)-2-((S)-(7-Amino-1-oxo-1,4-dihydropyrido[4,3-f]quinazolin-3-yl)(hydroxy)methyl)-4-(1-(pyridin-4-yl)-1H-pyrazol-3-yl)morpholin-3-one A solution of NaOH (1.5 mL, 0.1 N in EtOH, 0.150 mmol) was added to a solution of (R)-2-((1-amino-5-carbamoylisoquinolin-6-yl)amino)-2-oxo-1-((R)-3-oxo-4-(1-(pyridin-4-yl)-1H-pyrazol-3-yl)morpholin-2-yl)ethyl acetate (42 mg, 0.077 mmol) in anhydrous EtOH (1 mL) at 25° C. The reaction mixture was stirred at 25° C. for 4 h. The reaction mixture was directly purified by reversed phase HPLC (YMC-Pack Pro C18, 12505-2520WT, gradient from 5% MeCN to 60% MeCN in water (containing 0.2% ammonium formate) over 30 min) to give the product as white solid, which was further purified by reversed phase HPLC (Waters Sunfire C18 column, 5 g particle size, 19×100 mm, linear gradient, gradient from 5% MeCN/water to 10% MeCN/water buffering with 0.16% TFA @ flow rate 50 mL/min over 17 min) to give the product of Example 37 as a TFA salt. LCMS calc.=485.16. found=485.16 (M+H)$^+$. $^1$H NMR (500 MHz, CD$_3$OD): δ 9.23 (d, J=7.5 Hz, 1H); 8.75 (d, J=6.5 Hz, 2H); 8.69 (d, J=9.0 Hz, 1H); 8.63 (d, J=3.0 Hz, 1H); 8.21 (d, J=7.0 Hz, 2H); 7.94 (d, J=9.5 Hz, 1H); 7.81 (d, J=7.5 Hz, 1H); 7.41 (d, J=2.5 Hz, 1H); 5.44 (d, J=2.0 Hz, 1H); 5.01 (d, J=2.0 Hz, 1H); 4.33-4.30 (m, 1H), 4.26-4.24 (m, 1H), 4.20-4.15 (m, 1H), 4.04-4.00 (m, 1H).

Intermediate 9

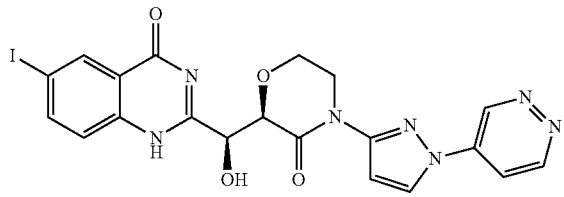 [SMILES: O=C1[C@@H]([C@@H](O)c2nc(=O)c3cc(I)ccc3[nH]2)OCCN1c1ccn(-c2ccnnc2)n1]

(R)-2-((S)-Hydroxy(6-iodo-4-oxo-1,4-dihydroquinazolin-2-yl)methyl)-4-(1-(pyridazin-4-yl)-1H-pyrazol-3-yl)morpholin-3-one Step 9-1: (3-Iodo-1H-pyrazol-1-yl)methyl pivalate (intermediate 9-1)

3-Iodo-1H-pyrazole (19.44 g, 100 mmol) was charged to a flask followed by THF (237 mL) and the solution was cooled to −10° C. NaH (4.41 g, 110 mmol) was added in portions keeping the internal temperature below −10° C. The reaction was stirred for 30 min, then chloromethyl pivalate (17.45 mL, 120 mmol) was added and the reaction was stirred for 1 h at −10° C. and then allowed to warm to room temperature. The reaction was cooled in an ice bath and quenched with sat. NH$_4$Cl then diluted with EtOAc and water. The organic layer was washed with brine, dried over MgSO$_4$ and the solvent was removed. The product was purified by flash chromatography eluting with 0-50% EtOAc/hexane to give (3-iodo-1H-pyrazol-1-yl)methyl pivalate, as a white solid. LCMS calc.=309.01. found=308.87 (M+H$^+$).

Step 9-2: (3-((R)-2-((R)-2-(tert-Butoxy)-1-hydroxy-2-oxoethyl)-3-oxomorpholino)-1H-pyrazol-1-yl) methyl pivalate (intermediate 9-2)

(R)-tert-Butyl 2-hydroxy-2-((R)-3-oxomorpholin-2-yl) acetate (6.56 g, 21.29 mmol), (3-iodo-1H-pyrazol-1-yl) methyl pivalate (5.42 g, 23.42 mmol), potassium phosphate tribasic (9.04 g, 42.6 mmol) and 1,4-dioxane (65.6 mL) was charged to a vial and degassed for 5 min. Copper (I) iodide (4.05 g, 21.29 mmol) was added and the reaction was degassed for 20 min. trans-N,N-Dimethylcyclohexane-1,2-diamine (3.46 mL, 21.29 mmol) was then added and the reaction degassing was continued while heating to 85° C. (degassing stopped once internal temperature reached 50° C.). The reaction was stirred for 3 h. The reaction was cooled and filtered. The reaction was reverse quenched into 2N HCl (25 mL). The batch was filtered again, then the layers were separated. The organic phase was washed with NaHCO$_3$ and brine then dried over MgSO$_4$ and solvent was removed to give the crude product (5.3 g). The compound was purified by flash chromatography eluting with 0-60% EtOAc/hexane to give (3-((R)-2-((R)-2-(tert-butoxy)-1-hydroxy-2-oxoethyl)-3-oxomorpholino)-1H-pyrazol-1-yl)methyl pivalate, as a white solid. LCMS calc.=434.19. found=434.07 (M+Na$^+$).

Step 9-3: (R)-2-Hydroxy-2-((R)-3-oxo-4-(1-((pivaloyloxy)methyl)-1H-pyrazol-3-yl)morpholin-2-yl) acetic acid (intermediate 9-3)

(3-((R)-2-((R)-2-(tert-Butoxy)-1-hydroxy-2-oxoethyl)-3-oxomorpholino)-1H-pyrazol-1-yl)methyl pivalate (4 g, 9.72 mmol) was charged to a flask and dissolved in TFA (20 mL). After 45 min dichloroethane was added and the solvent removed (2×50 mL). The batch was crystallized from EtOAc/heptane to give (R)-2-hydroxy-2-((R)-3-oxo-4-(1-((pivaloyloxy)methyl)-1H-pyrazol-3-yl)morpholin-2-yl) acetic acid, as a white solid. LCMS calc.=378.13. found=378.08 (M+Na$^+$).

Step 9-4: (3-((R)-2-((R)-2-((2-Carbamoyl-4-iodophenyl)amino)-1-hydroxy-2-oxoethyl)-3-oxomorpholino)-1H-pyrazol-1-yl)methyl pivalate (intermediate 9-4)

(R)-2-Hydroxy-2-((R)-3-oxo-4-(1-((pivaloyloxy) methyl)-1H-pyrazol-3-yl)morpholin-2-yl)acetic acid (5 g, 14.07 mmol), 2-amino-5-iodobenzamide (3.80 g, 14.07 mmol), HATU (5.35 g, 14.07 mmol), and 1-hydroxy-7-azabenzotriazole (1.915 g, 14.07 mmol) were charged to a flask and dissolved in DMF (50.0 mL). DIPEA (4.92 mL, 28.1 mmol) was added and the reaction was stirred overnight. The reaction was quenched with sat NH$_4$Cl and diluted with EtOAc and water. The organic phase was washed with brine, dried over MgSO$_4$ then filtered and solvent was removed. The compound purified by flash chromatography eluting with 0-5% MeOH/CH$_2$Cl$_2$ to give (3-((R)-2-((R)-2-((2-carbamoyl-4-iodophenyl)amino)-1-hydroxy-2-oxoethyl)-3-oxomorpholino)-1H-pyrazol-1-yl) methyl pivalate, as a white solid. LCMS calc.=600.10. found=600.08 (M+H$^+$).

Step 9-5: (R)-2-((S)-Hydroxy(6-iodo-4-oxo-1,4-dihydroquinazolin-2-yl)methyl)-4-(1H-pyrazol-3-yl) morpholin-3-one (intermediate 9-5)

(3-(((R)-2-((R)-2-((2-Carbamoyl-4-iodophenyl)amino)-1-hydroxy-2-oxoethyl)-3-oxomorpholino)-1H-pyrazol-1-yl) methyl pivalate (3.2 g, 5.34 mmol) was charged to a flask and dissolved in MeOH (32.0 mL). Potassium tert-butoxide (10.68 mL of a 1 M soln in t-BuOH, 10.68 mmol) was added and the reaction was stirred at room temperature for 3 h. The reaction was quenched with acetic acid (0.611 mL, 10.68 mmol). EtOAc and water were added. The organic layer was washed with sat NH$_4$Cl and brine. The organic layer was dried over MgSO$_4$, filtered and the solvent was removed to give (R)-2-((S)-hydroxy(6-iodo-4-oxo-1,4-dihydroquinazolin-2-yl)methyl)-4-(1H-pyrazol-3-yl)morpholin-3-one. This was used in the next step without further purification. LCMS calc.=468.02. found=467.90 (M+H$^+$).

Step 9-6: (R)-2-((S)-Hydroxy(6-iodo-4-oxo-1,4-dihydroquinazolin-2-yl)methyl)-4-(1-(pyridazin-4-yl)-1H-pyrazol-3-yl)morpholin-3-one (R)-2-((S)-Hydroxy(6-iodo-4-oxo-1,4-dihydroquinazolin-2-yl)methyl)-4-(1-(pyridazin-4-yl)-1H-pyrazol-3-yl)morpholin-3-one (508 mg, 1.087 mmol), 4-iodopyridazine (336 mg, 1.631 mmol), copper (I) iodide (62.1 mg, 0.326 mmol) and K$_2$CO$_3$ (301 mg, 2.175 mmol) were charged to a vial. DMSO (5080 µl) was added and the reaction was degassed (2-3 min). trans-N,N'-Dimethylcyclohexane-1,2-diamine (177 µl, 1.087 mmol) was added and the reaction was heated to 45° C. The reaction was cooled to room temperature, diluted with EtOAc and quenched with 1M AcOH. The organic layer was washed with satd NaHCO$_3$ and brine, then dried over MgSO$_4$, filtered and the solvent was removed. The compound was purified by flash chromatography eluting with 0-10% MeOH/CH$_2$Cl$_2$ to give Intermediate 9 as a pale yellow solid. LCMS calc.=546.04. found=546.00 (M+H$^+$).

EXAMPLE 38

(R)-2-((S)-hydroxy(4-oxo-6-(1H-pyrazol-4-yl)-1,4-dihydroquinazolin-2-yl)methyl)-4-(1-(pyridazin-4-yl)-1H-pyrazol-3-yl)morpholin-3-one To a vial was added (R)-2-((S)-hydroxy(6-iodo-4-oxo-1,4-dihydroquinazolin-2-yl)methyl)-4-(1-(pyridazin-4-yl)-1H-pyrazol-3-yl)morpholin-3-one (60 mg, 0.110 mmol), 1H-pyrazole-4-boronic acid (24.6 mg, 0.220 mmol), cesium carbonate (108 mg, 0.330 mmol) and PdCl$_2$(dppf)-CH$_2$Cl$_2$ adduct (18.0 mg, 0.022 mmol), then the vial was capped, degassed and DMA (0.8 mL) and water (0.1 mL) were added. The vial was degassed with N$_2$ at room temperature three times, then warmed up to 85° C. and stirred at 85° C. under N$_2$ overnight. The mixture was cooled to room temperature, diluted with DMA and water, filtered, and acidified with TFA (0.025 mL, 0.330 mmol) and directly purified by reversed phase HPLC (Waters Sunfire 19×100 mm, 5 uM, 5-70% MeCN (0.1% TFA) in water (0.1% TFA)) to afford the desired product (R)-2-((S)-hydroxy(4-oxo-6-(1H-pyrazol-4-yl)-1,4-dihydroquinazolin-2-yl)methyl)-4-(1-(pyridazin-4-yl)-1H-pyrazol-3-yl)morpholin-3-one, as white solid after lyophilization (the epimerized by-product was formed as a minor product, and separated from desired product). LCMS calc.=486.16. found=486.20 (M+H)$^+$. $^1$H NMR (500 MHz, DMSO-d$_6$): δ 9.82 (s, 1H); 9.27 (s, 1H); 8.20 (s, 1H); 8.28-8.05 (m, 7H); 7.67 (s, br, 2H); 7.23 (br s, 1H); 5.14 (d, J=1.5 Hz, 1H); 4.85 (s, 1H); 4.21-3.97 (m, 4H).

The following compounds (Table 5) were synthesized using methods analogous to those described for EXAMPLE 38 from commercially available materials or intermediates whose syntheses are described above.

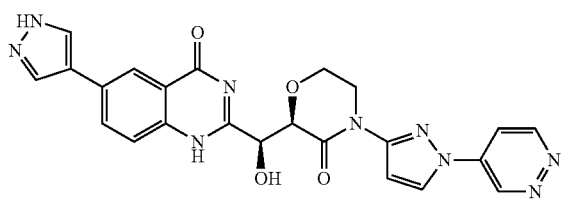 [SMILES: O=C1[C@@H]([C@@H](O)c2nc(=O)c3cc(-c4cn[nH]c4)ccc3[nH]2)OCCN1c1ccn(-c2ccnnc2)n1]

TABLE 5

| Example | | LCMS (M + H)$^+$ | Calc. (M + H)$^+$ |
|---|---|---|---|
| 39 | 2-{(S)-hydroxy[(2R)-3-oxo-4-(1-pyridazin-4-yl-1H-pyrazol-3-yl)morpholin-2-yl]methyl}-6-(1H-pyrazol-3-yl)quinazolin-4(1H)-one | 486.15 | 486.16 |
| 40 | 2-[(S)-hydroxy{(2R)-4-[1-(2-methoxypyridin-4-yl)-1H-pyrazol-3-yl]-3-oxomorpholin-2-yl}methyl]-6-(1H-pyrazol-4-yl)quinazolin-4(1H)-one | 515.08 | 515.18 |

TABLE 5-continued

| Example | | LCMS (M + H)+ | Calc. (M + H)+ |
|---|---|---|---|
| 41 | 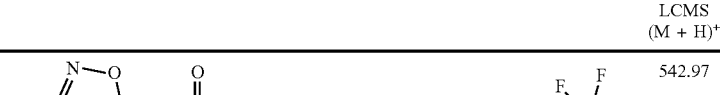 2-[(S)-hydroxy{(2R)-4-[1-(2-methoxypyridin-4-yl)-1H-pyrazol-3-yl]-3-oxomorpholin-2-yl}methyl]-6-(1H-pyrazol-4-yl)quinazolin-4(1H)-one | 515.09 | 515.18 |

The following compounds (Table 6) were synthesized using methods analogous to those described for EXAMPLE 1 from commercially available materials or intermediates whose syntheses are described above.

TABLE 6

| Example | | LCMS (M + H)+ | Calc. (M + H)+ |
|---|---|---|---|
| 42 | 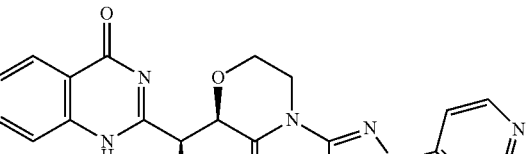 3-amino-7-{(S)-hydroxy[(2R)-3-oxo-4-{1-[2-(trifluoromethyl)pyridin-4-yl]-1H-pyrazol-3-yl}morpholin-2-yl]methyl}isoxazolo[5,4-f]quinazolin-9(6H)-one | 542.97 | 543.14 |

Additional examples of the present invention prepared according to procedures similar to those described above include:

Determination of Inhibitory Activity Against Factor IXa

Formation of a clot to stem bleeding at a site of blood vessel injury involves the coordinated activity of a group of plasma proteins that initiate and propagate fibrin formation and subsequently protect fibrin from premature degradation. Factor IX is a key component of the plasma system that forms a fibrin clot at a site of vascular injury. The activity of

| Structure | Name (FIXa Low Enzyme (nM) |
|---|---|
| 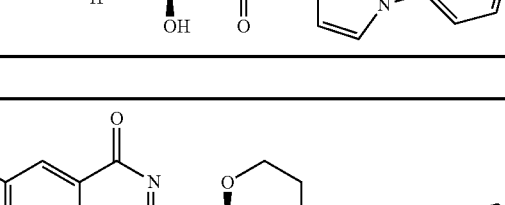 | (R)-2-((S)-(6-amino-4-oxo-1,4-dihydropyrido[3,4-g]quinazolin-2-yl)(hydroxy)methyl)-4-(1-(pyridin-4-yl)-1H-pyrazol-3-yl)morpholin-3-one (27.618) |

| Structure | Name (Exact Mass [M + H] +) |
|---|---|
| 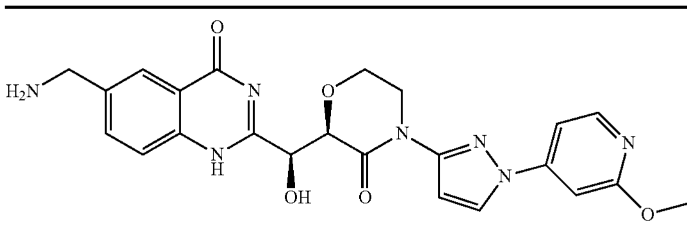 | 6-(aminomethyl)-2-[(S)-hydroxy{(2R)-4-[1-(2-methoxypyridin-4-yl)-1H-pyrazol-3-yl]-3-oxomorpholin-2-yl}methyl]quinazolin-4(1H)-one (478.18) |

Factor IXa is measured by monitoring the cleavage of the fluorescent peptide, $CH_3SO_2$-D-CHG-Gly-Arg-AFC.AcOH ("CHG" is cyclohexyl-glycine and "AFC" is trifluoro aminomethyl coumarin). Factor IXa cleaves the amide bond between Arg and AFC, thereby releasing the AFC fluorophore. The free AFC can be detected with a fluorescence detector at an excitation wavelength of 405 nM and emission wavelength of 510 nM.

Factor IXa Inhibition

| Example | Name (FIXa Low Enzyme (nM)) |
|---|---|
| 1 | 3-amino-7-((S)-hydroxy((R)-3-oxo-4-(1-(pyridin-4-yl)-1H-pyrazol-3-yl)morpholin-2-yl)methyl)isoxazolo[5,4-f]quinazolin-9(6H)-one (14.508) |
| 2 | (R)-2-((S)-(3-amino-9-oxo-6,9-dihydroisothiazolo[5,4-f]quinazolin-7-yl)(hydroxy)methyl)-4-(1-(pyridin-4-yl)-1H-pyrazol-3-yl)morpholin-3-one (4.65) |
| 16 | (R)-2-((S)-(3-amino-9-oxo-6,9-dihydroisothiazolo[5,4-f]quinazolin-7-yl)(hydroxy)methyl)-4-(5-methyl-1-(tetrahydro-2H-pyran-4-yl)-1H-pyrazol-3-yl)morpholin-3-one (31.866) |
| 15 | (R)-2-((S)-(3-amino-9-oxo-6,9-dihydroisothiazolo[5,4-f]quinazolin-7-yl)(hydroxy)methyl)-4-(1-cyclopropyl-1H-pyrazol-3-yl)morpholin-3-one (39.78) |
| 4 | (R)-2-((S)-(3-amino-9-oxo-6,9-dihydroisothiazolo[5,4-f]quinazolin-7-yl)(hydroxy)methyl)-4-(5-methyl-1-(pyridin-3-yl)-1H-pyrazol-3-yl)morpholin-3-one (58.612) |
| 14 | (R)-2-((S)-(3-amino-9-oxo-6,9-dihydroisothiazolo[5,4-f]quinazolin-7-yl)(hydroxy)methyl)-4-(1,5-dimethyl-1H-pyrazol-3-yl)morpholin-3-one (43.726) |
| 11 | (R)-2-((S)-(3-amino-9-oxo-6,9-dihydroisothiazolo[5,4-f]quinazolin-7-yl)(hydroxy)methyl)-4-(1-(4-fluorophenyl)-5-methyl-1H-pyrazol-3-yl)morpholin-3-one (52.139) |
| 8 | (R)-2-((S)-(3-amino-9-oxo-6,9-dihydroisothiazolo[5,4-f]quinazolin-7-yl)(hydroxy)methyl)-4-(5-methyl-1-(2-(trifluoromethyl)pyridin-4-yl)-1H-pyrazol-3-yl)morpholin-3-one (17.85) |
| 5 | (R)-2-((S)-(3-amino-9-oxo-6,9-dihydroisothiazolo[5,4-f]quinazolin-7-yl)(hydroxy)methyl)-4-(1-(2-methoxypyridin-4-yl)-1H-pyrazol-3-yl)morpholin-3-one (10.803) |
| 7 | (R)-2-((S)-(3-amino-9-oxo-6,9-dihydroisothiazolo[5,4-f]quinazolin-7-yl)(hydroxy)methyl)-4-(1-(2-(trifluoromethyl)pyridin-4-yl)-1H-pyrazol-3-yl)morpholin-3-one (9.374) |
| 6 | (R)-2-((S)-(3-amino-9-oxo-6,9-dihydroisothiazolo[5,4-f]quinazolin-7-yl)(hydroxy)methyl)-4-(1-(2-methoxypyridin-4-yl)-5-methyl-1H-pyrazol-3-yl)morpholin-3-one (58.155) |
| 3 | (R)-2-((S)-(3-amino-9-oxo-6,9-dihydroisothiazolo[5,4-f]quinazolin-7-yl)(hydroxy)methyl)-4-(5-methyl-1-(pyridin-4-yl)-1H-pyrazol-3-yl)morpholin-3-one (11.277) |
| 13 | 4-(3-((R)-2-((S)-(3-amino-9-oxo-6,9-dihydroisothiazolo[5,4-f]quinazolin-7-yl)(hydroxy)methyl)-3-oxomorpholino)-1H-pyrazol-1-yl)-2-(trifluoromethyl)benzonitrile (28.265) |
| 17 | (R)-2-((S)-(3-amino-9-oxo-6,9-dihydroisothiazolo[5,4-f]quinazolin-7-yl)(hydroxy)methyl)-4-(6-(trifluoromethyl)pyridin-2-yl)morpholin-3-one (43.742) |
| 9 | (R)-2-((S)-(3-amino-9-oxo-6,9-dihydroisothiazolo[5,4-f]quinazolin-7-yl)(hydroxy)methyl)-4-(1-(pyridazin-4-yl)-1H-pyrazol-3-yl)morpholin-3-one (1.868) |
| 21 | (R)-2-((S)-(3-amino-9-oxo-6,9-dihydroisothiazolo[5,4-f]quinazolin-7-yl)(hydroxy)methyl)-4-(6-(2-hydroxypropan-2-yl)pyridin-2-yl)morpholin-3-one (12.33) |
| 19 | (R)-2-((S)-(3-amino-9-oxo-6,9-dihydroisothiazolo[5,4-f]quinazolin-7-yl)(hydroxy)methyl)-4-(6-(difluoromethoxy)pyridin-2-yl)morpholin-3-one (83.285) |
| 23 | 1-(6-((R)-2-((S)-(3-amino-9-oxo-6,9-dihydroisothiazolo[5,4-f]quinazolin-7-yl)(hydroxy)methyl)-3-oxomorpholino)pyridin-2-yl)cyclobutyl acetate (31.462) |
| 25 | (2R)-2-((S)-(3-amino-9-oxo-6,9-dihydroisothiazolo[5,4-f]quinazolin-7-yl)(hydroxy)methyl)-4-(6-(2,2,2-trifluoro-1-hydroxyethyl)pyridin-2-yl)morpholin-3-one (11.794) |
| 12 | 4-(3-((R)-2-((S)-(3-amino-9-oxo-6,9-dihydroisothiazolo[5,4-f]quinazolin-7-yl)(hydroxy)methyl)-3-oxomorpholino)-1H-pyrazol-1-yl)benzonitrile (3.068) |
| 24 | (R)-2-((S)-(3-amino-9-oxo-6,9-dihydroisothiazolo[5,4-f]quinazolin-7-yl)(hydroxy)methyl)-4-(6-(1-hydroxycyclobutyl)pyridin-2-yl)morpholin-3-one (24.772) |
| 20 | (R)-2-((S)-(3-amino-9-oxo-6,9-dihydroisothiazolo[5,4-f]quinazolin-7-yl)(hydroxy)methyl)-4-(6-cyclopropylpyridin-2-yl)morpholin-3-one (88.595) |
| 26 | (2R)-2-((S)-(3-amino-9-oxo-6,9-dihydroisothiazolo[5,4-f]quinazolin-7-yl)(hydroxy)methyl)-4-(6-(1,1,1-trifluoro-2-hydroxypropan-2-yl)pyridin-2-yl)morpholin-3-one (19.284) |
| 22 | (R)-2-((S)-(3-amino-9-oxo-6,9-dihydroisothiazolo[5,4-f]quinazolin-7-yl)(hydroxy)methyl)-4-(6-(2-hydroxypropan-2-yl)-5-(trifluoromethyl)pyridin-2-yl)morpholin-3-one (25.611) |

| Example | Name (FIXa Low Enzyme (nM)) |
| --- | --- |
| 18 | (R)-2-((S)-(3-amino-9-oxo-6,9-dihydroisothiazolo[5,4-f]quinazolin-7-yl)(hydroxy)methyl)-4-(3-fluoro-6-(trifluoromethyl)pyridin-2-yl)morpholin-3-one (44.229) |
| 10 | (R)-2-((S)-(3-amino-9-oxo-6,9-dihydroisothiazolo[5,4-f]quinazolin-7-yl)(hydroxy)methyl)-4-(1-(1-(difluoromethyl)-6-oxo-1,6-dihydropyridin-3-yl)-1H-pyrazol-3-yl)morpholin-3-one (3.041) |
| 27 | 3-Amino-7-((S)-hydroxy((R)-3-oxo-4-(1-(pyridin-4-yl)-1H-pyrazol-3-yl)morpholin-2-yl)methyl)isoxazolo[5,4-f]quinolin-9(6H)-one |
| 28 | (R)-2-((S)-(6-Amino-4-oxo-1,4-dihydropyrido[3,4-g]quinazolin-2-yl)(hydroxy)methyl)-4-(1-(pyridin-4-yl)-1H-pyrazol-3-yl)morpholin-3-one |

The present invention is not limited in scope by the specific embodiments disclosed in the examples which are intended as illustrations of a few aspects of the invention and any embodiments that are functionally equivalent are within the scope of this invention. Indeed, various modifications of the invention in addition to those shown and described herein will become apparent to those skilled in the relevant art and are intended to fall within the scope of the appended claim.

Compounds of the Formula (I) can be administered both as a monotherapy and in combination with other therapeutic agents, including antithrombotics (anticoagulants and platelet aggregation inhibitors), thrombolytics (plasminogen activators), other profibrinolytically active substances, hypotensives, blood sugar regulators, lipid-lowering agents and antiarrhythmics.

The Factor IXa inhibitors can also be co-administered with suitable anticoagulants, including, but not limited to, other Factor IXa inhibitors, thrombin inhibitors, thrombin receptor antagonists, factor VIIa inhibitors, factor Xa inhibitors, factor XIa inhibitors, factor XIIa inhibitors, adenosine diphosphate antiplatelet agents (e.g., P2Y12 antagonists), fibrinogen receptor antagonists (e.g. to treat or prevent unstable angina or to prevent reocclusion after angioplasty and restenosis), other anticoagulants such as aspirin, and thrombolytic agents such as plasminogen activators or streptokinase to achieve synergistic effects in the treatment of various vascular pathologies. Such anticoagulants include, for example, apixaban, dabigatran, cangrelor, ticagrelor, vorapaxar, clopidogrel, edoxaban, mipomersen, prasugrel, rivaroxaban, and semuloparin. For example, patients suffering from coronary artery disease, and patients subjected to angioplasty procedures, would benefit from coadministration of fibrinogen receptor antagonists and thrombin inhibitors. Factor IXa inhibitors may be administered first following thrombus formation, and tissue plasminogen activator or other plasminogen activator is administered thereafter.

Alternatively or additionally, one or more additional pharmacologically active agents may be administered in combination with a compound of the invention. The additional active agent (or agents) is intended to mean a pharmaceutically active agent (or agents) that is active in the body, including pro-drugs that convert to pharmaceutically active form after administration, which is different from the compound of the invention, and also includes free-acid, free-base and pharmaceutically acceptable salts of said additional active agents when such forms are sold commercially or are otherwise chemically possible. Generally, any suitable additional active agent or agents, including but not limited to anti-hypertensive agents, additional diuretics, anti-atherosclerotic agents such as a lipid modifying compound, anti-diabetic agents and/or anti-obesity agents may be used in any combination with the compound of the invention in a single dosage formulation (a fixed dose drug combination), or may be administered to the patient in one or more separate dosage formulations which allows for concurrent or sequential administration of the active agents (co-administration of the separate active agents). Examples of additional active agents which may be employed include but are not limited to angiotensin converting enzyme inhibitors (e.g, alacepril, benazepril, captopril, ceronapril, cilazapril, delapril, enalapril, enalaprilat, fosinopril, imidapril, lisinopril, moveltipril, perindopril, quinapril, ramipril, spirapril, temocapril, or trandolapril); angiotensin II receptor antagonists also known as angiotensin receptor blockers or ARBs, which may be in free-base, free-acid, salt or pro-drug form, such as azilsartan, e.g., azilsartan medoxomil potassium (EDARBI®), candesartan, e.g., candesartan cilexetil (ATACAND®), eprosartan, e.g., eprosartan mesylate (TEVETAN®), irbesartan (AVAPRO®), losartan, e.g., losartan potassium (COZAAR®), olmesartan, e.g, olmesartan medoximil (BENICAR®), telmisartan (MICARDIS®), valsartan (DIOVAN®), and any of these drugs used in combination with a thiazide-like diuretic such as hydrochlorothiazide (e.g., HYZAAR®, DIOVAN HCT®, ATACAND HCT®), etc.); potassium sparing diuretics such as amiloride HCl, spironolactone, epleranone, triamterene, each with or without HCTZ; neutral endopeptidase inhibitors (e.g., thiorphan and phosphoramidon); aldosterone antagonists; aldosterone synthase inhibitors; renin inhibitors; enalkrein; RO 42-5892; A 65317; CP 80794; ES 1005; ES 8891; SQ 34017; aliskiren (2(S),4(S),5(S),7(S)—N-(2-carbamoyl-2-methylpropyl)-5-amino-4-hydroxy-2,7-diisopropyl-8-[4-methoxy-3-(3-methoxypropoxy)-phenyl]-octanamid hemifumarate) SPP600, SPP630 and SPP635); endothelin receptor antagonists; vasodilators (e.g. nitroprusside); calcium channel blockers (e.g., amlodipine, nifedipine, verapamil, diltiazem, felodipine, gallopamil, niludipine, nimodipine, nicardipine); potassium channel activators (e.g., nicorandil, pinacidil, cromakalim, minoxidil, aprilkalim, loprazolam); sympatholitics; beta-adrenergic blocking drugs (e.g., acebutolol, atenolol, betaxolol, bisoprolol, carvedilol, metoprolol, metoprolol tartate, nadolol, propranolol, sotalol, timolol); alpha adrenergic blocking drugs (e.g., doxazocin, prazocin or alpha methyldopa); central alpha adrenergic agonists; peripheral vasodilators (e.g. hydralazine); lipid lowering agents, e.g., HMG-CoA reductase inhibitors such as simvastatin and lovastatin which are marketed as ZOCOR® and MEVACOR® in lactone pro-drug form and function as inhibitors after administration, and pharmaceutically acceptable salts of dihydroxy open ring acid HMG-CoA reductase inhibitors such as atorvastatin (particularly the calcium salt sold in LIPITOR®), rosuvastatin (particularly the calcium salt sold in CRESTOR®), pravastatin (particularly the sodium salt sold in PRAVACHOL®), and fluvastatin (particularly the sodium salt sold in LESCOL®); a cholesterol absorption inhibitor such as ezetimibe (ZETIA®), and ezetimibe in combination with any other lipid lowering agents such as the HMG-CoA reductase inhibitors noted above and particularly with simvastatin (VYTORIN®) or with atorvastatin calcium; niacin in immediate-release or controlled release forms, and particularly niacin in combination with a DP antagonist such as laropiprant (TREDAPTIVE®) and/or with an HMG-CoA reductase inhibitor; niacin in immediate-release or controlled release forms, and particularly niacin in combination with a DP antagonist such as laropiprant (TREDAPTIVE®) and/or with an HMG-CoA reductase inhibitor; niacin receptor agonists such as acipimox and acifran, as well as niacin receptor partial agonists; metabolic altering agents including insulin sensitizing agents and related compounds for the treatment of diabetes such as biguanides (e.g., metformin), meglitinides (e.g., repaglinide, nateglinide), sulfonylureas (e.g., chlorpropamide, glimepiride, glipizide, glyburide, tolazamide, tolbutamide), thiazolidinediones also referred to as glitazones (e.g., pioglitazone, rosiglitazone), alpha glucosidase inhibitors (e.g., acarbose, miglitol), dipeptidyl peptidase inhibitors, (e.g., sitagliptin (JANUVIA®), alogliptin, vildagliptin, saxagliptin, linagliptin, dutogliptin, gemigliptin), ergot alkaloids (e.g., bromocriptine), combination medications such as JANUMET® (sitagliptin with metformin), and injectable diabetes medications such as exenatide and pramlintide acetate; or with other drugs beneficial for the prevention or the treatment of the above-mentioned diseases including but not limited to diazoxide; and including the free-acid, free-base, and pharmaceutically acceptable salt forms, pro-drug forms, e.g., esters, and salts of pro-drugs of the above medicinal agents, where chemically possible. Trademark names of pharmaceutical drugs noted above are provided for exemplification of the marketed form of the active agent(s); such pharmaceutical drugs could be used in a separate dosage form for concurrent or sequential administration with a compound of the invention, or the active agent(s) therein could be used in a fixed dose drug combination including a compound of the invention.

Typical doses of Factor IXa inhibitors of the invention in combination with other suitable anti-platelet agents, anticoagulation agents, or thrombolytic agents may be the same as those doses of Factor IXa inhibitors administered without coadministration of additional anti-platelet agents, anticoagulation agents, or thrombolytic agents, or may be substantially less that those doses of thrombin inhibitors administered without coadministration of additional anti-platelet agents, anticoagulation agents, or thrombolytic agents, depending on a patient's therapeutic needs.

The compounds are administered to a mammal in a therapeutically effective amount. By "therapeutically effective amount" it is meant an amount of a compound of the present invention that, when administered alone or in combination with an additional therapeutic agent to a mammal, is effective to treat (i.e. prevent, inhibit or ameliorate) the thromboembolic and/or inflammatory disease condition or treat the progression of the disease in a host.

The compounds of the invention are preferably administered alone to a mammal in a therapeutically effective amount. However, the compounds of the invention can also be administered in combination with an additional therapeutic agent, as defined below, to a mammal in a therapeutically effective amount. When administered in a combination, the combination of compounds in preferably, but not necessarily, a synergistic combination. Synergy, as described for example by Chou and Talalay, Adv. Enzyme Regul. 1984, 22, 27-55, occurs when the effect (in this case, inhibition of the desired target) of the compounds when administered in combination is greater than the additive effect of the compounds when administered alone as a single agent. In general, a synergistic effect is most clearly demonstrated at suboptimal concentrations of the compounds. Synergy can be in terms of lower cytotoxicity, increased anticoagulant effect, or some other beneficial effect of the combination compared with the individual components.

By "administered in combination" or "combination therapy" it is meant that the compound of the present invention and one or more additional therapeutic agents are administered concurrently to the mammal being treated. When administered in combination each component may be administered at the same time or sequentially in any order at different points in time. Thus, each component may be administered separately but sufficiently closely in time so as to provide the desired therapeutic effect.

What is claimed is:
1. A compound of formula I

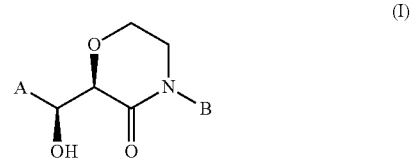

or a pharmaceutically acceptable salt thereof, wherein
A is
  1) a 9-10 membered bicyclic heterocycle having 2-3 heteroatoms independently selected from N, S and O, which 9-10 membered bicyclic heterocycle is unsubstituted or substituted with =O, —C(=NH)NH$_2$, or pyrazole, or
  2) a 12-, 13-, or 14-membered tricyclic heterocycle having 3-5 heteroatoms selected from N, S and O, which 12-, 13-, or 14-membered heterocycle is unsubstituted or substituted with =O or NH$_2$;
B is
  1) a 5-membered monocyclic heterocycle having 2 nitrogen atoms and 3 carbon atoms, where one 5-membered monocyclic heterocycle nitrogen is substituted with
    a) 6-membered monocyclic heterocyle having one or two nitrogen atoms or one oxygen atom,
    b) C$_{1-6}$ alkyl,
    c) C carbocycle, or
    d) aryl,
      wherein heterocycle, alkyl, carbocycle and aryl are unsubstituted, mono-substituted, or independently di-substituted with CF$_3$, OCH$_3$, F, CN, CHF$_2$, or =O,
    and one 5-membered monocyclic heterocycle carbon atom is unsubstituted or substituted with C$_{1-6}$ alkyl, or
  2) a 6-membered monocyclic heterocycle having 1 nitrogen atom and 5 carbon atoms, where three carbon atoms are unsubstituted, and one or two carbon atoms are independently unsubstituted or independently substituted with CF$_3$, —C(CH$_3$)$_2$OH, —OCHF$_2$, —CH(CF$_3$)OH, —C(CF$_3$)(CH$_3$)OH, F,

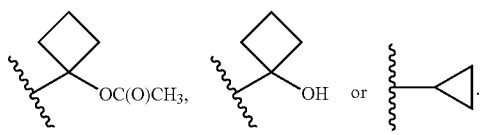

2. A compound of claim 1, or a pharmaceutically acceptable salt thereof, wherein
A has the formula (II)

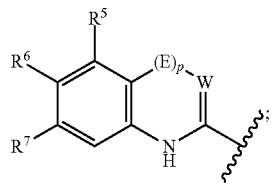

(II)

wherein
W is N or CH;
E is S(O)$_2$ or C(O);
p is 0 or 1;
R$^5$ is H or, together with R$^6$ and the atoms to which they are attached, forms a 5- or 6-membered monocyclic heterocycle having 2 heteroatoms independently selected from N, S and O, which heterocycle is substituted at a carbon atom with NH$_2$;
R$^6$ is H, —C(=NH)NH$_2$, pyrazole, or, together with R$^5$ and the atoms to which they are attached, forms a 5- or 6-membered monocyclic heterocycle, having 2 heteroatoms independently selected from N, S and O, which heterocycle is substituted at a carbon atom with NH$_2$, or, provided R$^5$ and R$^6$ do not form a heterocycle, forms, together with R$^7$ and the atoms to which they are attached, a 5-membered monocyclic heterocycle, having 2 heteroatoms independently selected from N, S and O, or forms, together with R$^7$ and the atoms to which they are attached, a 6-membered monocyclic heterocycle having 1 N atom, which 5- or 6-membered heterocycle is substituted at a carbon atom with NH$_2$;
R$^7$ is H, —C(=NH)NH$_2$, or, provided R$^5$ and R$^6$ do not form a heterocycle,
forms, together with R$^6$ and the atoms to which they are attached, a 5-membered monocyclic heterocycle, having 2 heteroatoms independently selected from N, S and O, or forms, together with R$^6$ and the atoms to which they are attached, a 6-membered monocyclic heterocycle having 1 N atom, which 5- or 6-membered heterocycle is substituted at a carbon atom with NH$_2$;
provided R$^5$, R$^6$ and R$^7$ are not simultaneously H; and
B is
1) a 5-membered monocyclic heterocycle having 2 nitrogen atoms and 3 carbon atoms, where one 5-membered monocyclic heterocycle nitrogen is substituted with

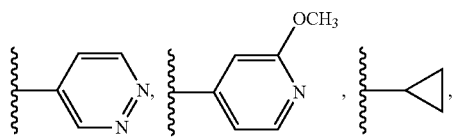

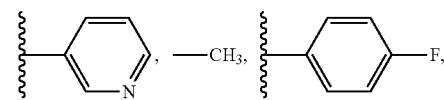

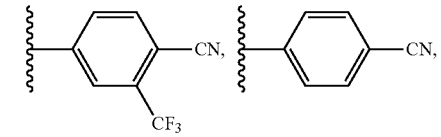

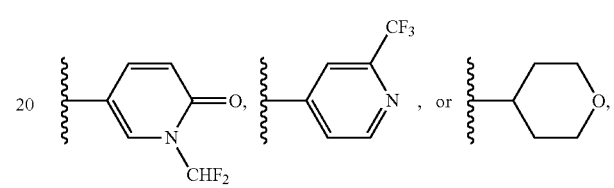

and one carbon atom in the 5-membered monocyclic heterocycle is unsubstituted or substituted with —CH$_3$, or
2) a 6-membered monocyclic heterocycle having 1 nitrogen atom and 5 carbon atoms, where one or two carbon atoms are independently unsubstituted or independently substituted with CF$_3$, —C(CH$_3$)$_2$OH, —OCHF$_2$, —CH(CF$_3$)OH, —C(CF$_3$)(CH$_3$)OH, F,

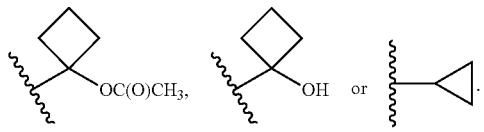

3. A compound of claim 1, or a pharmaceutically acceptable salt thereof, wherein
A is

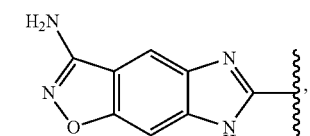

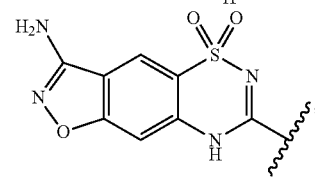

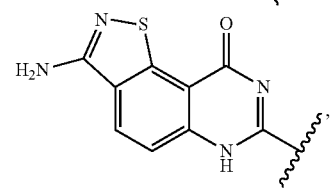

103
-continued
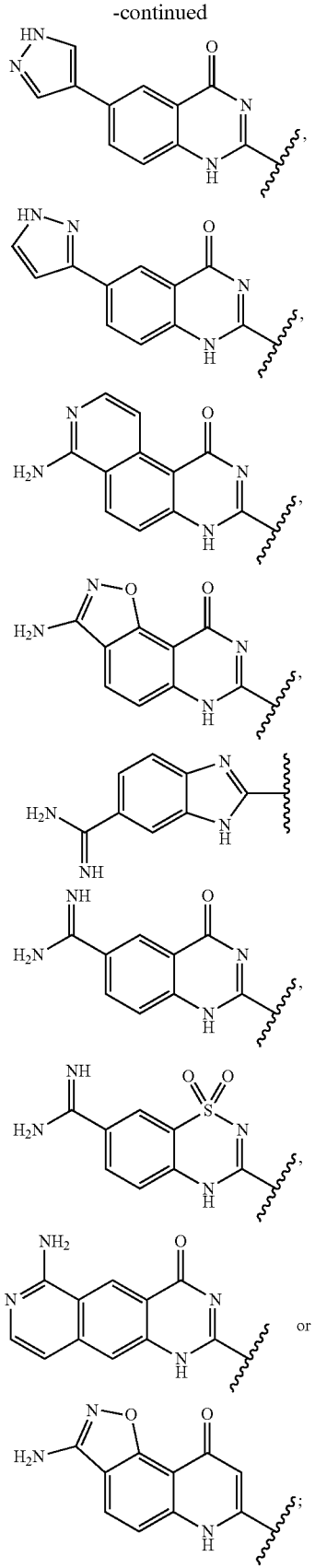
and
104
B is
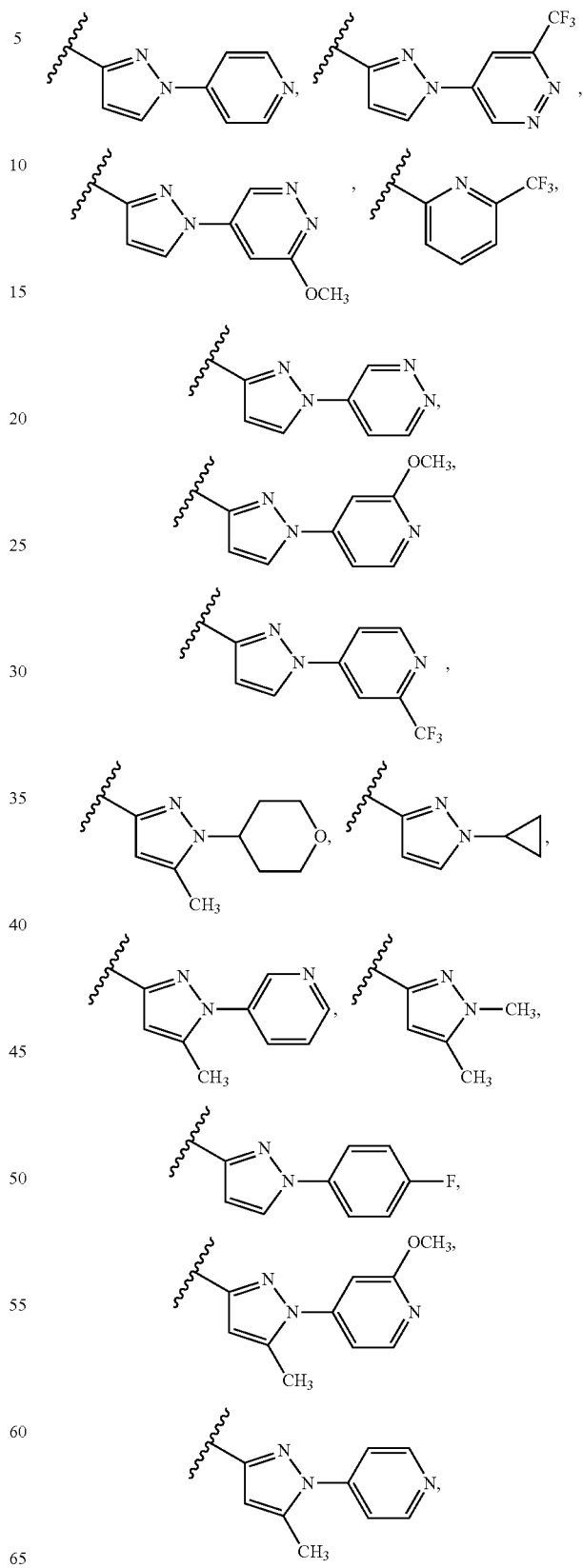

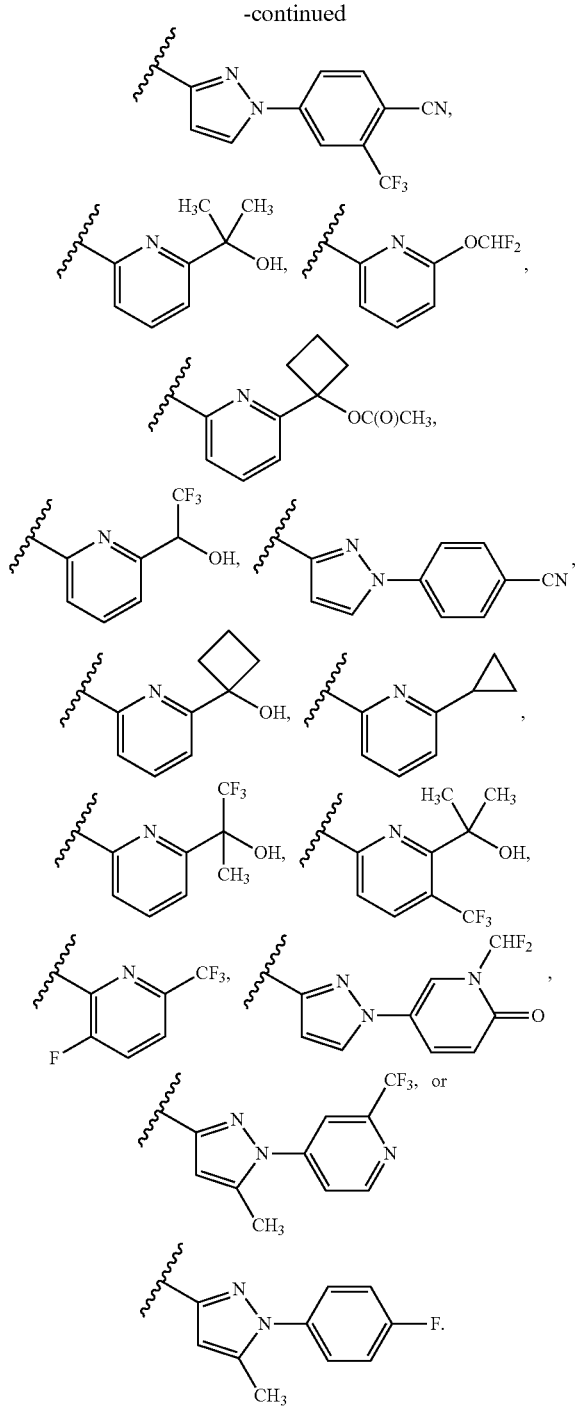

4. A compound of claim 1, or a pharmaceutically acceptable salt thereof, which is 3-Amino-7-((S)-hydroxy((R)-3-oxo-4-(1-(pyridin-4-yl)-1H-pyrazol-3-yl)morpholin-2-yl)methyl)isoxazolo[5,4-f]quinazolin-9(6H)-one, (R)-2-((S)-(3-Amino-9-oxo-6,9-dihydroisothiazolo[5,4-f]quinazolin-7-yl)(hydroxy)methyl)-4-(1-(pyridin-4-yl)-1H-pyrazol-3-yl)morpholin-3-one, (R)-2-((S)-(3-Amino-9-oxo-6,9-dihydroisothiazolo[5,4-f]quinazolin-7-yl)(hydroxy)methyl)-4-(5-methyl-1-(pyridin-4-yl)-1H-pyrazol-3-yl)morpholin-3-one, (R)-2-((S)-(3-Amino-9-oxo-6,9-dihydroisothiazolo[5,4-f]quinazolin-7-yl)(hydroxy)methyl)-4-(5-methyl-1-(pyridin-3-yl)-1H-pyrazol-3-yl)morpholin-3-one, (R)-2-((S)-(3-Amino-9-oxo-6,9-dihydroisothiazolo[5,4-f]quinazolin-7-yl)(hydroxy)methyl)-4-(1-(2-methoxypyridin-4-yl)-1H-pyrazol-3-yl)morpholin-3-one, (R)-2-((S)-(3-Amino-9-oxo-6,9-dihydroisothiazolo[5,4-f]quinazolin-7-yl)(hydroxy)methyl)-4-(1-(2-methoxypyridin-4-yl)-5-methyl-1H-pyrazol-3-yl)morpholin-3-one, (R)-2-((S)-(3-Amino-9-oxo-6,9-dihydroisothiazolo[5,4-f]quinazolin-7-yl)(hydroxy)methyl)-4-(1-(2-(trifluoromethyl)pyridin-4-yl)-1H-pyrazol-3-yl)morpholin-3-one, (R)-2-((S)-(3-Amino-9-oxo-6,9-dihydroisothiazolo[5,4-f]quinazolin-7-yl)(hydroxy)methyl)-4-(5-methyl-1-(2-(trifluoromethyl)pyridin-4-yl)-1H-pyrazol-3-yl)morpholin-3-one, (R)-2-((S)-(3-Amino-9-oxo-6,9-dihydroisothiazolo[5,4-f]quinazolin-7-yl)(hydroxy)methyl)-4-(1-(pyridazin-4-yl)-1H-pyrazol-3-yl)morpholin-3-one, (R)-2-((S)-(3-Amino-9-oxo-6,9-dihydroisothiazolo[5,4-f]quinazolin-7-yl)(hydroxy)methyl)-4-(1-(1-(difluoromethyl)-6-oxo-1,6-dihydropyridin-3-yl)-1H-pyrazol-3-yl)morpholin-3-one, (R)-2-((S)-(3-Amino-9-oxo-6,9-dihydroisothiazolo[5,4-f]quinazolin-7-yl)(hydroxy)methyl)-4-(1-(4-fluorophenyl)-5-methyl-1H-pyrazol-3-yl)morpholin-3-one, 4-(3-((R)-2-((S)-(3-Amino-9-oxo-6,9-dihydroisothiazolo[5,4-f]quinazolin-7-yl)(hydroxy)methyl)-3-oxomorpholino)-1H-pyrazol-1-yl)benzonitrile, 4-(3-((R)-2-((S)-(3-Amino-9-oxo-6,9-dihydroisothiazolo[5,4-f]quinazolin-7-yl)(hydroxy)methyl)-3-oxomorpholino)-1H-pyrazol-1-yl)-2-(trifluoromethyl)benzonitrile, (R)-2-((S)-(3-Amino-9-oxo-6,9-dihydroisothiazolo[5,4-f]quinazolin-7-yl)(hydroxy)methyl)-4-(1,5-dimethyl-1H-pyrazol-3-yl)morpholin-3-one, (R)-2-((S)-(3-Amino-9-oxo-6,9-dihydroisothiazolo[5,4-f]quinazolin-7-yl)(hydroxy)methyl)-4-(1-cyclopropyl-1H-pyrazol-3-yl)morpholin-3-one, (R)-2-((S)-(3-Amino-9-oxo-6,9-dihydroisothiazolo[5,4-f]quinazolin-7-yl)(hydroxy)methyl)-4-(5-methyl-1-(tetrahydro-2H-pyran-4-yl)-1H-pyrazol-3-yl)morpholin-3-one, (R)-2-((S)-(3-Amino-9-oxo-6,9-dihydroisothiazolo[5,4-f]quinazolin-7-yl)(hydroxy)methyl)-4-(6-(trifluoromethyl)pyridin-2-yl)morpholin-3-one, (R)-2-((S)-(3-Amino-9-oxo-6,9-dihydroisothiazolo[5,4-f]quinazolin-7-yl)(hydroxy)methyl)-4-(3-fluoro-6-(trifluoromethyl)pyridin-2-yl)morpholin-3-one, (R)-2-((S)-(3-Amino-9-oxo-6,9-dihydroisothiazolo[5,4-f]quinazolin-7-yl)(hydroxy)methyl)-4-(6-(difluoromethoxy)pyridin-2-yl)morpholin-3-one, (R)-2-((S)-(3-Amino-9-oxo-6,9-dihydroisothiazolo[5,4-f]quinazolin-7-yl)(hydroxy)methyl)-4-(6-cyclopropylpyridin-2-yl)morpholin-3-one, (R)-2-((S)-(3-Amino-9-oxo-6,9-dihydroisothiazolo[5,4-f]quinazolin-7-yl)(hydroxy)methyl)-4-(6-(2-hydroxypropan-2-yl)pyridin-2-yl)morpholin-3-one, (R)-2-((S)-(3-Amino-9-oxo-6,9-dihydroisothiazolo[5,4-f]quinazolin-7-yl)(hydroxy)methyl)-4-(6-(2-hydroxypropan-2-yl)-5-(trifluoromethyl)pyridin-2-yl)morpholin-3-one, 1-(6-((R)-2-((S)-(3-Amino-9-oxo-6,9-dihydroisothiazolo[5,4-f]quinazolin-7-yl)(hydroxy)methyl)-3-oxomorpholino)pyridin-2-yl)cyclobutyl acetate, (R)-2-((S)-(3-Amino-9-oxo-6,9-dihydroisothiazolo[5,4-f]quinazolin-7-yl)(hydroxy)methyl)-4-(6-(1-hydroxycyclobutyl)pyridin-2-yl)morpholin-3-one, (2R)-2-((S)-(3-Amino-9-oxo-6,9-dihydroisothiazolo[5,4-f]quinazolin-7-yl)(hydroxy)methyl)-4-(6-(2,2,2-trifluoro-1-hydroxyethyl)pyridin-2-yl)morpholin-3-one, (2R)-2-((S)-(3-Amino-9-oxo-6,9-dihydroisothiazolo[5,4-f]quinazolin-7-yl)(hydroxy)methyl)-4-(6-(1,1,1-trifluoro-2-hydroxypropan-2-yl)pyridin-2-yl)morpholin-3-one, 3-Amino-7-((S)-hydroxy((R)-3-oxo-4-(1-(pyridin-4-yl)-1H-pyrazol-3-yl)morpholin-2-yl)methyl)isoxazolo[5,4-f]quinolin-9(6H)-one, (R)-2-((S)-(6-Amino-4-oxo-1,4-dihydropyrido[3,4-g]quinazolin-2-yl)(hydroxy)methyl)-4-(1-(pyridin-4-yl)-1H-pyrazol-3-yl)morpholin-3-one, 2-((S)-Hydroxy((R)-3-oxo-4-(p-tolyl)morpholin-2-yl)methyl)-4-oxo-1,4-dihydroquinazoline-6-carboximidamide, 2-((S)-Hydroxy((R)-3-oxo-4-(p-tolyl)morpholin-2-yl)methyl)-1H-benzo[d]imidazole-6-carboximidamide, 3-((S)-Hydroxy((R)-3-oxo-4-(p-tolyl)morpholin-2-yl)methyl)-4H-benzo[e][1,2,4]thiadiazine-7-carboximidamide 1,1-dioxide, (2R)-2-[(S)-(3-amino-7H-imidazo[4,5-f][1,2]benzisoxazol-6-yl)(hydroxy)methyl]-4-(1-pyridin-4-yl-1H-pyrazol-3-yl)morpholin-3-one, (2R)-2-[(S)-(3-amino-7H-imidazo[4,5-f][1,2]benzisoxazol-6-yl)(hydroxy)methyl]-4-[1-(6-methoxy-pyridazin-4-yl)-1H-pyrazol-3-yl]morpholin-3-one, (R)-2-((S)-(8-Amino-1,1-dioxido-4H-isoxazolo[4′,5′:4,5]benzo[1,2-e][1,2,4]thiadiazin-3-yl)(hydroxy)methyl)-4-(1-(pyridin-4-yl)-1H-pyrazol-3-yl)morpholin-3-one, (2R)-2-[(S)-(8-amino-1,1-dioxido-4H-isoxazolo[5,4-g][1,2,4]benzothiadiazin-3-yl)(hydroxy)methyl]-4-[6-(trifluoromethyl)pyridin-2-yl]morpholin-3-one, (R)-2-((S)-(7-Amino-1-oxo-1,4-dihydropyrido[4,3-f]quinazolin-3-yl)(hydroxy)methyl)-4-(1-(pyridin-4-yl)-1H-pyrazol-3-yl)morpholin-3-one, (R)-2-((S)-hydroxy(4-oxo-6-(1H-pyrazol-4-yl)-1,4-dihydroquinazolin-2-yl)methyl)-4-(1-(pyridazin-4-yl)-1H-pyrazol-3-yl)morpholin-3-one, 2-{(S)-hydroxy[(2R)-3-oxo-4-(1-pyridazin-4-yl-1H-pyrazol-3-yl)morpholin-2-yl]methyl}-6-(1H-pyrazol-3-yl)quinazolin-4(1H)-one, 2-[(S)-hydroxy{(2R)-4-[1-(2-methoxypyridin-4-yl)-1H-pyrazol-3-yl]-3-oxomorpholin-2-yl}methyl]-6-(1H-pyrazol-4-yl)quinazolin-4(1H)-one, 3-amino-7-{(S)-hydroxy[(2R)-3-oxo-4-{1-[2-(trifluoromethyl)pyridin-4-yl]-1H-pyrazol-3-yl}morpholin-2-yl]methyl}isoxazolo[5,4-f]quinazolin-9(6H)-one, (R)-2-((S)-(6-amino-4-oxo-1,4-dihydropyrido[3,4-g]quinazolin-2-yl)(hydroxy)methyl)-4-(1-(pyridin-4-yl)-1H-pyrazol-3-yl)morpholin-3-one, 2-((3-amino-9-oxo-6,9-dihydroisothiazolo[5,4-f]quinazolin-7-yl)(hydroxy)methyl)-4-(1-(pyridin-4-yl)-1H-pyrazol-3-yl)morpholin-3-one, 7-amino-3-{(S)-hydroxy[(2R)-3-oxo-4-(1-pyridin-4-yl-1H-pyrazol-3-yl)morpholin-2-yl]methyl}pyrido[4,3-f]quinazolin-1(4H)-one, or 6-(aminomethyl)-2-[(S)-hydroxy{(2R)-4-[1-(2-methoxypyridin-4-yl)-1H-pyrazol-3-yl]-3-oxomorpholin-2-yl}methyl]quinazolin-4(1H)-one.

5. A composition for inhibiting thrombus formation in blood comprising a compound of claim 1, or a pharmaceutically acceptable salt thereof, and a pharmaceutically acceptable carrier.

* * * * *